US012735727B2

(12) United States Patent
Olden et al.

(10) Patent No.: US 12,735,727 B2
(45) Date of Patent: Sep. 15, 2026

(54) STABILIZATION OF POLYETHYLENEIMINE-DEOXYRIBONUCLEIC ACID COMPLEX SIZE AND ACTIVITY

(71) Applicant: Juno Therapeutics, Inc., Seattle, WA (US)

(72) Inventors: Brynn Olden, Seattle, WA (US); Robert Barnes, Seattle, WA (US); Elizabeth Larimore, Seattle, WA (US); Julie Shi, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 868 days.

(21) Appl. No.: 17/921,291

(22) PCT Filed: Apr. 26, 2021

(86) PCT No.: PCT/US2021/029224

§ 371 (c)(1),
(2) Date: Oct. 25, 2022

(87) PCT Pub. No.: WO2021/222133

PCT Pub. Date: Nov. 4, 2021

(65) Prior Publication Data

US 2023/0183747 A1 Jun. 15, 2023

Related U.S. Application Data

(60) Provisional application No. 63/023,119, filed on May 11, 2020, provisional application No. 63/016,166, filed on Apr. 27, 2020.

(51) Int. Cl.
*C12N 15/10* (2006.01)
*C12N 15/88* (2006.01)

(52) U.S. Cl.
CPC ......... *C12N 15/88* (2013.01); *C12N 15/1006* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,686,279 | A | 11/1997 | Finer et al. |
| 5,994,136 | A | 11/1999 | Naldini et al. |
| 6,013,516 | A | 1/2000 | Verma et al. |
| 2018/0154023 | A1 | 6/2018 | Hochberg et al. |

FOREIGN PATENT DOCUMENTS

| | | |
|---|---|---|
| WO | WO 2016/115177 | 7/2016 |

OTHER PUBLICATIONS

Carrabino, Salvatore, et al. "Serum albumin enhances polyethyleniminemediated gene delivery to human respiratory epithelial cells." The -Journal of Gene Medicine: A cross-disciplinary journal for research on the science of gene transfer and its clinical applications 7.12 (2005): 1555-1564. (Year: 2005).*
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Carlisle et al., "Adenovirus hexon protein enhances nuclear delivery and increases transgene expression of polyethylenimine/plasmid DNA vectors," Mol Ther. (2001) 4(5):473-83.
Carrabino et al., "Serum albumin enhances polyethylenimine-mediated gene delivery to human respiratory epithelial cells," J Gene Med. (2005) 7(12):1555-64.
Dull et al., "A Third-Generation Lentivirus Vector with a Conditional Packaging System," J. Viral. (1998) 72:8463-8471.
Koste et al., "T-cell receptor transfer into human T cells with ecotropic retroviral vectors," Gene Therapy (2014) 21: 533-538.
Naldini et al., Efficient transfer, integration, and sustained long-term expression of the transgene in adult rat brains injected with a lentiviral vector, Proc Natl Acad Sci U S A. (1996) 93(21): 11382-11388.
Naldini et al., "In vivo gene delivery and stable transduction of nondividing cells by a lentiviral vector," Science. (1996) 272(5259): 263-267.
Naldini et al., "Lentiviruses as gene transfer agents for delivery to non-dividing cells", Curr Opin Biotechnol., Oct. 9, 1998; 5:457-63.
Ory et al., "A stable human-derived packaging cell line for production of high titer retrovirus/vesicular stomatitis virus G pseudotypes," Proc Natl Acad Sci U S A. Oct. 15, 1996; 93(21):11400-6.
Park et al., "Treating cancer with genetically engineered T cells," Trends Biotechnol. (2011) 29(11): 550-557.
Tiyaboonchai et al., "Formulation and characterization of DNA-polyethylenimine-dextran sulfate nanoparticles," Eur J Pharm Sci. (2003) 19(4):191-202.
Zufferey et al., "Multiply attenuated lentiviral vector achieves efficient gene delivery in vivo," Nat Biotechnol. Sep. 1997;15(9):871-875.
Di Gioia et al., "Role of biophysical parameters on ex vivo and in vivo gene transfer to the airway epithelium by polyethylenimine/albumin complexes," Biomacromolecules (Mar. 2008, e-pub. Feb. 15, 2008) 9(3):859-866.

* cited by examiner

*Primary Examiner* — Michael D Burkhart
(74) *Attorney, Agent, or Firm* — Morrison & Foerster LLP

(57) ABSTRACT

Disclosed are methods and systems for producing polymer-DNA nanoparticles of a predetermined size. In one example, a method includes mixing together a first solution comprising deoxyribonucleic acid (DNA) with a second solution comprising a cationic polymer to obtain a polyplex solution, and at a predetermined time subsequent to mixing together the first solution and the second solution, adding a polyplex stabilizing agent to stabilize the size of the polyplex. In this way, transfection efficacy of the polymer-DNA nanoparticles may be improved, in particular with reference to transfection of suspension cells for production of viral vectors.

21 Claims, 26 Drawing Sheets

| Master Mix | | Addition Time (min) | | | | | | | |
|---|---|---|---|---|---|---|---|---|---|
| 1% v/v MM | Replicate | 0.5 | 1 | 1.5 | 2 | 2.5 | 3 | 3.5 | 4 |
| | 1 | 1.10E+07 | 2.04E+07 | 1.34E+07 | 1.79E+07 | 1.79E+07 | 1.13E+07 | 6.79E+06 | 5.52E+06 |
| | 2 | 2.16E+07 | 1.73E+07 | 2.36E+07 | 1.94E+07 | 1.94E+07 | 1.69E+07 | 9.06E+06 | 8.25E+06 |
| | 3 | 1.87E+07 | 2.42E+07 | 1.85E+07 | 2.36E+07 | 2.36E+07 | 1.70E+07 | 1.33E+07 | 1.27E+07 |
| | AVG | 1.71E+07 | 2.06E+07 | 1.85E+07 | 2.03E+07 | 2.03E+07 | 1.51E+07 | 9.73E+06 | 8.83E+06 |
| 3% v/v MM | Replicate | 0.5 | 1 | 1.5 | 2 | 2.5 | 3 | 4 | 8 |
| | 1 | 7.84E+06 | 1.16E+07 | 2.04E+07 | 3.19E+07 | 3.13E+07 | 3.39E+07 | 2.97E+07 | 1.90E+07 |
| | 2 | 4.61E+06 | 8.63E+06 | 2.05E+07 | 3.44E+07 | 3.54E+07 | 3.12E+07 | 2.88E+07 | 2.19E+07 |
| | 3 | 1.78E+07 | 1.22E+07 | 1.85E+07 | 3.63E+07 | 3.12E+07 | 3.74E+07 | 2.59E+07 | 1.99E+07 |
| | AVG | 1.01E+07 | 1.08E+07 | 1.98E+07 | 3.42E+07 | 3.26E+07 | 3.42E+07 | 2.81E+07 | 2.03E+07 |
| 10% v/v MM | Replicate | 2 | 3 | 4 | 5 | 6 | 8 | 10 | 15 |
| | 1 | 1.10E+07 | 2.04E+07 | 1.34E+07 | 1.79E+07 | 3.49E+07 | 1.13E+07 | 6.79E+06 | 5.52E+06 |
| | 2 | 2.16E+07 | 1.73E+07 | 2.36E+07 | 1.94E+07 | 3.82E+07 | 1.69E+07 | 9.06E+06 | 8.25E+06 |
| | 3 | 1.87E+07 | 2.42E+07 | 1.85E+07 | 2.36E+07 | 3.89E+07 | 1.70E+07 | 1.33E+07 | 1.27E+07 |
| | AVG | 1.71E+07 | 2.06E+07 | 1.85E+07 | 2.03E+07 | 3.73E+07 | 1.51E+07 | 9.73E+06 | 8.83E+06 |

FIG. 1B

| Run | Solution | Matrix | DNA conc (ug/mL) | PEI conc (ug/mL) | Albumin Conc (mg/mL) | Measurement Frequency |
|---|---|---|---|---|---|---|
| 1 | BalanCD neat | BalanCD | 0 | 0 | 0 | Single measurement, 60 s |
| 2 | BalanCD neat +HSA | BalanCD | 0 | 0 | 1 | Single measurement, 60 s |
| 3 | Plasmid in BalanCD | BalanCD | 500 | 0 | 0 | Single measurement, 60 s |
| 4 | PEI in BalanCD | BalanCD | 0 | 500 | 0 | Single measurement, 60 s |
| 5 | 22 ug/mL in BalanCD | BalanCD | 22 | 22 | 0 | 0 - 5 min: 15 s meas. every 15 s<br>5 - 60 min: 60 s meas. every 5 min |
| 6 | 73.3 ug/mL in BalanCD | BalanCD | 73.3 | 73.3 | 0 | 0 - 5 min: 15 s meas. every 15 s<br>5 - 60 min: 60 s meas. every 5 min |
| 7 | 220 ug/mL in BalanCD | BalanCD | 220 | 220 | 0 | 0 - 5 min: 15 s meas. every 15 s<br>5 - 60 min: 60 s meas. every 5 min |
| 8 | 22 ug/mL in BalanCD +HSA | BalanCD | 22 | 22 | 1 | 0 - 3 min: 15 s meas. every 15s (-HSA)<br>3 - 6 min: 15 s meas. every 15 s (+HSA)<br>6 - 60 min: 60 s meas. every 5 min (+HSA) |
| 9 | 73.3 ug/mL in BalanCD +HSA | BalanCD | 73.3 | 73.3 | 1 | 0 - 3 min: 15 s meas. every 15s (-HSA)<br>3 - 6 min: 15 s meas. every 15 s (+HSA)<br>6 - 60 min: 60 s meas. every 5 min (+HSA) |
| 10 | 220 ug/mL in BalanCD +HSA | BalanCD | 220 | 220 | 1 | 0 - 3 min: 15 s meas. every 15s (-HSA)<br>3 - 6 min: 15 s meas. every 15 s (+HSA)<br>6 - 60 min: 60 s meas. every 5 min (+HSA) |

FIG. 2A

| Plate ID | | Hold Times | | | | | |
|---|---|---|---|---|---|---|---|
| **Plate 1 - No HSA** | | 1 | 2 | 3 | 4 | 5 | 6 |
| | A | 1440 min | 1440 min | 1440 min | 30 min | 30 min | 30 min |
| | B | 1140 min | 1140 min | 1140 min | 20 min | 20 min | 20 min |
| | C | 120 min | 120 min | 120 min | 10 min | 10 min | 10 min |
| | D | 60 min | 60 min | 60 min | 2 min | 2 min | 2 min |
| | | | | | | | |
| **Plate 2 - +HSA** | | 1 | 2 | 3 | 4 | 5 | 6 |
| | A | 1440 min | 1440 min | 1440 min | 30 min | 30 min | 30 min |
| | B | 1140 min | 1140 min | 1140 min | 20 min | 20 min | 20 min |
| | C | 120 min | 120 min | 120 min | 10 min | 10 min | 10 min |
| | D | 60 min | 60 min | 60 min | 2 min | 2 min | 2 min |

FIG. 7B

STABILIZATION OF POLYETHYLENEIMINE-DEOXYRIBONUCLEIC ACID COMPLEX SIZE AND ACTIVITY

CROSS REFERENCE TO RELATED APPLICATIONS

This application is a national stage application under 35 U.S.C. § 371 of International Application No. PCT/US2021/029224, filed internationally on Apr. 26, 2021 which claims the priority benefit of the earlier filing date of U.S. Provisional Application No. 63/016,166, filed Apr. 27, 2020, and claims the priority benefit of the earlier filing date of U.S. Provisional Application No. 63/023,119, filed May 11, 2020, each of which are hereby incorporated by reference in their entirety.

FIELD

This disclosure relates generally to the field of viral vector process development and in particular, to methods of improving viral vector titer, production, and/or yield, such as by stabilizing polyethyleneimine (PEI)—deoxyribonucleic acid (DNA) complex activity and size.

BACKGROUND

Various gene therapy methods are available for treating diseases and conditions. Lentiviral vectors (LVVs) and Adeno-associated virus vectors (AAVs) play a pivotal role in a number of gene therapy processes. Many commercialized LVV production and/or AAV processes utilize adherent cell cultures for production. While these processes have been able to meet commercial demand, they require scale out to increase batch size, limiting the maximum process scale. Adherent processes also often require the addition of animal products like fetal bovine serum to maintain cell health. The use of animal-derived serum can increase possible contamination by adventitious agents, including viruses, and increase commercialization costs significantly. Thus, reliance on adherent cell cultures can complicate manufacturing of current Good Manufacturing Practices (cGMP)-grade LVVs and/or AAVs for clinical trials, and such issues can further exacerbate commercialization efforts. Improved methods for manufacturing and/or engineering such gene therapies are needed, including developing serum-free suspension processes to provide for more efficient and efficacious methods of viral vector production.

SUMMARY

Disclosed herein are methods and systems for providing polymer-DNA transfection complexes having a desired hydrodynamic diameter, for improving transfection efficacy and downstream gene expression, in particular with regard to expression of genes encoding viral particles (e.g., lentiviral vectors and/or adeno-associated viral vectors). The provided methods and systems improve the ability to scale up production of viral vectors for applications including, but not limited to, gene therapy and/or cellular therapy.

In an aspect, a disclosed method comprises adding a first predetermined amount of a PEI solution at a first concentration to a second predetermined amount of a DNA solution at a second concentration and mixing to obtain a PEI-DNA complex in solution, after a first predetermined duration, adding a third predetermined amount of a PEI-DNA transfection complex stabilizing agent to the PEI-DNA solution to obtain a stabilized PEI-DNA complex, and after a second predetermined duration subsequent to the first predetermined duration, transfecting a population of cells with the stabilized PEI-DNA complex.

In an embodiment, the method includes wherein the first predetermined duration is a function of the first concentration and the second concentration. In some embodiments, the first predetermined duration increases as the first concentration and the second concentration decrease, and wherein the first predetermined duration decreases as the first concentration and the second concentration increase.

In an embodiment, the first predetermined hold time is a function of a desired size of a PEI-DNA complex. In some examples, the desired size is between 400 and 1000 nanometers in diameter. In examples, the first predetermined hold time is between 30 seconds and 15 minutes. For example, the first predetermined hold time may be 30 seconds, between 30 seconds and 1 minute, between 1-2 minutes, between 2-3 minutes, between 3-4 minutes, between 4-5 minutes, between 5-6 minutes, between 6-7 minutes, between 7-8 minutes, between 8-9 minutes, between 9-10 minutes, between 10-11 minutes, between 11-12 minutes, between 12-13 minutes, between 13-14 minutes, or between 14-15 minutes. In specific examples, the first predetermined hold time is 30 seconds, 45 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, or 15 minutes.

In an embodiment, the DNA solution further comprises one or more DNA plasmids. As an example, the one or more DNA plasmids further comprise a transfer plasmid that includes one or more genes for synthesis of one or more viral proteins. In some examples, the one or more genes includes genes for at least a portion of a lentiviral genome. In additional or alternative examples, the one or more genes include genes for at least a portion of an adeno-associated viral genome.

In an embodiment, the population of cells further comprises mammalian cells. For example, the population of cells further comprises human embryonic kidney (HEK) 293 suspension cells. In other examples, the population of mammalian cells may include but are not limited to HeLa, U2OS, A549, HT1080, CAD, P19, NIH 3T3, L929, N2a, recombinant Chinese hamster ovary (CHO), MCF-7, Y79, SO-Rb50, Hep G2, DUKX-X11, J558L, and/or baby hamster kidney (BHK) cells.

In an embodiment, the stabilized PEI-DNA complex is not frozen prior to transfecting the population of cells.

In an embodiment, the second predetermined duration is between one minute and eighteen hours after addition of the PEI-DNA transfection complex stabilizing agent to the PEI-DNA solution.

In an embodiment, the second predetermined duration is greater than five minutes and less than two hours.

In an embodiment, the PEI-DNA transfection complex stabilizing agent is non-recombinant human serum albumin (HSA).

In an embodiment, the PEI-DNA transfection complex stabilizing agent is recombinant albumin purified from *Pichia pastoris*.

In an embodiment, the PEI-DNA transfection complex stabilizing agent is recombinant human serum albumin (HSA).

Also provided is a method for stabilizing a size of a polyplex comprising mixing together a first solution comprising deoxyribonucleic acid (DNA) with a second solution comprising a cationic polymer to obtain a polyplex solution, and at a predetermined time subsequent to mixing together the first solution and the second solution, adding a polyplex stabilizing agent to the polyplex solution to stabilize the size of the polyplex.

In an embodiment, the predetermined time is selected based on a desired size of the polyplex, and the desired size is between 400 and 1000 nanometers in diameter.

In an embodiment, the size of the polyplex increases as the predetermined time increases, and decreases as the predetermined time decreases.

In an embodiment, stabilizing the size of the polyplex is by adding the polyplex stabilizing agent to prevent the polyplex from continuing to increase in size.

In an embodiment, the polyplex stabilizing agent is non-recombinant human serum albumin (HSA).

In an embodiment, the polyplex stabilizing agent is recombinant human serum albumin purified from *Pichia pastoris*.

In an embodiment, the polyplex stabilizing agent is recombinant human serum albumin (HSA).

In an embodiment, the cationic polymer is polyethyleneimine (PEI).

In an embodiment, the first solution further comprises DNA at a first concentration, the second solution further comprises the cationic polymer at a second concentration, and the size of the polyplex is a function of one or more of the first concentration, the second concentration, and the predetermined time.

In an embodiment, the method further comprises mixing together the first solution with the second solution at a predetermined temperature.

In an embodiment, the method further comprises mixing together the first solution with the second solution at a predetermined pH.

In an embodiment, the method further comprises controlling a rate at which the first solution is mixed with the second solution.

In another aspect, a system for producing polymer-DNA nanoparticles of a defined size, comprises a polymer solution at a first concentration in a polymer chamber, a DNA solution at a second concentration in a DNA chamber, a mixing chamber selectively fluidically coupled to the polymer chamber via a first connection line and selectively fluidically coupled to the DNA chamber via a second connection line, a first pump coupled to the first connection line between the polymer chamber and the mixing chamber and a second pump coupled to the second connection line between the DNA chamber and the mixing chamber, a first valve coupled to the first connection line and positioned between the first pump and the mixing chamber, a second valve coupled to the second connection line and positioned between the second pump and the mixing chamber, and a quenching chamber that receives fluid flow from the mixing chamber via a third hose, the quenching chamber including a quenching agent at a third concentration.

In some embodiments, the system further comprises a controller storing instructions in non-transitory memory that, when executed, cause the controller to control one or more of the first pump, the second pump, the first valve and the second valve to route the polymer solution to the mixing chamber at a first flow rate and to simultaneously route the DNA solution to the mixing chamber at a second flow rate to provide a polymer-DNA complex within the mixing chamber that is then routed to the quenching chamber.

In an embodiment, the quenching agent is human serum albumin.

In an embodiment, the quenching agent is recombinant human serum albumin.

In an embodiment, the mixing chamber is of a defined geometry to facilitate consistent mixing and residence time of the polymer solution and the DNA solution as a function of the first flow rate and the second flow rate.

In an embodiment, growth of the polymer-DNA complex occurs within the mixing chamber, and the growth of the polymer-DNA complex is stabilized by the quenching agent upon the polymer-DNA complex being deposited in the quenching chamber to provide the polymer-DNA complex of the defined size.

In an embodiment, the defined size is between 400 and 1000 nanometers in diameter.

In an embodiment, the DNA solution further comprises a plurality of transfer plasmids that include one or more genes for synthesis of one or more viral proteins.

In an embodiment, the polymer solution further comprises polyethyleneimine.

In another aspect, a method for transfecting a population of cells with a reconstituted polymer-DNA transfection complex, comprises mixing together a DNA solution at a first concentration with a polymer solution at a second concentration to obtain a polymer-DNA transfection complex in solution. After a first predetermined time duration, the method includes stabilizing a size of the polymer-DNA transfection complex via a quenching agent to obtain a stabilized polymer-DNA transfection complex, adding one or more lyophilization agents to the stabilized polymer-DNA transfection complex, lyophilizing the stabilized polymer-DNA transfection complex to a powder. Then, at a later time, the method includes reconstituting the lyophilized stabilized polymer-DNA transfection complex to obtain the reconstituted polymer-DNA transfection complex, diluting the reconstituted polymer-DNA transfection complex into a transfection solution, and transfecting the population of cells with the reconstituted polymer-DNA transfection complex.

In an embodiment, the polymer solution further comprises a cationic polymer.

In an embodiment, the cationic polymer is polyethyleneimine (PEI).

In an embodiment, the quenching agent is human serum albumin (HSA).

In an embodiment, the DNA solution further comprises a plurality of transfer plasmids that code for at least a portion of a viral genome. In some examples, the viral genome comprises at least a portion of a lentivirus genome. In other examples, the viral genome comprises at least a portion of an adeno-associated viral genome.

In an embodiment, the powder is stored at one of 4° C., −20° C. or −80° C. until the later time.

In an embodiment, the lyophilization agent is one or more of mannitol and/or sucrose.

In an embodiment, the lyophilization agent includes both mannitol and sucrose, wherein a concentration of mannitol is between 25-35 mg/mL (e.g., 30 mg/mL) and a concentration of sucrose is between 15-25 mg/mL (e.g., 20 mg/mL).

In an embodiment, the lyophilization agent includes mannitol, but not sucrose, where a concentration of mannitol is between 25-35 mg/mL (e.g., 30 mg/mL).

The foregoing and other features of the disclosure will become more apparent from the following detailed description, which proceeds with reference to the accompanying figures.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 1B is a table showing titer values for samples of varying hold times prior to transfection, corresponding to the graph of FIG. 1C.

FIG. 2A is a table illustrating conditions for testing PEI-DNA transfection complex size as a function of time, for varying PEI-DNA transfection complex concentrations, both with and without HSA. The results of the test conditions detailed in the table of FIG. 2 are graphically illustrated in FIGS. 2B-6.

FIG. 7B depicts a plate map detailing experimental conditions tested to evaluate transfection efficacy of PEI-DNA complexes as a function of hold time with and without HSA for up to twenty-four hours.

DETAILED DESCRIPTION OF SEVERAL EMBODIMENTS

Figure 1A:
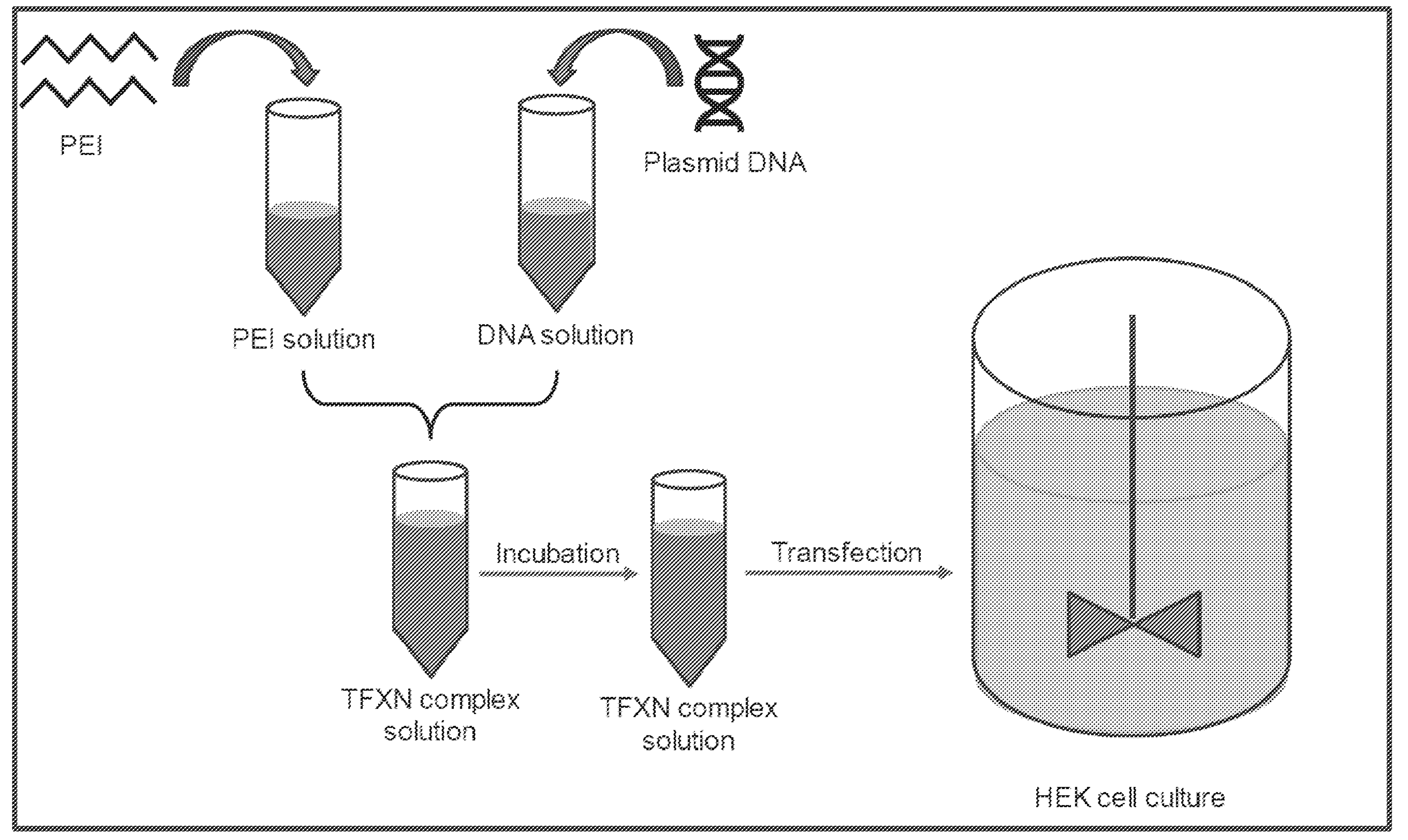
FIG. 1A is a schematic illustration of a high-level serum free suspension cell production process of the present disclosure.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

I. Overview of Several Embodiments

A major challenge involved in developing an effective cell suspension system for LVV production (and/or AAV production) is maintaining culture productivity when scaling up. The transfection unit operation is a crucial step in developing a suspension process and has a high impact on culture productivity. Cationic polymer-mediated (e.g., polyethylenimine) transient transfection is a method used for introducing genes of interest to host cells in viral production systems, and is an effective transfection technique for suspension production processes. While developing a serum-free suspension process for LVV production, it was unexpectedly found that PEI/DNA complex hold time was a highly time-sensitive process parameter that would present challenges during manufacturing scale-up. Using dynamic light scattering (DLS), it was found that polyplex (e.g., complex of cationic polymer and DNA) size increases with increased formation time, and that higher concentrations of DNA and PEI resulted in more rapid particle size increase. For example, when co-transfecting the components of a third generation LVV, maximum LVV titer was achieved by polyplexes of a specific size, and titer decreased as polyplex size increased beyond this optimal size.

Based upon these studies, disclosed herein are methods and systems which improve process control and titer output in transfection, such as in serum-free suspension transient transfection of viral vector components (e.g., LVV components and/or AAV components). The disclosed methods and systems facilitate efficient transfection and viral production, and are associated with numerous advantages. For example, the disclosed methods and systems are advantageous for numerous reasons including reducing the cost of viral particle production by allowing single-vessel scale up, rather than scale out, and not requiring the use of animal-derived raw materials. It is contemplated that the disclosed methods and systems can be applied to any transient transfection unit operation in a viral vector or protein production process that uses a cationic polymer such as polyethyleneimine (PEI) as the transfection reagent to deliver plasmid DNA to mammalian cells. Other cationic polymers within the scope of this disclosure include but are not limited to polylysine, polyornithine, polybrene, cyclodextrin, chitosan, histone, collagen, activated and/or non-activated dendrimers, and the like.

The disclosed systems and methods provide a polymer-DNA nanoparticle having a size (e.g., hydrodynamic particle diameter) within a predetermined size range. The predetermined size range may comprise a range in which transfection of a population of cells with the polymer-DNA transfection complex is more efficient and/or effective than if the polymer-DNA transfection complex size were outside of the predetermined size range. As an example, transfection of a population of cells with such a polymer-DNA transfection complex having dimensions within the predetermined size range increases viral vector titer (e.g., LVV titer, AAV titer, etc.) at harvest as compared with a population of cells transfected with the polymer-DNA transfection complex having dimensions outside of the predetermined size range. In examples, the predetermined size range is from 200-1400 nm in diameter. For example, between 400-1000 nm in diameter. Specifically, between 400-450 nm in diameter, or between 450-500 nm in diameter, or between 500-550 nm in diameter, or between 550-600 nm in diameter, or between 600-650 nm in diameter, or between 650-700 nm in diameter, or between 700-750 nm in diameter, or between 750-800 nm in diameter, or between 800-850 nm in diameter, or between 850-900 nm in diameter, or between 900-950 nm in diameter, or between 950-1000 nm in diameter.

In some embodiments, a method for stabilizing a size of a polyplex comprises mixing together a first solution comprising deoxyribonucleic acid (DNA) with a second solution comprising a cationic polymer to obtain a polyplex solution, and at a predetermined time subsequent to mixing together the first solution and the second solution, adding the polyplex stabilizing agent to the polyplex solution to stabilize the size of the polyplex. For example, upon mixing the DNA with the cationic polymer, the polyplex comprising DNA and the cationic polymer may grow in size (e.g., particle diameter may increase over time), and addition of the polyplex stabilizing agent may prevent or dramatically retard further growth of the polyplex. The predetermined time subsequent to mixing together the first solution and the second solution may thus be selected based on a desired size of the polyplex for a particular application. In some embodiments, the desired size may comprise a range between 400 and 1000 nanometers in diameter, although other size ranges are encompassed by the present disclosure depending on the application (e.g., less than 400 nm in diameter, or greater than 1000 nm in diameter). The predetermined time may be a function of at least a concentration of the first solution and the second solution. For example, higher concentrations of the first solution and the second solution, when mixed, may lead to more rapid growth of the polyplex, as compared to less rapid growth of the polyplex when lower concentrations of the first solution and the second solution are mixed. In some embodiments the cationic polymer may be polyethyleneimine (PEI), although other cationic polymers mentioned herein can be used without departing from the scope of this disclosure. In some embodiments, the polyplex stabilizing agent may be human serum albumin (HSA), which may in some examples comprise recombinant HSA.

Also disclosed herein is a method, comprising providing a PEI solution at a first concentration and providing a DNA solution at a second concentration. The method may further comprise adding a first predetermined amount of the PEI solution to a second predetermined amount of the DNA solution, and mixing to obtain a PEI-DNA complex in solution. After a first predetermined duration, the method may further comprise adding a third predetermined amount of a PEI-DNA transfection complex stabilizing agent to the PEI-DNA complex in solution to obtain a stabilized PEI-DNA complex. After a second predetermination subsequent to the first predetermined duration, the method may further comprise transfecting a population of cells with the stabilized PEI-DNA complex.

In an embodiment of the method, the first predetermined duration may be a function of the first concentration and the second concentration. For example, the first predetermined duration may be lesser when the first concentration and the second concentration are higher, and the first predetermined duration may be greater when the first concentration and the second concentration are lower. The first predetermined duration may be based on a desired size of the stabilized PEI-DNA complex, and the desired size may be between 400 and 1000 nanometers in diameter in some embodiments. For example, the desired size may be between 400 and 1000 nanometers when the DNA solution comprises a plurality of DNA transfer plasmids that include one or more genes for synthesis of one or more viral proteins. As one example of such DNA transfer plasmids, the one or more genes may include genes corresponding to at least a portion of a lentiviral genome. In another example, the one or more genes may include genes corresponding to at least a portion of an adeno-associated viral genome.

In an embodiment of the method, the population of cells may comprise mammalian cells, such as HEK 293 suspension cells. Other mammalian cell types within the scope of this disclosure include but are not limited to HeLa, U2OS, A549, HT1080, CAD, P19, NIH 3T3, L929, N2a, recombinant Chinese hamster ovary (CHO), MCF-7, Y79, SO-Rb50, Hep G2, DUKX-X11, J558L, and/or baby hamster kidney (BHK) cells.

The stabilized PEI-DNA complex may be kept unfrozen in some examples prior to transfecting the population of cells. When the PEI-DNA complex is not frozen, the second predetermined duration may be between one minute and eighteen hours after the addition of the PEI-DNA transfection complex stabilizing agent. For example, the second predetermined duration may be between 1-2 minutes, or between 1-10 minutes, or between 10-30 minutes, or between 30-60 minutes, or between 1-2 hours, or between 2-3 hours, or between 3-4 hours, or between 4-5 hours, or between 5-6 hours, or between 6-7 hours, or between 7-8 hours, or between 8-9 hours, or between 9-10 hours, or between 10-11 hours, or between 11-12 hours, or between 12-13 hours, or between 13-14 hours, or between 14-15 hours, or between 15-16 hours, or between 16-17 hours, or between 17-18 hours. In a particular embodiment, the second predetermined duration may be greater than two minutes, but less than two hours.

In an embodiment of the method, the PEI-DNA transfection complex stabilizing agent may be non-recombinant HSA, recombinant HSA or a combination thereof. For example, the recombinant HSA may in some examples be purified *Pichia pastoris*, although other organisms may be used without departing from the scope of this disclosure. Examples include but are not limited to *Saccharomyces cerevisiae, Hansenula polymorpha, Kluyveromyces lactis*, etc. In some embodiments, the organism is *P. pastoris*, or *S. cerevisiae*. Also disclosed herein is a system for producing polymer-DNA nanoparticles of a defined size (e.g., within a defined size range). The system may include a polymer solution at a first concentration in a polymer chamber (e.g., tube, beaker, container, vessel, etc., optionally sealable), and a DNA solution at a second concentration in a DNA chamber (e.g., tube, beaker, container, vessel, etc., optionally sealable). The system may further include a mixing chamber (e.g., tube, beaker, container, vessel, etc., optionally sealable). The mixing chamber may be selectively fluidically coupled to the polymer chamber via a first connection line (e.g., tube, pipe, cylinder, hose, conduit, duct, etc.), and selectively fluidically coupled to the DNA chamber via a second connection line (e.g., tube, pipe, cylinder, hose, conduit, duct, etc.). The system may further include a first pump (e.g., positive displacement, centrifugal, or axial-flow) coupled to the first connection line between the polymer chamber and the mixing chamber, and a second pump (e.g., positive displacement, centrifugal, or axial-flow) coupled to the second connection between the DNA chamber and the mixing chamber. The system may further include a first valve (e.g., solenoid valve, pneumatically actuated valve, pressure-actuated valve, etc.) coupled to the first connection line and positioned between the first pump and the mixing chamber, and a second valve (e.g., solenoid valve, pneumatically actuated valve, pressure-actuated valve, etc.) coupled to the second connection line and positioned between the second pump and the mixing chamber. The system may further include a quenching chamber that receives fluid flow from the mixing chamber via a third connection line, where the quenching chamber includes a quenching agent at a third concentration. The system may further include a controller. The controller may store instructions in non-transitory memory that, when executed, cause the controller to control one or more of the first pump, the second pump, the first valve, and the second valve to route the polymer solution to the mixing chamber at a first flow rate and to simultaneously route the DNA solution to the mixing chamber at a second flow rate in order to provide a polymer-DNA complex within the mixing chamber that is then routed to the quenching chamber. In embodiments, the concentration of the polymer solution and the concentration of the DNA solution may be the same. In other examples, the concentration of the polymer solution and the concentration of the DNA solution may be different. In examples, the first and second flow rates may be the same (e.g., when the polymer solution concentration and the DNA solution concentration are the same), or may be different (e.g., when the polymer solution concentration and the DNA solution concentration are different).

In an embodiment of the system, the quenching agent may be one or more of non-recombinant HSA, recombinant HSA, and/or other albumin. The polymer solution, in some embodiments, may comprise PEI, and/or other cationic polymers as disclosed herein.

In an embodiment of the system, the mixing chamber may be of a defined geometry so as to encourage consistent mixing and residence time of the polymer solution and the DNA solution as a function of the first flow rate and the second flow rate. For example, growth of the polymer-DNA complex may occur within the mixing chamber, and the growth may be a function of the mixing and residence time within the mixing chamber (and may further be a function of DNA concentration and polymer concentration). Growth of the polymer-DNA complex may be stabilized (e.g., further growth may be prevented or retarded) by the quenching agent upon the polymer-DNA complex being deposited (and mixed) in the quenching chamber, thereby providing the polymer-DNA complex of the defined size. In some examples, the defined size may be between 400 and 1000 nanometers in diameter, for some applications. For example, the defined size may be between 400 and 1000 nanometers in diameter when the DNA solution includes a plurality of transfer plasmids that include one or more genes for synthesis of viral proteins for the production of lentivirus or adeno-associated virus.

Also disclosed herein is a method for transfecting a population of cells with a reconstituted polymer-DNA transfection complex. The method may comprise mixing together a DNA solution at a first concentration with a polymer solution at a second concentration to obtain a polymer-DNA transfection complex in solution. The method may further comprise, after a first predetermined duration, stabilizing a size of the polymer-DNA transfection complex via a quenching agent to obtain a stabilized polymer-DNA transfection complex. Subsequently, the method may include adding one or more lyophilization agents to the stabilized polymer-DNA transfection complex and lyophilizing the stabilized polymer-DNA transfection complex to a powder. Then, at a later time, the method may include reconstituting the lyophilized stabilized polymer-DNA transfection complex to obtain the reconstituted polymer-DNA transfection complex, diluting the reconstituted polymer-DNA transfection complex into a transfection solution, and transfecting the population of cells with the reconstituted polymer-DNA transfection complex.

For such a method, the polymer may comprise a cationic polymer. In some embodiments the cationic polymer may be PEI or other cationic polymer herein disclosed. In some embodiments, the quenching agent may be HSA. In some embodiments, the DNA solution may further comprise a plurality of transfer plasmids that code for at least a portion of a viral genome. As a representative example, the viral genome may be a lentiviral genome. As another representative example, the viral genome may be an adeno-associated viral genome.

In some embodiments of such a method, the powder may be stored at 4° C., −20° C. or −80° C. until the later time. In some embodiments, the lyophilization agent may be one or more of mannitol and sucrose. In one example, the lyophilization agent may comprise both mannitol and sucrose, where mannitol may be at a concentration of 25-35 mg/mL (e.g., 30 mg/mL) and sucrose may be at a concentration of 15-25 mg/mL (e.g., 20 mg/mL). In another example, the lyophilization agent may comprise just mannitol at a concentration of 25-35 mg/mL (e.g., 30 mg/mL).

It may be understood that the methodology for lyophilizing a stabilized polymer-DNA transfection complex may be used with any of the methods and systems discussed herein, without departing from the scope of this disclosure.

II. Terms

In order to facilitate review of the various embodiments of this disclosure, the following explanations of specific terms are provided. These explanations are not intended to be limiting of the disclosure or provide definitions of any terms provided herein:

Agent: Any protein, nucleic acid molecule (including chemically modified nucleic acids), compound, small molecule, organic compound, inorganic compound, or other molecule of interest. Agent can include a therapeutic agent, a diagnostic agent, a pharmaceutical agent, stabilizing/quenching agent (e.g., polyplex stabilization agent) and/or a lyophilization agent. A therapeutic or pharmaceutical agent is one that alone or together with an additional compound induces the desired response (such as inducing a therapeutic or prophylactic effect when administered to a subject, including inhibiting or treating a particular disease or condition). A stabilizing agent is one which the desired response is to stabilize a condition or complex. In one example, a stabilizing agent is a polyplex stabilizing agent, such as HSA. A quenching agent is one which induces the desired response of quenching/stopping a reaction or process from occurring. With regard to HSA preventing further growth of a polyplex, and also substantially preventing degradation of the polyplex, in examples HSA as discussed herein can refer to both a stabilization agent and a quenching agent.

Cell culture: Any in vitro culture of cells. Included within this term are continuous cell lines (e.g., with an immortal phenotype), primary cell cultures, finite cell lines (e.g., non-transformed cells), and any other cell population maintained in vitro. "Cell culture medium" means a medium that can be used to cultivate cells.

Contacting: Placement in direct physical association, including both a solid and liquid form. Contacting an agent with a cell can occur in vitro by adding the agent to isolated cells or in vivo by administering the agent to a subject. Mixing a DNA solution and a cationic polymer solution as herein disclosed may comprise contacting the DNA solution with the cationic polymer solution. A cationic polymer-DNA polyplex may be contacted by a quenching agent, to prevent or retard further growth and/or to stabilize a size of the polyplex.

Control: A sample or standard used for comparison with a test sample. In some embodiments, the control is a historical control or standard value (e.g., a previously tested control sample or group of samples that represent baseline or normal values (e.g., expression values), such as baseline or normal values of a particular gene or gene product in a subject having not received a particular therapeutic agent. A control represents an untreated sample (e.g., absence of a particular agent) for comparison with a treated sample (e.g., treated with the particular agent).

Gene Therapy: Delivery of DNA encoding a gene of interest into a cell, with the intention of treating a disease or to endow a cell or organism with capabilities not otherwise present in the natural state. Gene therapy via a virus (e.g., gammaretrovirus, lentivirus, adenovirus, and adeno-associated viruses) relies on the ability of viruses to enter into and deliver genetic material to cells. Gammaretroviruses and lentiviruses are subtypes of retroviruses, which contain an RNA genome that is converted to DNA in the transduced cell by a virally encoded enzyme called reverse transcriptase. The basic genes needed for retroviral and lentiviral survival are the gag, pol, and env genes; gag encodes structural proteins, pol encodes enzymes required for reverse transcription and integration into the host cell genome, and env encodes the viral envelope glycoprotein.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Serum Albumin (HSA): The most abundant protein in human plasma with a molecular weight of 66,437 Da (based on amino acid composition). Commercial preparations contain varying degrees of post-translational modifications and genetic variants with molecular weight components mainly in the range of 66,437 to 66,600 Da. HSA can be produced by using a cold alcohol fractionation process derived from the traditional Cohn method as well as heat shock methods. In examples, HSA can be produced recombinantly.

Increase or upregulate: To enhance the quality, amount, or strength of something. In one example, an agent increases the activity of a molecule disclosed herein, for example relative to an absence of the agent. In a particular example, an agent increases the activity or expression of a molecule by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such increases can be measured using the methods disclosed herein.

In some examples, an increase in expression refers to an increase in a gene product or activity of a gene product. A gene product can be RNA (such as mRNA, rRNA, tRNA, and structural RNA) or protein.

Gene upregulation includes any detectable increase in the production of a gene product. In certain examples, production of a gene product increases by at least 2-fold, for example at least 3-fold or at least 4-fold responsive to administration of an agent, as compared to a control (such an amount of gene expression in a cell that has not been exposed to the agent). Detecting or measuring expression of a molecule includes quantifying the amount of the gene, gene product or modulator thereof present in a sample. Quantification can be either numerical or relative. Detecting expression of the gene, gene product or modulators thereof can be achieved using any method known in the art or described herein, such as by measuring nucleic acids by PCR (such as quantitative RT-PCR) and proteins by ELISA. The level of expression in either a qualitative or quantitative manner can include detection of a nucleic acid or protein. Exemplary methods include microarray analysis, RT-PCR, Northern blot, Western blot, and mass spectrometry.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" may be understood to have been purified by standard purification methods. The term also embraces nucleic acid molecules and proteins prepared by recombinant expression in a host cell as well as chemically synthesized nucleic acid molecules and proteins.

Optional: "Optional" or "optionally" means that the subsequently described event or circumstance can but need not occur, and that the description includes instances where said event or circumstance occurs and instances where it does not.

PEI: a polymer with repeating unit composed of the amine group and two carbon aliphatic $CH_2CH_2$ spacer. Linear polyethyleneimines contain all secondary amines, in contrast to branched PEIs which contain primary, secondary and tertiary amino groups. Totally branched, dendrimeric forms have also been reported. PEI is produced on industrial scale and finds many applications usually derived from its polycationic character. The chemical structure for PEI is $(C_2H_5N)_n$. In embodiments herein, PEI is used a transfection agent. PEI condenses DNA into positively charged particles, which bind to anionic cell surface residues and are brought into the cell via endocytosis. Once inside the cell, protonation of the amines results in an influx of counter-ions and a lowering of the osmotic potential. Osmotic swelling results and bursts the vesicle releasing the polymer-DNA complex (polyplex) into the cytoplasm. The DNA is released from the endosomes into the cytoplasm by a "proton sponge" mechanism, thereby allowing nuclear transport for subsequent transcription. The size, charge, and association of the PEI-DNA complexes impact endocytosis/phagocytosis as well as intracellular unpackaging and transport. Factors affecting the physical and biological properties of PEI based polyplex include but are not limited to, molecular weight (e.g., of PEI and DNA), any chemical modifications to PEI (e.g., branching modifications) or DNA, buffer content for generating the PEI-DNA complex, complex stability, complex size, surface charge of DNA, complexation efficiency, transfection efficiency of the complex, complex aggregation, cytotoxicity issues, mechanism of transfection complex uptake, immunostimulation issues, circulation half-life, interaction with serum protein, biological activity, opsonization, and excretion. PEI Pro (PolyPlus) is a linear PEI with proprietary molecular weight. It is a chemically defined, fully characterized product available in GMP grade and may be used in some embodiments.

The term "PEI-DNA" complex is used herein to describe a composition in which PEI is bound to DNA.

Polyplex solution: A solution that contains DNA and a cationic polymer, such as a solution containing a PEI-DNA complex.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered solely by addition, substitution, or deletion of a portion of a natural nucleic acid molecule or protein. For example, a "recombinant protein" is a protein or peptide that is not synthesized in animals or humans. Non-limiting examples include recombinant HSA.

Transfection: The introduction of foreign DNA into eukaryotic cells. Transfection may be accomplished by methods disclosed herein and those known to the art including, but not limited, to calcium phosphate-DNA co-precipitation, DEAE-dextran-mediated transfection, polybrene-mediated transfection, electroporation, microinjection, liposome fusion, lipofection, protoplast fusion, retroviral infection, cationic-based transfection, and biolistics.

The term "during transfection" means during or after transfection. A "transfection reagent" refers to a substance or mixture of substances that binds to a molecule and facilitates the delivery of the molecule to the cell and/or absorption of the molecule by the cell, for example, a cationic lipid, a charged polymer, or a peptide penetrating into the cell. Reagent-based transfection refers to transfection carried out using a transfection reagent. The term "transfection medium" is to refer to a medium that can be used for transfection.

Under conditions sufficient to: A phrase that is used to describe any environment that permits the desired activity. In one example, it includes conditions sufficient to induce uptake of a molecule, such as transfection.

Vector: Nucleic acid molecules that transfer nucleic acid (e.g., DNA) segment(s) from one cell to another. For example, vectors include, but are not limited to, viral particles, plasmids, transposons, etc. A vaccine vector can be a virus, bacterium, or other microbe, or a nucleic acid, used to deliver an antigen or a gene for an antigen, as part of a vaccine. A nucleic acid vector is a nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. A retroviral vector is used in reference to modified retroviruses used as vectors for introduction of nucleic acid into cells. The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

In some examples, the vector is a LVV. Clinically, LVVs may be used for gene therapy for reasons including, but not limited to, the ability to introduce large regions of genetic material (e.g., >9 kb) into host genomes, the ability of LVVs to transduce dividing and non-dividing cells, and the ability to stably integrate into the genome of a target cell to provide lifelong correction to that cell and its progeny. In other examples, the vector is an AAV.

Virus: A microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. Lentiviruses are a type of retrovirus that can infect both dividing and non-dividing cells because their preintegration complex (virus "shell") can get through the intact membrane of the nucleus of the target cell. Lentivirus-based cell and gene therapies have been approved by the US Food and Drug Administration and by the European Medicines Agency, and additional lentiviral-based cellular therapies are expected to be approved in the future.

III. Systems and Methods of Use i. Methods for Providing a Transfection Complex within a Predetermined Size Range for Optimizing Viral Vector Production in Suspension Cell Culture Viral vector production processes include transfecting a particular cell type with a plurality of transfer plasmids that code for genes that, when expressed in the particular cell type, ultimately produce the desired viral particles which can then be harvested for use in clinical and/or research settings. In one example, the transfection process includes combining the plurality of plasmids with a cationic polymer (e.g., PEI), thereby condensing the DNA plasmids into positively charged particles that bind to anionic cell surfaces. Once bound, the transfection complex (e.g., PEI-DNA transfection complex) may be endocytosed by the cells, and the DNA (e.g., plurality of transfer plasmids) may be released into the cytoplasm of the cells. While the process may result in efficient viral vector production on small scale, there are challenges to scaling up the process to scales appropriate for, as an example, gene therapy methods.

Disclosed herein, viral vector titer at harvest can be sensitive to a hold time, also referred to herein as complexation time, defined as a time between initial mixing of the polymer and the DNA and when the polymer-DNA transfection complex is transfected into the desired cell type. For example, disclosed herein, the longer the polymer-DNA hold time, the lower the viral vector titer may be at harvest. This effect may be concentration dependent, with higher concentration polymer-DNA solutions requiring ever shorter hold times in order to produce acceptable viral vector titer at harvest. As a specific example, at a concentration necessary for the polymer-DNA complex to be a 3% v/v addition to a HEK293 cell culture, optimal hold time may be two minutes or less. This short hold time creates a significant manufacturing challenge as hold times of two minutes or less may be challenging if not impossible to achieve at large production scales. Specifically, as the suspension platform is scaled up towards the target commercial scale, the master mix volume that includes the polymer and DNA may reach a volume that is too large to mix and introduce to the suspension culture fast enough to achieve adequate transfection, and thus there is a need to ensure the transfection complex introduced to at-scale bioreactor volumes is properly formed.

Accordingly, discussed herein is a method comprising, providing a PEI solution at a first concentration and a DNA solution at a second concentration, adding a first predetermined amount of the PEI solution to a second predetermined amount of the DNA solution and mixing to obtain a PEI-DNA complex in solution. In some embodiments, after a first predetermined duration, the method includes adding a third predetermined amount of a PEI-DNA transfection complex stabilizing agent to the PEI-DNA solution to obtain a stabilized PEI-DNA complex, and after a second predetermined duration subsequent to the first predetermined duration, the method includes transfecting a population of cells with the stabilized PEI-DNA complex. The methodology arrests growth of the PEI-DNA complex at a desired size or optimal size for the particular application, to facilitate efficient transfection, thereby improving yields of viral vector titer at harvest. Via the ability to stabilize the size of the PEI-DNA transfection complex, larger volumes of master mix (e.g., solutions where DNA and polymer are mixed together) may be generated, and the second predetermined duration may be extend to timeframes that enable efficient transfection of at-scale bioreactor volumes.

Discussed herein and in particular with regard to the Example 3 below, the second predetermined duration can be extended to timeframes up to 18 hours post-addition of the PEI-DNA transfection complex stabilizing agent to stabilize the PEI-DNA transfection complex (refer to FIG. 7C), and still produce a measureable amount, and in some examples an acceptable amount, of viral vector titer at harvest. Discussed herein, in one example, the second predetermined duration comprises a range between 2 minutes and 18 hours. In another example, the second predetermined duration comprises a range between 2 minutes and one hour. In another example, the second predetermined duration comprises a range between 2 minutes and 2 hours. In another example, the second predetermined duration comprises a range between 10 minutes and one hour. In another example, the second predetermined duration comprises a range between 10 minutes and 2 hours. In another example, the second predetermined duration comprises a range between 30 minutes and one hour. In another example, the second predetermined duration comprises a range between 30 minutes and 2 hours. In another example, the second predetermined duration comprises a range between 2 hours and 4 hours. In another example, the second predetermined duration comprises a range between 3 hours and 5 hours. In another example, the second predetermined duration comprises a range between 4 hours and 6 hours. In another example, the second predetermined duration comprises a range between 6 hours and 12 hours. In another example, the second predetermined duration comprises a range between 4 hours and 8 hours. In another example, the second predetermined range comprises a range between 8 hours and 18 hours. In another example, the second predetermined range comprises a range up to about 18 hours, such as about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours or about 18 hours.

In some embodiments, the PEI-DNA transfection complex stabilizing agent comprises any agent that retards or prevents further growth of a PEI-DNA complex. As one example, the agent may be HSA, such as non-recombinant HSA, recombinant HSA or a combination thereof. As another additional or alternative example, the agent may be a molecule (e.g., peptide, protein, ribonucleic acid, deoxyribonucleic acid, small molecule, etc.) that is associated with HSA (e.g., included in a composition comprising HSA). For example, the agent may be HSA plus the molecule in an embodiment, or in other embodiments the agent may be the molecule purified or isolated from the HSA. In another example, the PEI-DNA transfection complex stabilizing agent comprises recombinantly produced HSA. In a representative example, the recombinantly produced HSA may be expressed and purified from *P. pastoris*. In an example where the PEI-DNA transfection complex stabilizing agent comprises recombinantly produced HSA, the agent can be the recombinantly produced HSA itself, or may additionally or alternatively be a molecule (e.g., peptide, protein, ribonucleic acid, deoxyribonucleic acid, small molecule, etc.) that is associated with the recombinantly produced HSA (e.g., included in a composition comprising HSA). In an embodiment, the agent comprises recombinantly produced HSA plus the molecule, or in other embodiments, the agent may be the molecule purified or isolated from the HSA.

ii. Methods for Stabilizing a Size of a Polyplex.

Cationic polymer based reagents can be particularly helpful in transfecting cells that exhibit low efficiency when transfected using lipid based reagents. When used at optimal concentrations, these reagents exhibit low toxicity. Polymer based transfection reagents can be used to transfect suspension cultures, primary cells, a variety of eukaryotic cells lines, adherent cells, etc. Many natural and synthetic cationic polymer based transfection reagents are currently available. However, transfection efficacy, and in turn, expression of desired genes, may in some examples be adversely impacted by a non-optimal size (e.g., too large or too small) of a transfection complex that includes a cationic polymer and DNA (e.g., a DNA plasmid or a plurality of DNA plasmids). Disclosed herein is a method for stabilizing a size of a polyplex in order to provide a transfection complex of an optimal size for transfection, thereby improving downstream gene expression stemming from the transfection procedure. In an example, the method comprises mixing together a first solution comprising deoxyribonucleic acid (DNA) with a second solution comprising a cationic polymer to obtain a polyplex solution, and at a predetermined time subsequent to mixing together the first solution and the second solution, adding a polyplex stabilizing agent to the polyplex solution to stabilize the size of the polyplex.

The cationic polymer may in some examples comprise PEI, but in other embodiments, the cationic polymer may be different. In some embodiments, PEI Pro is the cationic polymer. Exemplary cationic polymers that can be used include but are not limited to histones, poly-L-lysine, polyamidoamine dendrimers, protamine and/or any combination thereof, and the like.

The appropriate size of the polyplex may be different for different applications. In some examples, the appropriate size of the polyplex may comprise a size range between 200 and 1500 nanometers in diameter, including, but not limited to about 200, 300, 400, 500, 600, 700, 800, 900, 1000, 1100, 1200, 1300, 1400 or 1500 nanometers. In another example, the size range may be between 300 and 500 nanometers. In another example, the size range may be between 400 and 1000 nanometers. In another example, the size range may be between 400 and 800 nanometers. In another example, the size range may be between 500 and 1000 nanometers. In another example, the size range may be between 500 and 900 nanometers. In another example, the size range may be between 500 and 800 nanometers. In another example, the size range may be between 500 and 700 nanometers. In another example, the size range may be between 700 and 1500 nanometers. In another example, the size range may be between 800 and 1400 nanometers. It may be understood that the size ranges discussed relate to hydrodynamic diameter of the polyplex.

In order to determine the appropriate size of the polyplex for a particular application, a variety of different polyplex sizes may be generated and transfected into a desired cell type, and ensuing gene expression may be monitored by methods disclosed herein and known in the art. Gene expression levels, as monitored for example via a reporter (e.g., fluorescent reporter, bioluminescent reporter), viral vector titer at harvest, protein expression quantity monitored via staining protocols, immunofluorescence staining, log(vector genomes), etc., within a desired range may be correlated with a particular polyplex size range. Polyplex size (e.g., nanoparticle size), may be determined via dynamic light scattering methodology, as a representative example. Polyplexes of a particular size corresponding to the gene expression within a desired range may be subsequently generated for transfecting the particular cell type, via utilizing the methodology for stabilizing a polyplex discussed herein, to achieve optimal gene expression for the particular application.

In a representative example of the method for stabilizing the size of a polyplex, the first solution comprising DNA may include a plurality of transfer plasmids that together encode for a replication incompetent lentivirus, and the cationic polymer for the second solution may be PEI. The polyplex stabilizing agent can comprise HSA. In such an example, the predetermined time following initiation of polyplex formation and before stabilization can be selected to provide the polyplex (e.g., transfection complex of PEI and the plurality of DNA plasmids encoding for at least a portion of the lentiviral genome) at a desired size, which may comprise a range between 400 and 1000 nanometers in hydrodynamic diameter. The predetermined time may be a function of concentration of each of the first solution (e.g., DNA concentration) and the second solution (e.g., cationic polymer concentration). For example, for a given desired size of the polyplex, the predetermined time may be greater when the concentration of each of the first solution and the second solution is lesser, whereas the predetermined time may be lesser when the concentration of each of the first solution and the second solution is greater. The mixing of the first solution and the second solution may be conducted at a predetermined temperature, and/or a predetermined pH, to facilitate the formation of the polyplex prior to addition of the polyplex stabilizing agent. In some examples, the methodology may include controlling a rate at which the first solution is mixed with the second solution. As one example, the rate may be controlled via a speed at which the first solution and the second solution are mixed together, for example by controlling a speed of a stir bar or other mixing device that mixes the first solution and the second solution. In other examples, the mixing of the first solution and the second solution may be via an automated mixing system, an example of which is discussed in greater detail below.

In such an example, once the polyplex is stabilized at the desired size, the polyplex can be used to transfect a desired population of cells. The desired population of cells may comprise cells grown in suspension, for example in a bioreactor. The transfection may occur at a time subsequent to stabilization of the polyplex, within a range of about 1 minute to 18 hours, such as between 2 hours to not more than about 18 hours. Thus, stabilization of the polyplex via the polyplex stabilizing agent provides a timeframe for which the desired cells are transfected to be extended up to 18 hours in some examples. It may be understood that there may be a gradual decay in transfection efficacy (and hence LVV titer at harvest) between two hours and 18 hours subsequent to stabilization of the polyplex. For example, viral vector at harvest may be lower when the cells are transfected at 12 hours post polyplex stabilization as compared to when the cells are transfected at 2 hours or less post polyplex stabilization.

While the above representative example focused on use of the methodology for stabilizing a polyplex for use with lentivirus production, similar methodology may be used for production of other viral vectors. Examples include but are not limited to adenoviruses, adeno-associated viruses, and standard retroviruses that can infect only mitotically active cell types.

iii. System for Producing Polymer-DNA Nanoparticles of a Defined Size.

There may be numerous factors involved in the generation of transfection complexes comprised of a polymer (e.g., PEI) and nucleic acid. Briefly, in terms of the nucleic acid for which transfection is desired, considerations may include, but are not limited to, molecular weight, presence or absence of any modifications, surface charge, etc. In terms of the polymer, considerations may include but are not limited to molecular weight and branching modifications, among others. In terms of the transfection complex, or polyplex itself, considerations may include, but are not limited to, selection of buffer in which the complex is generated and related parameters such as pH, temperature, mixing rate, etc. In terms of optimizing transfection efficacy, and thereby, optimization of the desired level of gene expression stemming from the transfection, considerations may include, but are not limited to, complex stability, size of the complex, aggregation, cytotoxicity, etc. Thus, in order to reliably produce transfection complexes of a size that is within a predetermined size range as discussed above, it is herein recognized that automation of the transfection complex production process may be desirable, particularly for large scale applications (e.g., bioreactor).

Figure 8A:
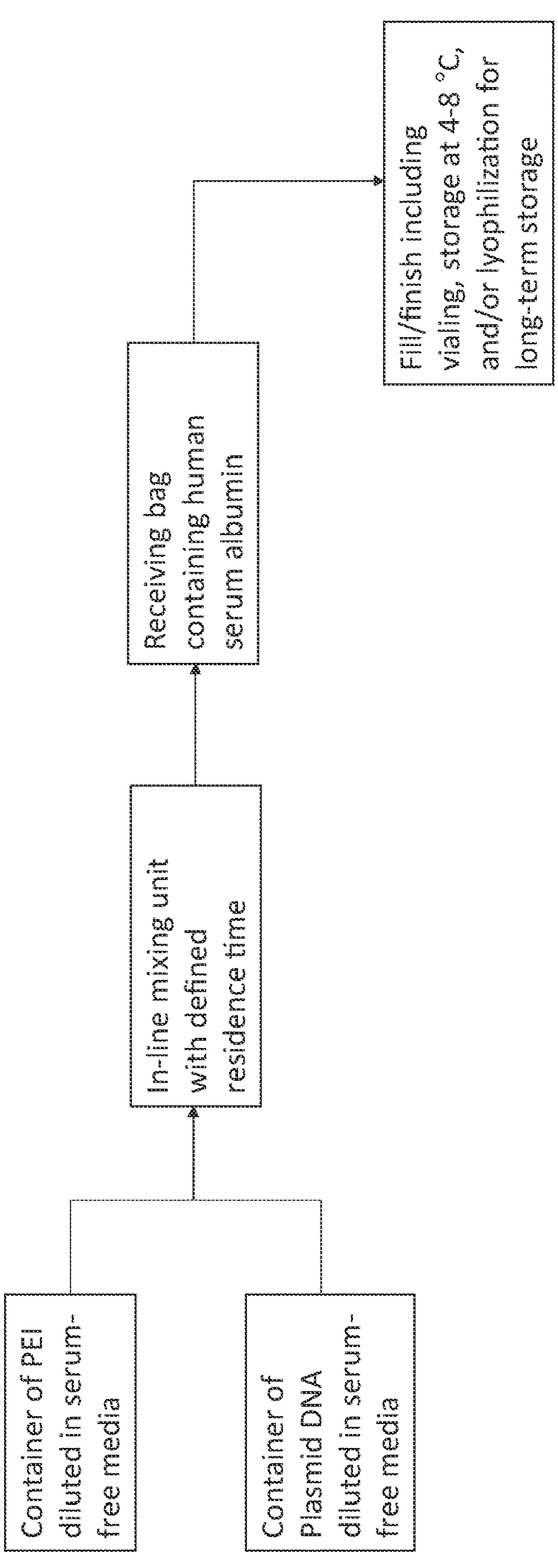
FIG. 8A is a high-level flowchart of an exemplary polymer-DNA complex design in accordance with embodiments provided herein.

Accordingly, disclosed herein is a system for producing polymer-DNA nanoparticles of a defined size. FIG. 8A provides an exemplary design in accordance with embodiments herein. Briefly, in one example a system includes a first container of PEI diluted in serum free media, and a second container of plasmid DNA diluted in serum-free media. The system includes an in-line mixing unit with a defined residence time for fluid being routed therethrough. The defined residence time may be a function of a rate at which fluids are routed to the in-line mixing unit, in some examples. The in-line mixing unit may be fluidically coupled to each of the first container and second container, such that the in-line mixing unit may receive a fluid flow from each of the first container and the second container simultaneously. The containers and the in-line mixing unit may be fluidically coupled via a connection line (e.g., tubing, hose, pipe, etc.). Specifically, the in-line mixing unit may receive solutions from each of the first container and the second container, and may mix the solutions within the in-line mixing unit such that the solutions are mixed and in contact with one another for the defined residence time. The defined residence time may further be a function of one or more of a geometry (e.g., t-shaped), dimensions (e.g., diameter(s) of tubing or channels associated with the in-line mixing unit), or other characteristics of the in-line mixing unit. The system may further include a receiving container containing a quenching agent (e.g., HSA). The receiving bag or container may be fluidically coupled to the in-line mixing unit via a connection line (e.g., tubing, hose, etc.) and may receive a fluid flow from the in-line mixing unit. It may be understood that the quenching agent may stabilize a PEI-DNA transfection complex generated within the in-line mixing unit, upon the PEI-DNA transfection complex being deposited into the receiving container. Once stabilized by the quenching agent, the solutions containing the stabilized PEI-DNA transfection complex may be aliquoted into vials or other acceptable containers, and stored, for example, at 4-8° C. and/or lyophilized for longer term storage.

In some embodiments, an exemplary system includes two separate chambers for the polymer solution and the DNA solution. The two chambers can include means for stirring the different solutions (e.g., magnetic stir bar, overhead stir bar, and the like). In some examples, the system may include a plurality of pumps (e.g., two) that route the DNA solution through one connecting line to a mixing chamber, and which similarly route the polymer solution through another connection line to the mixing chamber. While the use of pumps is disclosed, it is also within the scope of this disclosure that gravity be used in addition to or in lieu of pumps. Similar to that discussed above, the connecting line(s) may comprise hoses, tubing, etc. A flow control device, for example a one-way or two-way valve, continuously variable valve, etc., may be included in each of the connection lines between the pumps and the mixing chamber, and may be used to control or modify flow rates at which the DNA solution and the polymer solution is delivered to the mixing chamber. In some examples, the flow control devices may be electrically actuatable, whereas in other examples the flow control devices may be manually actuatable. For automation of such a system, a controller may be included, programmable via an operator, which may include non-transitory instructions that, when executed, cause the controller to control at least the pumps and the flow control devices to control flow rates at which each of the DNA solution and the polymer solution are routed to the mixing chamber.

In such a system, it may be understood that the formation of the polymer-DNA transfection complex may be initiated in the mixing chamber. The mixing chamber may thus be of a defined geometry to encourage adequate mixing of the two solutions within the mixing chamber. As discussed herein, once initiated, a polymer-DNA complex may grow in size (e.g., particle diameter) over time. Accordingly, the mixing chamber may be designed such that there is a defined residence time for the growing transfection complex prior to the transfection complex exiting the mixing chamber. The residence time may be a function of flow rates at which the DNA and polymer solutions are routed to the mixing chamber, mixing chamber diameter, mixing chamber shape, etc. In this way, transfection complexes formed within the mixing chamber may reach a defined size (e.g., within a predetermined size range) just prior to exiting the mixing chamber, resulting in consistent production of transfection complexes of a desired size.

Upon exiting the mixing chamber, the transfection complexes of the desired size may be routed to quenching chamber. The quenching chamber may include a quenching solution that comprises a quenching agent. In some examples, the quenching agent may be non-recombinant HSA. In other additional or alternative examples the quenching agent may be recombinantly produced HSA. As one particular example where the quenching agent is recombinantly produced HSA, the HSA may be produced in *P. pastoris*. In still other additional or alternative examples, the quenching agent may be a molecule (e.g., peptide, protein, small molecule, deoxyribonucleic acid, ribonucleic acid, etc.) associated with the recombinant or non-recombinant HSA. In some examples the molecule may be purified away from the recombinant or non-recombinant HSA, while in other examples the molecule and HSA may together comprise the quenching agent. The quenching chamber may, similar to the DNA chamber and the polymer chamber, include a means for mixing the solution, such that the extent of mixing may be controlled. In some examples, the mixing means in each of the DNA chamber, polymer chamber, and quenching chamber may be controllable via the controller.

Upon being deposited in the quenching chamber, the growth of the transfection complex may be arrested. In this way, transfection complexes of a defined size may be reliably and consistently produced, which may be particularly advantageous for large scale applications (e.g., bioreactor applications). The desired size of the transfection complex may be different for different applications. In some examples, the desired size of the polyplex may comprise a size range between 200 and 1500 nanometers, including, but not limited to about 200, 300, 400, 500, 600, 700, 800, 900, 1000, 1100, 1200, 1300, 1400 or 1500 nanometers. In another example, the size range may be between 300 and 500 nanometers. In another example, the size range may be between 400 and 1000 nanometers. In another example, the size range may be between 400 and 800 nanometers. In another example, the size range may be between 400 and 800 nanometers. In another example, the size range may be between 500 and 1000 nanometers. In another example, the size range may be between 500 and 900 nanometers. In another example, the size range may be between 500 and 800 nanometers. In another example, the size range may be between 500 and 700 nanometers. In another example, the size range may be between 700 and 1500 nanometers. In another example, the size range may be between 800 and 1400 nanometers. In another example, the size range may be between 900 and 1300 nanometers. In another example, the size range may be between 1000 and 1200 nanometers. It may be understood that the size ranges mentioned above relate to hydrodynamic diameter of the transfection complex.

Following the stabilization of the transfection complex, the solution containing the transfection complex may be held for a variable amount of time prior to performing transfection. In other words, the stabilization of the transfection complex via the quenching agent may increase a timeframe in which transfection of a particular cell type may be conducted, as compared to other examples where the quenching agent were not used. This may be particularly advantageous for large scale applications (e.g., bioreactor applications), where transfection procedures may occur over a longer time period (e.g., minutes to hours) as compared to smaller scale applications. It may be understood that for performing the transfection, the transfection complexes in the quenching solution may first be diluted into transfection media.

Variables that may be considered for use of such a system that have not yet been discussed may include, but are not limited to, concentration of the DNA solution within the DNA chamber; concentration of polymer solution in the polymer chamber; concentration of the quenching agent in the quenching chamber; pH of each of the DNA solution, components of the polymer solution and quenching solution; ionic strength of each of the DNA solution, polymer solution and quenching solution; temperature of each of the solutions and components of the system, etc.

In a representative example, such a system may be used for the production of viral vectors in large scale applications. Examples include, but are not limited to, adenoviruses, adeno-associated viruses, and standard retroviruses that can infect only mitotically active cell types.

Figure 8B:
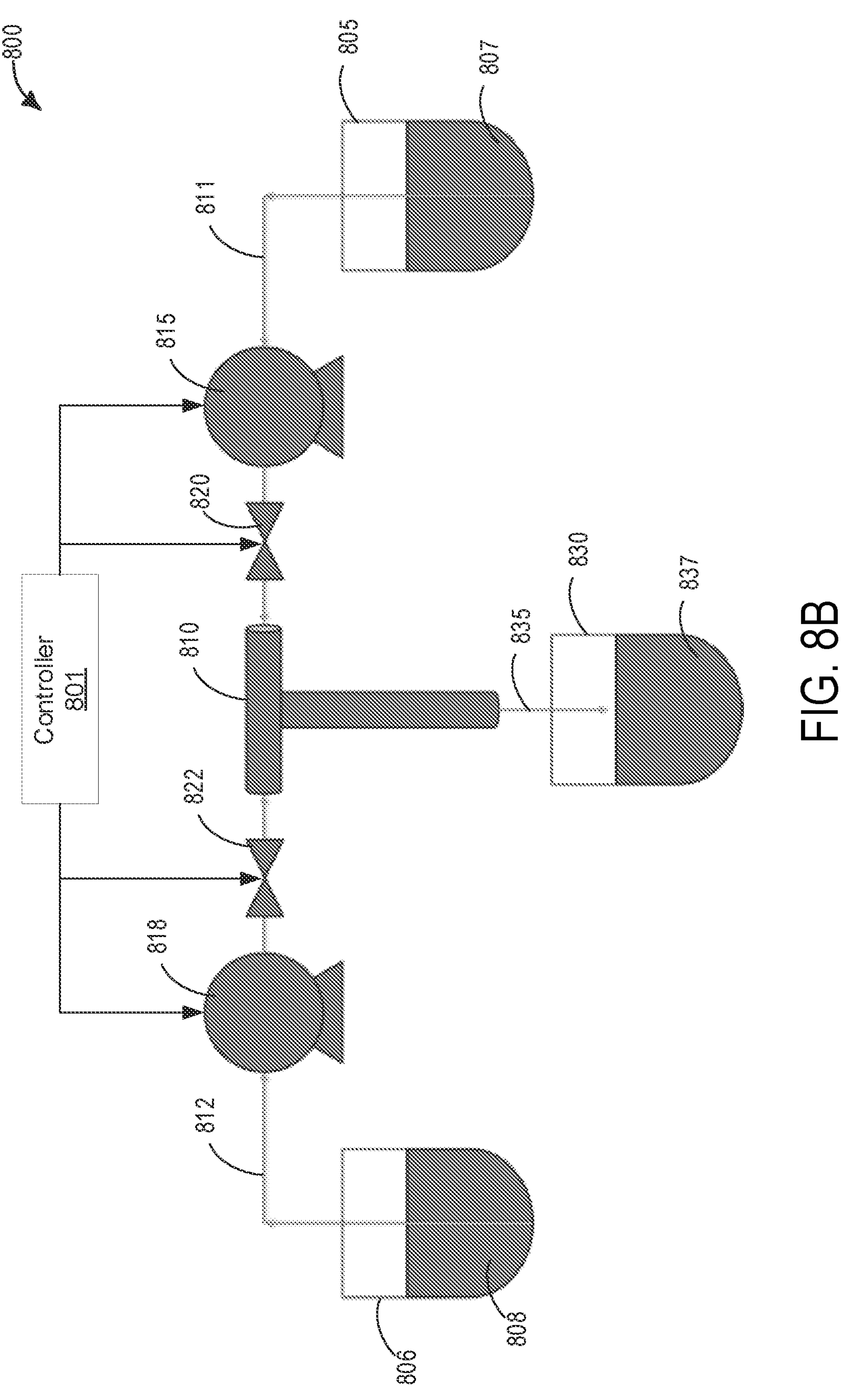
FIG. 8B is a schematic of an automated system for providing polymer-DNA nanoparticles of a predetermined particle diameter in accordance with embodiments provided herein.

Referring to FIG. 8B, exemplary system 800 is for preparing polymer-DNA transfection complexes of a predetermined size in accordance with embodiments disclosed herein. As illustrated, system 800 includes a polymer chamber 805 and a DNA chamber 806. The polymer chamber 805 includes a polymer solution 807 at a first concentration, and the DNA chamber includes a DNA solution 808 at a second concentration. In some examples, the polymer solution 807 may comprise a cationic polymer, including but not limited to PEI. In some examples, the DNA solution may comprise a plurality of plasmids that each encode for viral proteins that, when transfected into a cell, produce replication-incompetent virus particles, however in other examples the DNA solution may comprise other DNA plasmids without departing from the scope of this disclosure. In one example, the plurality of plasmids may encode for replication-incompetent lentiviral particles.

System 800 includes mixing chamber 810. The mixing chamber is configured to receive the polymer solution 807 via first connection line 811, and is additionally configured to receive the DNA solution 808 via second connection line 812. In some examples, a connection line is a hose/tubing. A first pump 815 is coupled to the first connection line 811 at a position between the polymer chamber 807 and the mixing chamber 810. A second pump 818 is coupled to the second connection line 812 at a position between the DNA chamber 806 and the mixing chamber 810. Furthermore, a first fluid control device 820 is coupled to the first connection line 811 between the first pump 815 and the mixing chamber 810, and a second fluid control device 822 is coupled to the second connection line 812 between the second pump 818 and the mixing chamber 810. Each of the first fluid control device and the second fluid control device may comprise one-way or two-way valves, as an example. In some examples, one or more of the first fluid control device 820 and the second fluid control device 822 may include continuously variable valves. The first fluid control device 820 and the second fluid control device 822 may be actuated, for example via a solenoid actuator, pressure-based actuator, vacuum-actuated, etc.

System 800 also includes a quenching chamber 830. Quenching chamber 830 receives fluid flow from the mixing chamber via third connection line 835. Quenching chamber 830 includes a quenching solution 837. Quenching solution 837 may comprise a quenching agent. The quenching agent may comprise an agent that stabilizes a size of a polymer-DNA complex that forms within mixing chamber 810.

In some examples, the quenching agent may comprise human serum albumin (HSA). The HSA may be recombinant HSA in some examples, whereas in other examples the HSA may be non-recombinant HSA.

System 800 further includes a controller 801. The controller 801 may be programmable via an operator of the system 800, and may store instructions in non-transitory memory that, when executed, cause the controller to control one or more or each of the first pump 815, second pump 818, first fluid control device 820, second fluid control device 822. By exerting control over the above-mentioned components, the controller controls the routing of the polymer solution 807 to the mixing chamber 810 and can simultaneously control the routing of the DNA solution 808 to the mixing chamber 810. The polymer solution 807 can be controlled to flow through the first connection line 811 to the mixing chamber 810 at a first flow rate, and the DNA solution 808 may be controlled to flow through the second connection line 812 to the mixing chamber 810 at a second flow rate. In some examples the first flow rate and the second flow rate may be the same, however in other examples the first flow rate and the second flow rate may be different. The first flow rate may be a function of the concentration of the polymer solution 807 and may further be a function of the concentration of the DNA solution 808. Similarly, the second flow rate may be a function of the concentration of the DNA solution 808, and may further be a function of the concentration of the polymer solution 807. Additionally or alternatively, the first flow rate and/or the second flow rate may be a function of a diameter of the first connection line 811 and/or the second connection line 812, respectively.

Mixing chamber 810 may be of a defined geometry, for example T-shaped as illustrated in FIG. 8B, to encourage consistent mixing and residence time of each of the polymer solution and the DNA solution within mixing chamber 810. While depicted as T-shaped, it may be understood that such a depiction is exemplary, and other geometries are within the scope of this disclosure provided that the geometry is selected to encourage consistent mixing and residence time of the polymer solution and the DNA solution, such that polymer-DNA nanoparticles are of a defined size upon reaching the quenching solution 837. As an example, the polymer-DNA nanoparticles may grow to a range comprising 400-1000 nanometers within mixing chamber 810, such that the polymer-DNA nanoparticles are within the range of 400-1000 nanometers at a time when the polymer-DNA nanoparticles are stabilized by the quenching solution 837.

iv. Viral Vectors

Exemplary viral vectors that can be produced from the disclosed methods and/or systems include retroviral vectors, such as lentiviral or gammaretroviral vectors, vectors derived from simian virus 40 (SV40), adenoviruses, and adeno-associated virus (AAV). Thus, while this discussion is focused on retroviral vectors, it is within the scope of this disclosure that other viral vectors can be produced without departing from the scope of this disclosure.

In some embodiments, recombinant nucleic acids are transferred into cells using retroviral vectors, such as lentiviral vectors or gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557. Retroviruses are useful as delivery vectors because of their ability to integrate their genes into the host genome, transferring a large amount of foreign genetic material, infecting a broad spectrum of species and cell types and of being packaged in special cell lines (Miller, 1992). Lentiviruses, in contrast to other retroviruses, in some contexts may be used for transducing certain non-dividing cells.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Napldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In some embodiments, two components are involved in making a virus-based gene delivery system: first, packaging plasmids, encompassing the structural proteins as well as the enzymes necessary to generate a viral vector particle, and second, the transfer plasmid, i.e., the genetic material to be transferred. Biosafety safeguards can be introduced in the design of one or both of these components. In some embodiments, the packaging plasmid can contain all HIV-1 proteins other than envelope proteins (Naldini et al., 1998). In some embodiments, viral vectors can lack additional viral genes, such as those that are associated with virulence, e.g. vpr, vif, vpu and nef, and/or Tat, a primary transactivator of HIV. In some embodiments, packaging systems for lentiviral vectors, such as HIV-based lentiviral vectors, include separate packaging plasmids that together comprise only three genes of the parental virus: gag, pol and rev, which reduces or eliminates the possibility of reconstitution of a wild-type virus through recombination.

In some aspects of the provided viral vectors, the heterologous nucleic acid encoding a recombinant protein, such as provided as part of an expression cassette containing the transgene under the control of a promoter, is contained and/or located between the 5' LTR and 3' LTR sequences of the vector genome, including wildtype LTRs or portions or chimeric portions thereof. In some embodiments, the viral vector, such as an HIV viral vector, lacks additional transcriptional units. In some embodiments, the vector genome can contain deletion in the U3 region of the 3' LTR of the DNA used to produce the viral vector RNA, which can generate a self-inactivating (SIN) vector. This deletion can then be transferred to the 5' LTR of the proviral DNA during reverse transcription. In some embodiments, the 3' LTR is deleted for the promoter and the enhancer of U3. In some embodiments enough sequence can be eliminated, including the removal of a TATA box, to abolish the transcriptional activity of the LTR. This can prevent production of full-length vector RNA in transduced cells. Thus, some embodiments include a deletion in the U3 region of the 3' LTR of the DNA. In some embodiments, this does not affect vector titers or the in vitro or in vivo properties of the vector.

In some embodiments, the viral vector genome may also contain additional genetic elements. The types of elements that can be included in the constructs are not limited in any way and can be chosen by one with skill in the art. In some embodiments, the vector genome contains sequences derived from a viral genome (e.g. lentiviral genome) that are non-coding regions of the genome that facilitate or provide recognition signals for DNA or RNA synthesis and processing. In some embodiments, such sequences can include cis-acting sequences that can be involved in packaging or encapsidation, reverse transcription and transcription and/or gene transfer or integration. In some embodiments, cis-activating sequences provided as part of the viral vector are derived from the same lentivirus or retrovirus-like organism.

In some embodiments, a signal that facilitates nuclear entry of the viral genome in the target cell may be included. An example of such a signal is the Flap sequence (also called a DNA Flap sequence) formed from the cPPT and CTS components that are part of the pol gene of a viral vector genome, such as a lentiviral vector genome. In some embodiments, a Flap sequence includes a portion of viral nucleic acid that contains a cPPT and/or a CTS region, but in which is deleted 5' and 3' portions of the pol gene that are not necessary for Flap function. In some cases, the viral vector does not contain a functional Flap region. As discussed below, in some embodiments a viral vector contains viral nucleic acid containing a variant Flap that lacks all or a portion of one or both of the cPPT and CTS region.

In some embodiments, the lentiviral vector genome can contain elements selected among a splice donor site (SD), a splice acceptor site (SA) and/or a Rev-responsive element (RRE). In some embodiments, RRE is provided to allow export of viral messenger RNA from the nucleus to the cytosol after binding of the Rev protein provided as part of a helper plasmid during viral packaging. In some embodiments, the vector genome can contain the psi (ψ) packaging signal, which, in some cases, can be derived from the N-terminal fragment of the gag ORF. In some embodiments, the psi packaging signal sequence can be modified by frameshift mutation(s) in order to prevent any interference of a possible transcription/translation of gag peptide, with that of the transgene.

In some embodiments, provided is a viral vector, such as a lentiviral vector, that contains a recombinant genome containing in order between the 5' and 3' LTR sequences of the vector genome: an RRE; a polynucleotide containing viral nucleic acid comprising a functional DNA Flap containing a cPPT and CTS that is inserted upstream of a promoter controlling expression of a polynucleotide encoding a recombinant protein; a transgene containing a promoter controlling expression of a polynucleotide encoding the recombinant protein, such as any described above and the polynucleotide encoding the recombinant protein, such as an antigen receptor (e.g. a CAR); and a polynucleotide containing a modified PRE, such as any provided herein, operably linked to the nucleic acid encoding the recombinant protein such as any provided herein. In some embodiments, the recombinant genome comprises the sequence 5' LTR-RRE-cPPT-CTS-transgene(s)-modified PRE-3' LTR. In some embodiments, the modified PRE in the viral vector, such as lentiviral vector is as described in WO2016115177. In some embodiments, the lentiviral vector is an HIV-1 derived lentiviral vector.

In some embodiments, among the provided polynucleotides, including viral vectors, are those containing variations in viral Flap sequences (deemed "variant Flap" polynucleotides or sequences). Such polynucleotides include those containing one or more modifications, e.g., deletion(s), within a viral Flap sequence within the polynucleotide. The variations can include complete deletion of a Flap sequence, or sub-part thereof, within a viral sequence of the polynucleotide. Such polynucleotides include viral vectors, such as a lentiviral vector, containing such variant Flap sequences. In some embodiments, the modified Flap in the viral vector, such as lentiviral vector is as described in WO2016115177.

In some embodiments, the vector also can contain sequences for propagation in a host cell, such as a prokaryotic host cell. In some embodiments, the nucleic acid of the viral vector contains one or more origins of replication for propagation in a prokaryotic cell, such as a bacterial cell. In some embodiments, vectors that include a prokaryotic origin of replication also may contain a gene whose expression confers a detectable or selectable marker such as drug resistance.

Preparation of Viral Vector Particles

In some embodiments, the nucleic acid, e.g., one encoding the desired sequence, such as the polynucleotide or expression cassette, is inserted into the viral genome in the place of certain viral sequences to produce a virus that is replication defective. In order to produce virions, a packaging cell line containing the gag, pol, and env genes but without the LTR and packaging components may be constructed. A recombinant plasmid also can be employed containing a polynucleotide, such as expression cassette, containing nucleic acid encoding a recombinant protein under the operable control of a modified PRE. When a recombinant plasmid together with the retroviral LTR and packaging sequences is introduced into a host cell, the packaging sequence may permit the RNA transcript of the recombinant plasmid to be packaged into viral particles, which then may be secreted into the culture media. The media containing the recombinant retroviruses in some embodiments is then collected, optionally concentrated, and used for gene transfer.

In some embodiments, a packaging cell line is transfected with one or more plasmid vectors containing the components necessary to generate the particles. The packaging cell line can express or be made to express essential lentiviral (e.g. HIV-1) genes to allow the generation of lentiviral particles, or other essential viral genes (e.g., adeno-associated viral genes), to allow the generation of adeno-associated viral particles. These genes can be expressed by several plasmids. In some embodiments, multiple vectors are utilized to separate the various genetic components that generate the retroviral vector particles. In some such embodiments, providing separate vectors to the packaging cell reduces the chance of recombination events that might otherwise generate replication competent viruses.

In some embodiments, a packaging cell line can be transfected with a lentiviral expression plasmid containing a cis-acting psi (Y) packaging sequence and the transgene gene inserted between the lentiviral LTRs to allow target cell integration; a packaging plasmid or plasmids encoding the pol, gag, rev and/or tat viral genes and, in some cases, containing the rev-response element (RRE) and a pseudotyping plasmid, such as a plasmid encoding an envelope protein, such as the G protein of the Vesicular Stomatitis Virus (VSV-G) envelope gene.

In some embodiments, a packaging cell line is transfected with a plasmid containing the viral vector genome, including the LTRs, the cis-acting packaging sequence and the sequence of interest, i.e. a nucleic acid encoding a recombinant protein, (e.g. an antigen receptor, such as a CAR) along with several helper plasmids encoding the virus enzymatic and/or structural components, such as Env, Gag, pol and/or rev. In some embodiments, a GagPol packaging plasmid containing the gag and pol genes encoding for structural and enzymatic components and a Rev plasmid containing the rev gene encoding for Rev regulatory protein are separately introduced into a packaging cell line. In some embodiments, a single plasmid vector having all of the retroviral components can be used. In some embodiments, an envelope plasmid encoding an env gene also can be introduced, which, in some cases, can result in viral particles pseudotyped with alternative Env proteins. In some embodiments, the retroviral vector particle, such as lentiviral vector particle, is pseudotyped to increase the transduction efficiency of host cells. For example, a retroviral vector particle, such as a lentiviral vector particle, is pseudotyped with a VSV-G glycoprotein, which provides a broad cell host range extending the cell types that can be transduced.

The env gene can be derived from any appropriate virus, such as a retrovirus. In some embodiments, the env is an amphotropic envelope protein which allows transduction of cells of human and other species. Some embodiments use retroviral-derived env genes, including, but not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). In some embodiments, other env genes such as Vesicular stomatitis virus (VSV) protein G (VSVG), that of hepatitis viruses, and of influenza also can be used.

In some embodiments, the packaging plasmid providing the viral env nucleic acid sequence is associated operably linked with regulatory sequences, e.g., a promoter or enhancer. The regulatory sequence in some embodiments can be any eukaryotic promoter or enhancer, including for example, EF1α, PGK, the Moloney murine leukemia virus promoter-enhancer element, the human cytomegalovirus enhancer, the vaccinia P7.5 promoter or the like. In some cases, such as the Moloney murine leukemia virus promoter-enhancer element, the promoter-enhancer elements are located within or adjacent to the LTR sequences. In some embodiments, the regulatory sequence is one which is not endogenous to the lentivirus from which the vector is being constructed. Thus, if the vector is being made from SIV, the SIV regulatory sequence found in the SIV LTR may be replaced by a regulatory element which does not originate from SIV.

In some embodiments, the viral vectors and the packaging plasmids are introduced via transfection or infection into the packaging cell line. The packaging cell line produces viral vector particles that contain the viral vector genome. Methods for transfection of the packaging cell line(s) are described herein. After cotransfection of the packaging plasmids and the transfer vector to the packaging cell line, the viral vector particles are recovered from the culture media and tittered by standard methods used by those of skill in the art. Thus, the packaging plasmids in some embodiments are introduced into human cell lines by these methods. In some embodiments, the packaging plasmids are provided together with a dominant selectable marker, such as neomycin, DHFR, Glutamine synthetase or ADA, followed by selection in the presence of the appropriate drug and isolation of clones. The selectable marker gene can be linked physically to the packaging genes in the construct.

In some embodiments, viral vector particles can be produced by stable cell lines wherein the packaging functions are configured to be expressed. Suitable packaging cells are known including, for example, U.S. Pat. No. 5,686,279; and Ory et al., (1996). The packaging cells with a lentiviral vector incorporated in them form producer cells. Producer cells are thus cells or cell-lines that can produce or release viral vector particles carrying the gene of interest. In some embodiments, these cells can further be anchorage dependent, which means that these cells will grow, survive, or maintain function optimally when attached to a surface such as glass or plastic. In some embodiments, these cells can be suspension-adapted such that these cells do not require attachment to a surface. In some embodiments, the producer cells may be neoplastically transformed cells. In some embodiments, host cells for transfection with the lentiviral vector and packaging plasmids include, for example, mammalian primary cells; established mammalian cell lines, such as COS, CHO, HeLa, NIH3T3, 293T, 293F, LV293, HEK 293, and PC12 cells; amphibian cells, such as Xenopus embryos and oocytes; other vertebrate cells; insect cells (for example, *Drosophila*), yeast cells (for example, *S. cerevisiae, S. pombe*, or *Pichia pastoris*) and prokaryotic cells (for example, *E. coli*).

In some embodiments, lentiviral vectors can be produced in a packaging cell line, such as an exemplary HEK 293 cell line, by introduction of plasmids to allow generation of lentiviral particles. Approximately two days after transfection of cells, e.g. HEK 293 cells, the cell supernatant contains recombinant lentiviral vectors, which can be used to transduce the target cells. Once provided to the target cells, the viral RNA present in the final viral vector is reverse-transcribed, imported into the nucleus and stably integrated into the host genome. One or two days after the integration of the viral RNA, the expression of the recombinant protein in the target cell can be detected.

The following examples are provided to illustrate particular features of certain embodiments. However, the particular features described below should not be construed as limitations on the scope of the disclosure, but rather as examples from which equivalents will be recognized by those of ordinary skill in the art.

EXAMPLES

Example 1

Complex Hold Time Effects Viral Titer

This example demonstrates that master mix hold time for LV293 transfection complexes can impact viral titer as a function of DNA and PEI concentration.

A brief overview of the suspension cell transfection process is depicted at FIG. 1A. Cells of this Example were transiently transfected using PEI-mediated four-plasmid system detailed in FIG. 1A. Target at-scale production system was performed in stirred tank bioreactor.

For this Example, all master mixes were prepared with a 3:1:1:1 transgene:rev:env:gag/pol molar ratio, and a 1:1

DNA:PEI mass ratio. Each plate well received a volume of master mix to bring the final DNA concentration to 2 μg/mL. The following conditions were tested in triplicate (Table 1):

TABLE 1

| Master Mix Preparation/Addition/Conditions | | | |
|---|---|---|---|
| | A<br>Master Max Prep | B<br>DNA Conc.<br>(μg/mL) | C<br>Hold Times<br>(min) |
| 1 | 1% | 220 | 0.5, 1, 1.5, 2, 2.5, 3, 3.5, 4 |
| 2 | 3% | 73.3 | 0.5, 1, 1.5, 2, 2.5, 3, 4, 8 |
| 3 | 10% | 22 | 1, 2, 3, 4, 6, 8, 10, 15 |

A sample of suspension-adapted HEK 293 cells (e.g. LV293 cells; Thermo Fisher, Walham, MA, PN A35347) growing in pH-neutral media (e.g. BalanCD media; Irvine Scientific, Santa Ana, CA, PN 91165) was split from an existing seed train and expanded for this Example. The culture was grown at 37° C. in 8% atmospheric $CO_2$ while shaking at 125 rpm. The cells were expanded into 2×250 mL cultures in a 1000 mL shake flask prior to seeding the production vessels.

Twenty-four hours before seed, the expansion culture was pooled and counted. The existing culture was used to produce 2×250 mL culture by diluting the expansion culture to 2.1e6 vc/mL. The cultures were placed in 1000 mL Erlenmeyer shake flasks and placed back in the incubator for 24 hours until transfection.

Before transfection, the bulk master mix solutions were prepared. DNA and PEI solutions were prepared in triplicate for 10%, 3%, and 1% master mixes. 3% and 1% master mix solutions were prepared in a 96 well 2 mL deep well plate (DWP). 10% master mix solutions were prepared in a 24 well 10 mL round bottom DWP. 3×44 μg/mL DNA and 3×44 μg/mL PEI solutions were prepared for the 10% master mixes. 3×146.7 μg/mL DNA and 3×146.7 μg/mL PEI solutions were prepared for the 3% master mixes. Three separate 440 μg/mL DNA and three separate 440 μg/mL PEI solutions were prepared for the 1% master mixes.

Immediately before transfection, three 24 well DWPs were placed in a biological safety cabinet (BSC). The seed cultures were placed in the BSC and pooled. A 3 mL seed cell culture was placed in each well in the three 24 DWPs. The DWPs were labeled 10%, 3%, and 1% and were placed in a shaking incubator until transfection.

Transfection was performed in three separate steps, with each step accounting for each master mix prep group. Triplicate master mixes for each master mix prep group were prepared simultaneously using a multichannel pipettor. Master mix prep groups were prepared one at a time and used to transfect all relative hold time points before the next master mix prep group was prepared. Specifically, hold times for the 1% master mix were 0.5, 1, 1.5, 2, 2.5, 3, 3.5, and 4 minutes, hold times for the 3% master mix were 0.5, 1, 1.5, 2, 2.5, 3, 4, and 8 minutes, and hold times for the 10% master mix were 1, 2, 3, 4, 6, 8, 10 and 15 minutes. Wells were mixed using a multichannel pipettor after master mix addition. Plates were returned to the shaker incubator after all wells had been transfected.

Forty-eight hours after transfection, each plate was centrifuged at 1000×g for five minutes to clarify. Three 0.5 mL samples of each clarified well were aliquoted and stored at −80° C. until analyzed. A serial dilution of lentiviral vector samples were used to transduce the cell line. 48-72 hours after transduction, a fluorescently labeled antibody staining for surface expression of CAR protein was used to quantify percent transduced cells via flow cytometry. The values from the lowest two dilutions were used to calculate the functional titer in transduction units per mL (TU/mL). Individual sample values are provided in the table of FIG. 1B.

Figure 1C:
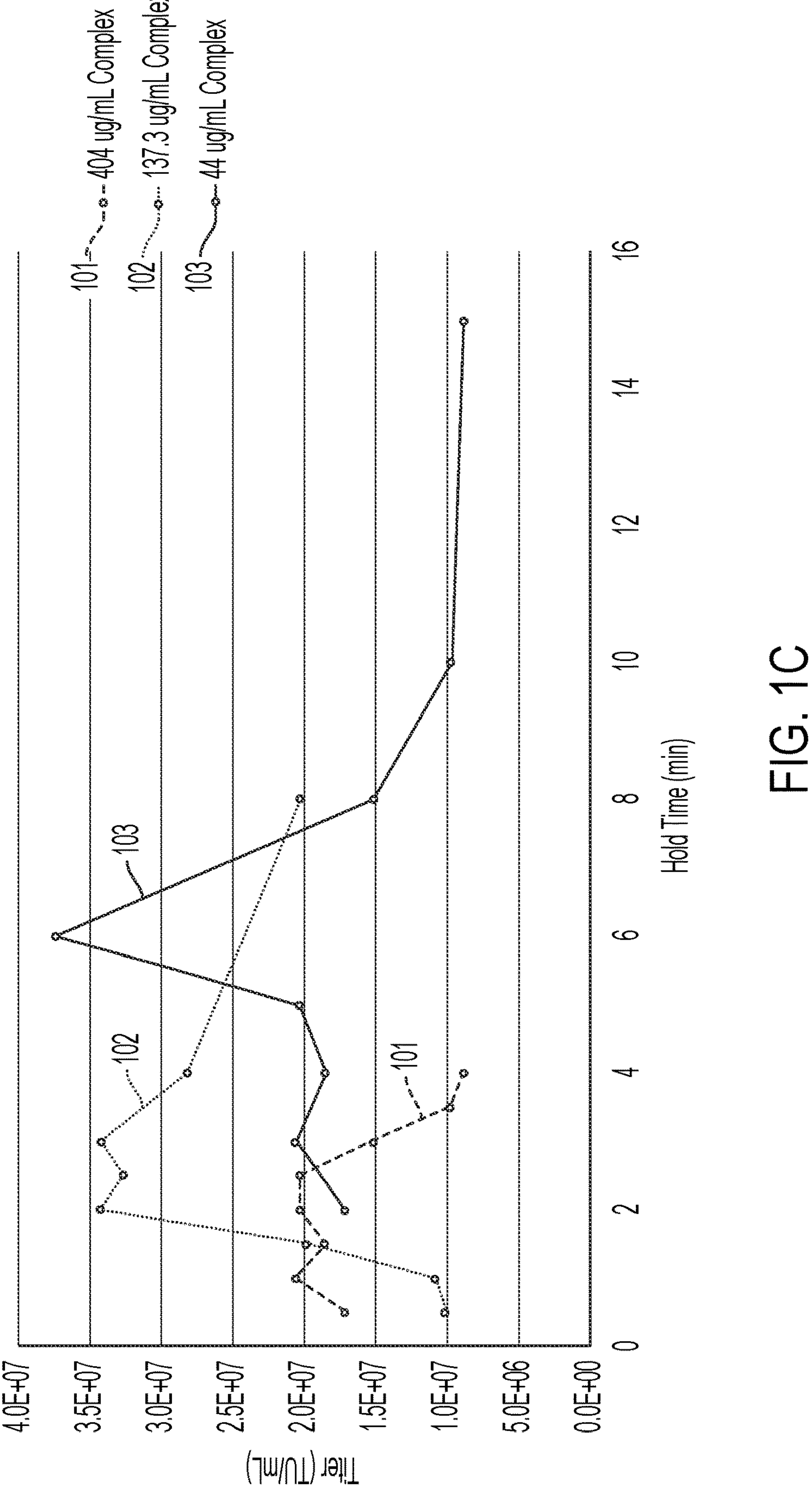
FIG. 1C is a graph showing that lentiviral vector titer at harvest is a function of polyethyleneimine-DNA (PEI-DNA) transfection complex concentration and a hold time between mixing DNA and PEI and transfecting cells with the PEI-DNA transfection complex.

The averaged values from each replicate are plotted by master mix prep group as shown in FIG. 1C. At FIG. 1C, plot 101 is the 1% v/v MM, plot 102 is the 3% v/v MM, and plot 103 is the 10% v/v MM. A peak for the 10% master mix was observed between the five minute and eight minute hold time. A peak for the 3% master mix was observed between the 1.5 minute hold time and four minute hold time. A peak for the 1% master mix was not readily apparent, but may be less than one minute, and may not have been measurable due to the restraints of manual addition.

The results shown in this Example demonstrate that DNA-PEI master mixes can be significantly impacted by hold time during preparation, and that the concentration of DNA and PEI in the master mix could have a significant role determining what the optimal hold time may be for a given master mix. Higher concentrations of DNA and PEI were shown to result in shorter optimal hold times. It is contemplated that this could be a result of higher DNA and PEI concentrations increasing the rate of complex formation in the master mix. The data shown in this Example indicate that hold time is a factor in terms of maximizing viral titer at harvest for a given master mix in 293 PEI-based transfections.

As shown in FIG. 1C, peak titers of samples transfected by the 1% master mix solution were significantly lower than the peak titers of 3% and 10% master mix samples. However, that the 1% master mix samples did not show a clear peak may suggest that the peak hold time occurred prior to the first addition (30 s). This is consistent with the shortening of the peak hold time with increasing master mix concentration seen between the 3% and 10% samples. The difficulty in forming and using a master mix in 30 s could mean using a 1% master mix at its peak hold time would be challenging at larger scales. However, the titers produced by 1% master mix samples with hold times up to 2 min are high enough for the process at scale.

Studies were performed to evaluate the negative impact of complex incubation time exacerbated as production volume increases. The studies revealed that the rate of complex potency loss is not scale dependent and complex volume increased linearly with increasing culture volume, increasing complex preparation and transfer time. The estimated complex volume for commercial batches (Table 2) would require preparation and transfer times far beyond optimal incubation period, resulting in significantly lower titers at harvest. A method to stabilize complex activity for longer incubation times would mitigate titer decrease when scaling up.

TABLE 2

Complex volume by culture volume for 3 complex concentrations.

| | | Complex solution volume<br>Complex Conc. | | |
|---|---|---|---|---|
| | | 44 μg/mL | 137.3 μg/mL<br>Ideal hold time | 404 μg/mL |
| | | <2 min | 2-4 min | 6-8 min |
| Culture | 1 L | 10 mL | 30 mL | 100 mL |
| Volume | 10 L | 100 mL | 300 mL | 1 L |

TABLE 2-continued

Complex volume by culture volume for 3 complex concentrations.

| | Complex solution volume Complex Conc. | | |
|---|---|---|---|
| | 44 μg/mL | 137.3 μg/mL | 404 μg/mL |
| | Ideal hold time | | |
| | <2 min | 2-4 min | 6-8 min |
| 50 L | 500 mL | 1.5 L | 5 L |
| 200 L | 2 L | 6 L | 20 L |
| 500 L | 5 L | 15 L | 50 L |

Example 2

Addition of HSA to Master Mix Increases Viable Hold Time in Vector Production Process This Example demonstrates that addition of human serum albumin (HSA) to the master mix after mixing of DNA and PEI solutions can increase viable hold time in a vector production process.

For this example, forty-eight different conditions were tested. All conditions were tested in 3 mL cultures in 24 well DWPs. Two different human serum albumin (HSA) addition methods were tested. The first addition method formed the complex by mixing DNA and PEI to begin complex formation, followed by addition of HSA 2 minutes after mixing. The second addition method mixed HSA and DNA prior to PEI addition, and formed the complex by adding PEI to the DNA-HSA mixture. Within each addition method, samples were tested at HSA concentrations of 0, 0.05, 0.2, 2, 5, and 10 mg/mL. All master mixes were supplemented with media to a set maximum volume as determined by the 10 mg/mL master mix volume. For each HSA concentration, one master mix was prepared per addition method and was added to wells at either 2, 10, 20, or 30 minutes after starting the transfection complex formation. HSA was drawn from a 250 mg/mL bulk solution (e.g., as produced by Octapharma (Langenfeld, Germany) (25% Albumin (human), NDC #68982-643-02, Lot #K838A6871)).

All conditions were seeded from the same seed train. A seed train was expanded into 1×250 mL culture in a 1000 mL shake flask. At seed, the cell culture was diluted to $2.1e^6$ vc/mL. The culture was grown for an additional 24 hours before transfection. Immediately prior to transfection, 3 mL of cell culture was placed in 48 wells split evenly across 4 plates. In a separate 96 well DWP, 12 separate master mixes were made with HSA added at the concentration and time indicated in Table 4 below. All master mixes were made by mixing equal volume DNA and PEI solutions together. Each master mix was prepared with a 3:1:1:1 transgene:rev:env:gag/pol plasmid molar ratio and a 1:1 DNA:PEI mass ratio. The final DNA concentration in each master mix was 68.65 μg/mL. For master mix solution 1-6, HSA was added to the PEI-DNA solution to the concentration indicated in Table 3 after the two solutions had been mixed. For master mix solutions 7-12, HSA was added to the DNA solution prior to mixing with the PEI solution. The concentration of USA added was calculated so the final concentration of HSA after mixing the PEI solution would equal the concentraion indicated in Table 3. All master mixes were made at a 480 μL scale. 250 mg/mL HSA was serially diluted in pH-neutral media so that the addition volume of HSA to each master mix or DNA solution was 20 μL. The final volume of each master mix and HSA solution was 500 μL.

TABLE 3

Master Mix Preparation Parameters

| Master Mix | HSA Conc (mg/mL) | HSA Addition | HSA Addition time |
|---|---|---|---|
| MM 1 | 0 | N/A | N/A |
| MM 2 | 0.05 | Post-Mix | 2 min after complex |
| MM 3 | 0.2 | Post-Mix | 2 min after complex |
| MM 4 | 1 | Post-Mix | 2 min after complex |
| MM 5 | 5 | Post-Mix | 2 min after complex |
| MM 6 | 10 | Post-Mix | 2 min after complex |
| MM 7 | 0 | N/A | N/A |
| MM 8 | 0.05 | Pre-Mix | Pre-complex (to DNA) |
| MM 9 | 0.2 | Pre-Mix | Pre-complex (to DNA) |
| MM 10 | 1 | Pre-Mix | Pre-comptex (to DNA) |
| MM 11 | 5 | Pre-Mix | Pre-complex (to DNA) |
| MM 12 | 10 | Pre-Mix | Pre-complex (to DNA) |

Wells were transfected 2, 10, or 30 minutes after the start of complex formation. Wells receiving complex at similar times were grouped on the same plate. Each well received 90 μL of its respective master mix at transfection.

All cultures were incubated until 48 hours after transfection. Cultures were clarified by centrifugation at 1000×g for 5 minutes. The supernatant from each well was harvested and aliquoted into samples. Samples were frozen at −80° C. immediately after harvest. All samples were thawed and measured for titer. Samples with similar HSA addition patterns were compared to determine the impact of HSA addition to the transfection complex.

Figure 1D:
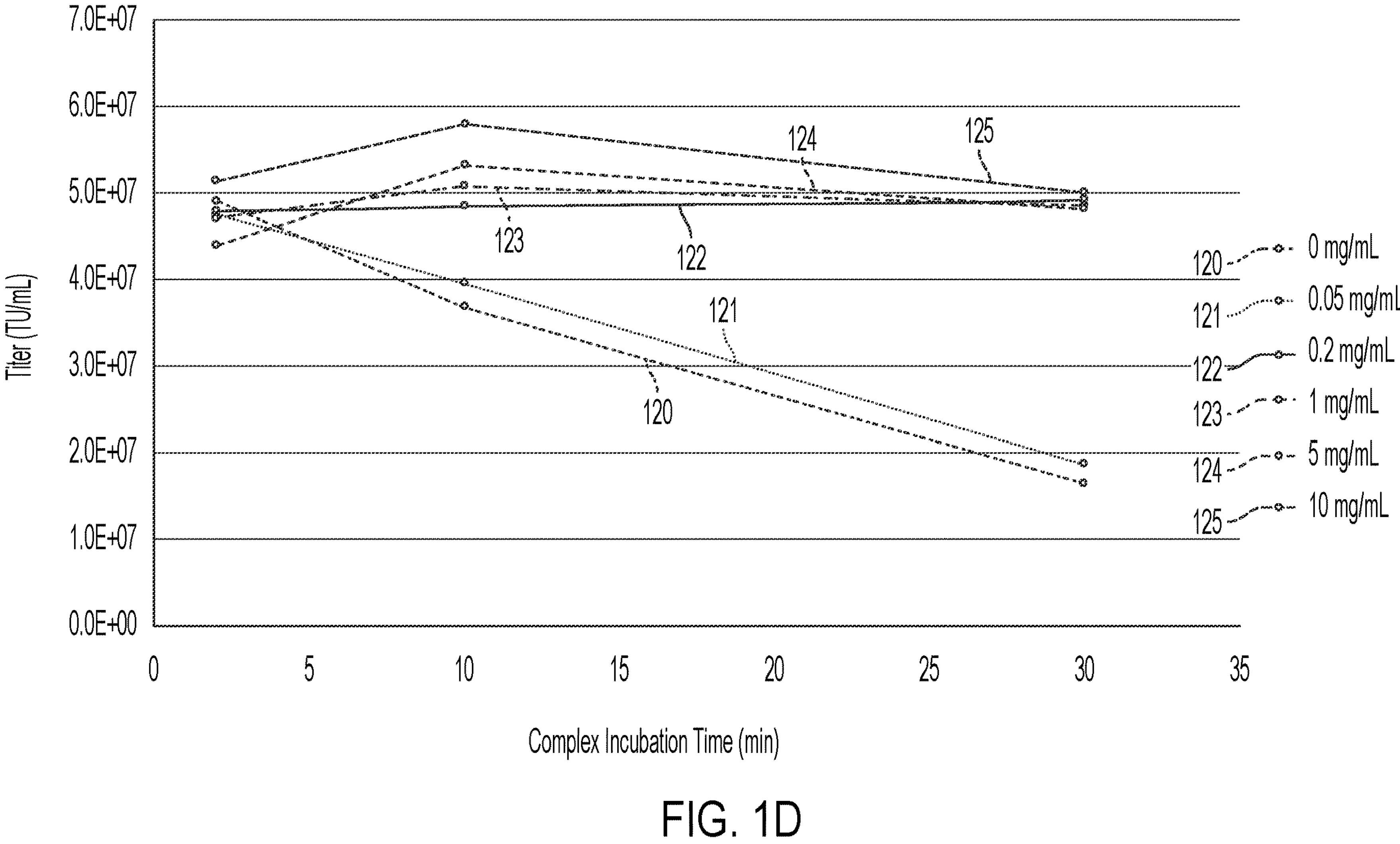
FIG. 1D depicts a graph illustrating titer by incubation time for 137.3 μg/mL PEI-DNA complexes supplemented with 0-10 mg/mL HSA.

Infectious titer values obtained by the first addition method (Master Mixes 1-6, HSA addition after mixing of DNA and PEI) were measured. The results demonstrate that adding HSA at concentrations of 0.2-10 mg/mL or greater to the DNA-PEI solution increase the length of time the master mix can be held outside of culture and still produce acceptable titers (FIG. 1D). At FIG. 1D, plot 120 is the 0 mg/mL condition, plot 121 is the 0.05 mg/mL condition, plot 122 is the 0.2 mg/mL condition, plot 123 is the 1 mg/mL condition, plot 124 is the 5 mg/mL condition, and plot 125 is the 10 mg/mL condition.

Titers transfected with master mixes 3-6 produce effectively equivalent titers 2, 10, and 30 minutes after mixing. Cultures transfected with master mixes 1 and 2 showed a decrease in titer as the hold time increased. This result has been observed before in master mixes produced without HSA addition, as was done for the control condition (master mix 1). Samples transfected with master mix 2 showed a similar pattern of decreasing titer with increasing hold time, indicating that a minimum concentration of HSA greater than 0.05 mg/mL is required to maintain consistent titers across a 30 minute hold.

HSA was added to the DNA solution at the concentrations listed in Table 3 for master mixes 7-12 prior to PEI solution addition. The PEI solutions were added to create the complex and the complexes were used to transfect cultures at 2, 10, and 30 minutes. The harvest materials from these cultures were tested for infectious titer. The infectious titer data for this assay demonstrates that adding HSA at concentrations of 1 mg/mL or greater to the DNA solution prior to addition of PEI has a negative effect on titer. Virtually no infectious titer was measured in test conditions that included 1 mg/mL HSA, 5 mg/mL HSA and 10 mg/mL HSA (data not shown). It may be that at these higher concentrations of HSA the master mix is prevented from forming by complexing with the PEI in place of the DNA.

Thus, adding HSA to the master mix after mixing the PEI and DNA solutions increased the viable hold time for all solutions supplemented with HSA at 0.2-10 mg/mL HSA. Samples transfected with these master mixes displayed steady titers across hold times from 2-30 minutes. This is in contrast to the control sample and master mixes supplemented with HSA to 0.05 mg/mL or less, which produced decreasing titers with increasing hold times. The addition of HSA at 0.2 mg/mL or higher appears to stabilize the transfection complex. It is hypothesized that the degradation of the transfection complex with time is the result of the transfection complexes aggregating to sizes too large for the producer cells to ingest them. The addition of HSA may prevent further aggregation of the complexes.

HSA addition to the DNA solution prior to master mix formation did not extend the hold time of the transfection complex or improve the titer at harvest based on the results of the experiments described above. All samples transfected with master mixes prepared with DNA solutions containing HSA at concentrations of 1 mg/mL or higher (via the second addition method) did not produce measurable amounts of vector. Because HSA is negatively charged in neutral pH solutions, it may complex with the PEI. The concentration of HSA in these master mixes is far higher than the concentration of DNA, so it may be that the HSA complexed with the PEI much more favorably than the DNA. Samples transfected with master mixes prepared with DNA solutions containing 0.2 mg/mL HSA displayed some ability to extend the viable master mix hold time. Samples transfected at 10 minutes and 30 minutes produced more vector than samples transfected at 2 minutes, suggesting that the optimal hold time of master mixes prepared with 0.2 mg/mL HSA in the DNA solution may be longer than 2 minutes and that the master mix may be stable for a longer period of time after the optimal hold time is reached.

Example 3

HSA Addition to DNA-PEI Transfection Complex Impacts Overall Size of Complex This Example demonstrates that HSA addition to a DNA-PEI transfection complex can impact an overall size of the transfection complex, as a function of DNA and PEI concentration.

For this Example, DNA, PEI and HSA concentration in the master mix were tested by dynamic light scattering (DLS) for impact on particle size over time. Experimental conditions specified in the table shown in FIG. 2A were prepared and measured for particle size. Plasmid concentration was tested at 22, 73.3, and 220 μg/mL. All complexes used a 1:1 DNA:PEI mass ratio and p10013 for plasmid. To prepare the complex, the DNA solution was prepared at 1 mL and added to a square bottom cuvette. A 1 mg/mL p10013 plasmid solution was diluted in pH-neutral media to reach the target concentration listed in the table shown at FIG. 2A. The PEI solution was prepared at 1 mL by diluting a 1 mg/mL PEI solution in pH-neutral media to reach the target concentration listed in the table shown at FIG. 2A. The PEI solution was added to the cuvette containing the DNA solution and the solution was mixed. Sizing measurements were begun immediately after mixing. For complexes receiving albumin, 40 μL of a 50 mg/mL HSA solution was added 3 minutes after complex formation was initiated. The 50 mL HSA solution was prepared by diluting HSA in pH-neutral media. The HSA was drawn from a 250 mg/mL bulk solution.

All DLS measurements were taken using a Zetasizer (Malvern, United Kingdom), and all material were allowed to equilibrate to room temperature prior to use. All samples were prepared in a 10×10×45 mm square bottom polystyrene cuvette (Sarstedt, Newton, NC, #67.754). All measurements were made with the settings listed in Table 4 below.

TABLE 4

Zetasizer settings

| Parameter | Setting |
|---|---|
| Material reflexive index | 1.45 |
| Absorption | 0.001 |
| Dispersant | Water |
| Dispersant temperature | 20° C. |
| Dispersant viscosity | 1.0031 cP |
| Sample viscosity | 1.0031 cP |
| Dispersant refractive index | 1.33 |
| Equilibration temperature | 20° C. |
| Equilibration time | 0 seconds |
| Cell | DTS0012 |
| Measurement angle | 173° |
| Measurement position | 1.5 mm (fixed) |
| Attenuation selection | Automatic |

The size of DNA, PEI and HSA were determined prior to forming the complexes. Measurement frequency for determining sizing prior to forming the complexes included single 60 second measurements. The sizes of the particles are shown in Table 5.

TABLE 5

Pre-complex material sizes

| Material | Concentration (μg/mL) | Average particle size (nm) |
|---|---|---|
| Media | N/A | 8.531 |
| DNA in Media | 220 μg/mL | 76.01 |
| | 73.3 μg/mL | 67.23 |
| | 22 μg/mL | 67.46 |
| PEI in Media | 220 μg/mL | 7.238 |
| HSA in Media | 1000 μg/mL | 24.55 |

Figure 2B:
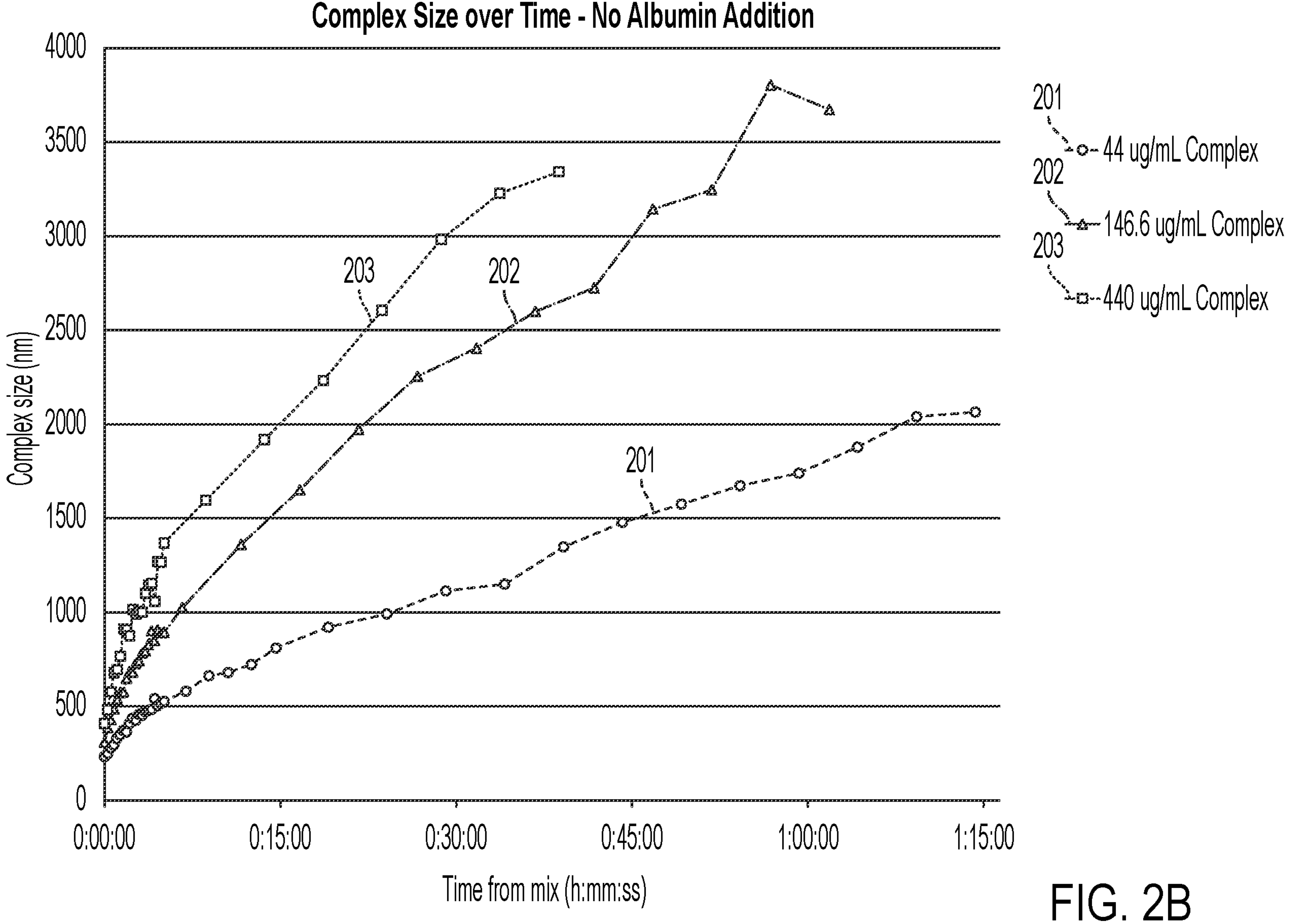
FIG. 2B is a graph showing PEI-DNA transfection complex size increase over time as a function of time PEI and DNA concentration.

The complex particle size over time for transfection complexes prepared at 22 μg/mL, 73.3 μg/mL and 220 μg/mL each of DNA and PEI (10%, 3% and 1% culture volume complexes, respectively) are shown in FIG. 2B. At FIG. 2B, plot 201 is the 44 μg/mL sample, plot 202 is the 146.6 μg/mL, and plot 203 is the 440 μg/mL sample. As illustrated, the change in particle size is seen to be concentration dependent, with complexes prepared in smaller volume and higher concentration solutions increasing in size at a faster rate. Measurement frequency for the three different solutions included a 15 second measurement every 15 seconds between 0-5 minutes, and 60 second measurements every 5 minutes between 5-60 minutes.

Figure 3:
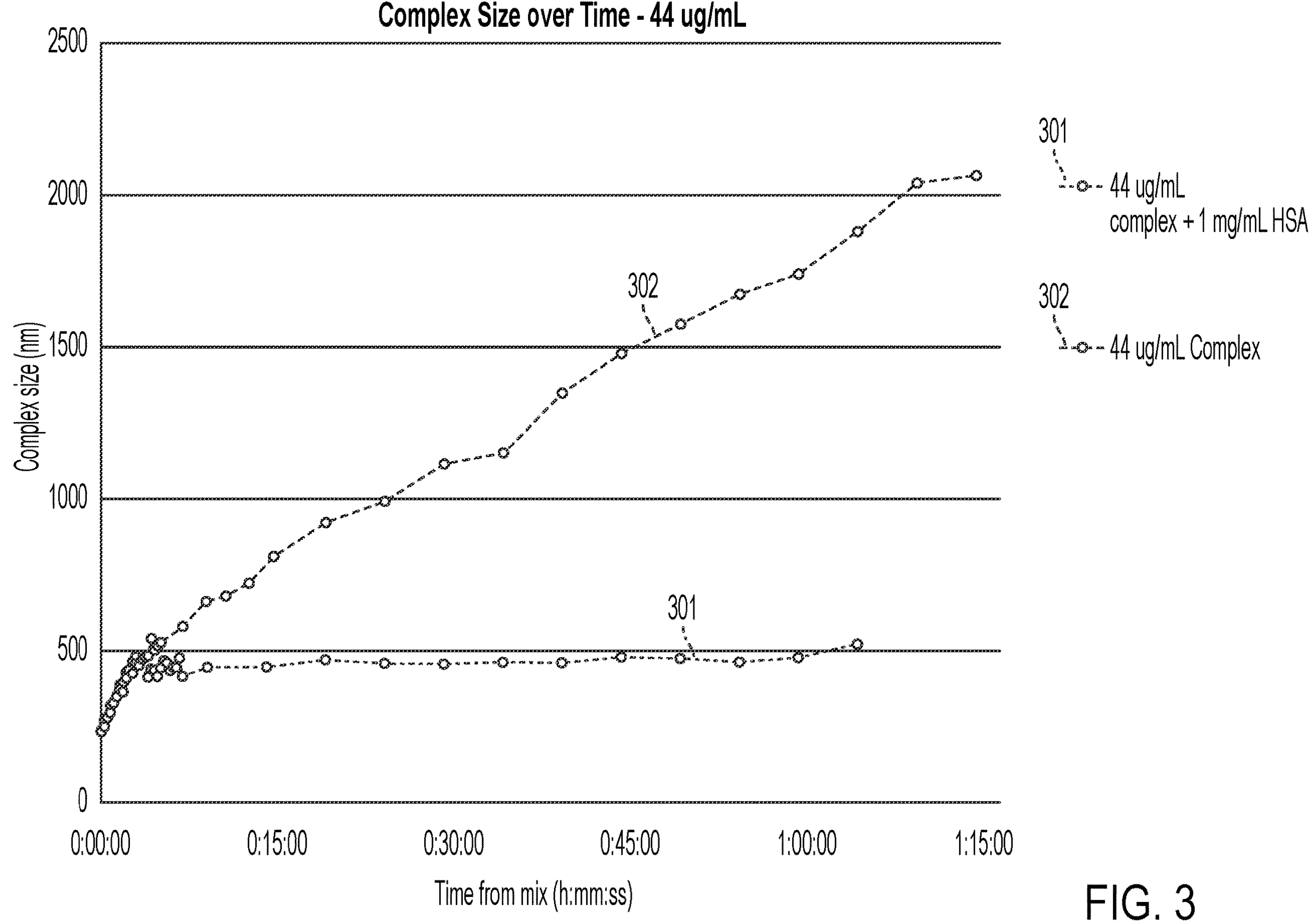
FIGS. 3-6 are graphs that show changes in PEI-DNA transfection complex size as a function of time with and without HSA, for varying PEI-DNA transfection complex concentrations.

To examine the impact of HSA addition on transfection complex size, 44 μg/mL, 146.6 μg/mL and 440 μg/mL transfection complexes were similarly prepared and measured for size by DLS. Three minutes after mixing, a 50 mg/mL HSA solution was added to the complex to bring the total HSA concentration in the complex to 1 mg/mL. The impact of HSA addition on each complex is shown at FIGS. 3-6. Briefly, with regard to FIG. 3, HSA was added to a 44

µg/mL complex three minutes after complex formation started. After HSA addition, the average complex size did not significantly increase further up to one hour after mixing. At FIG. 3, plot 301 is the 44 µg/mL complex+0.1% HSA and plot 302 is the 44 µg/mL complex without HSA. Measurement frequency for the 44 µg/mL complex+HSA was as follows. Prior to HSA addition (between 0-3 minutes), measurement frequency included a 15 second measurement every 15 seconds. After HSA addition, measurement frequency included a 15 second measurement every 15 seconds between 3-6 minutes, and a 60 second measurement every 5 minutes between 6-60 minutes).

Figure 4:
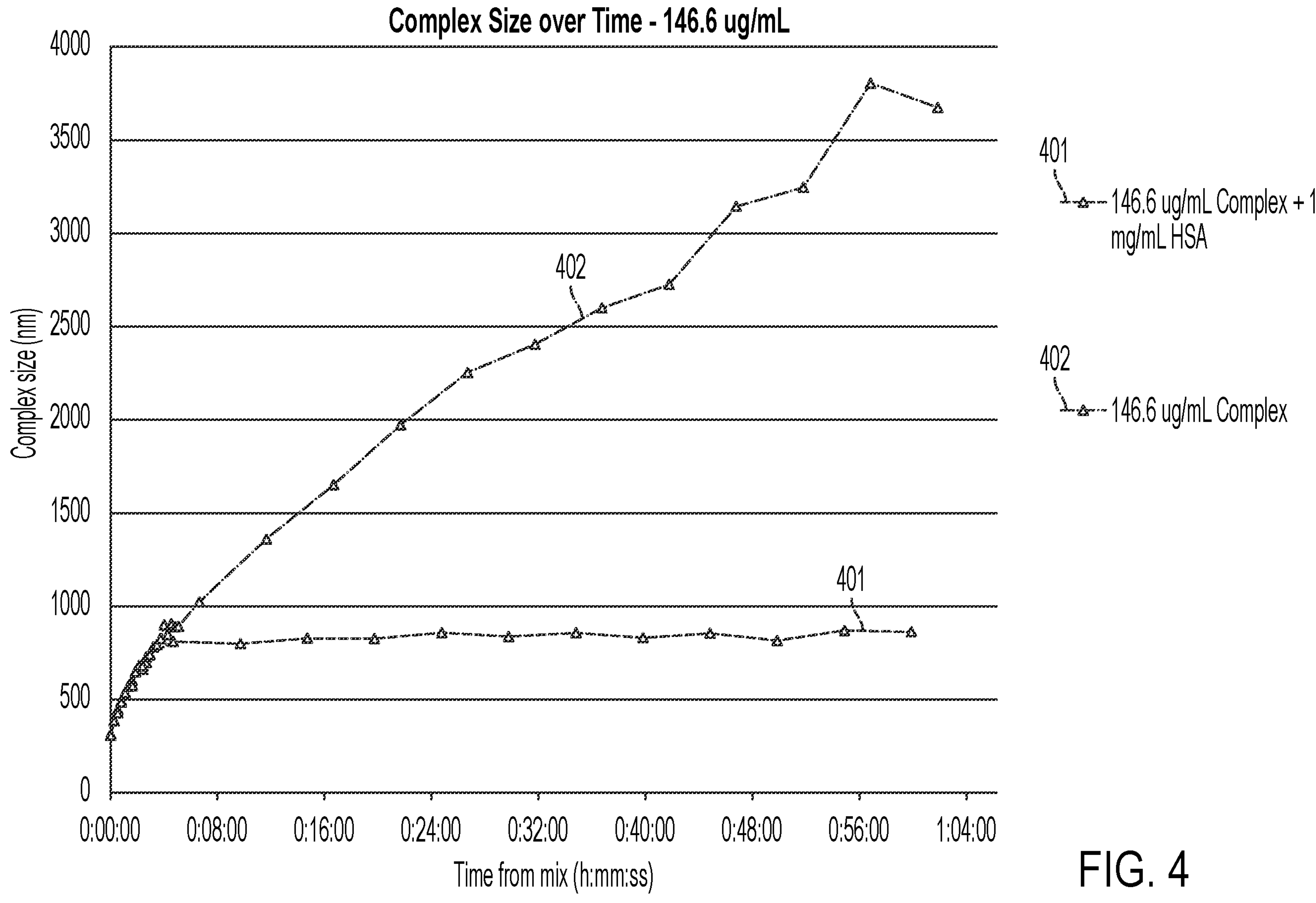

With regard to FIG. 4, HSA was added to a 73.3 µg/mL complex three minutes after complex formation started. After HSA addition, the average complex size did not significantly increase further up to 1 hour after mixing. At FIG. 4, plot 401 is the 146.6 µg/mL complex+0.1% HSA and plot 402 is the 146.6 µg/mL complex without HSA. Measurement frequency for the 73.3 µg/mL complex+HSA was as follows. Prior to HSA addition (between 0-3 minutes), measurement frequency included a 15 second measurement every 15 seconds. Due to time constraints, the measurement parameters for the 146.6 µg/mL complex+0.1% HSA included 60 second reads every five minutes out to 60 minutes immediately after albumin addition, rather than 15 seconds reads every 15 seconds for 3 minutes followed by 60 seconds reads every 5 minutes described in Table 5.

Figure 5:
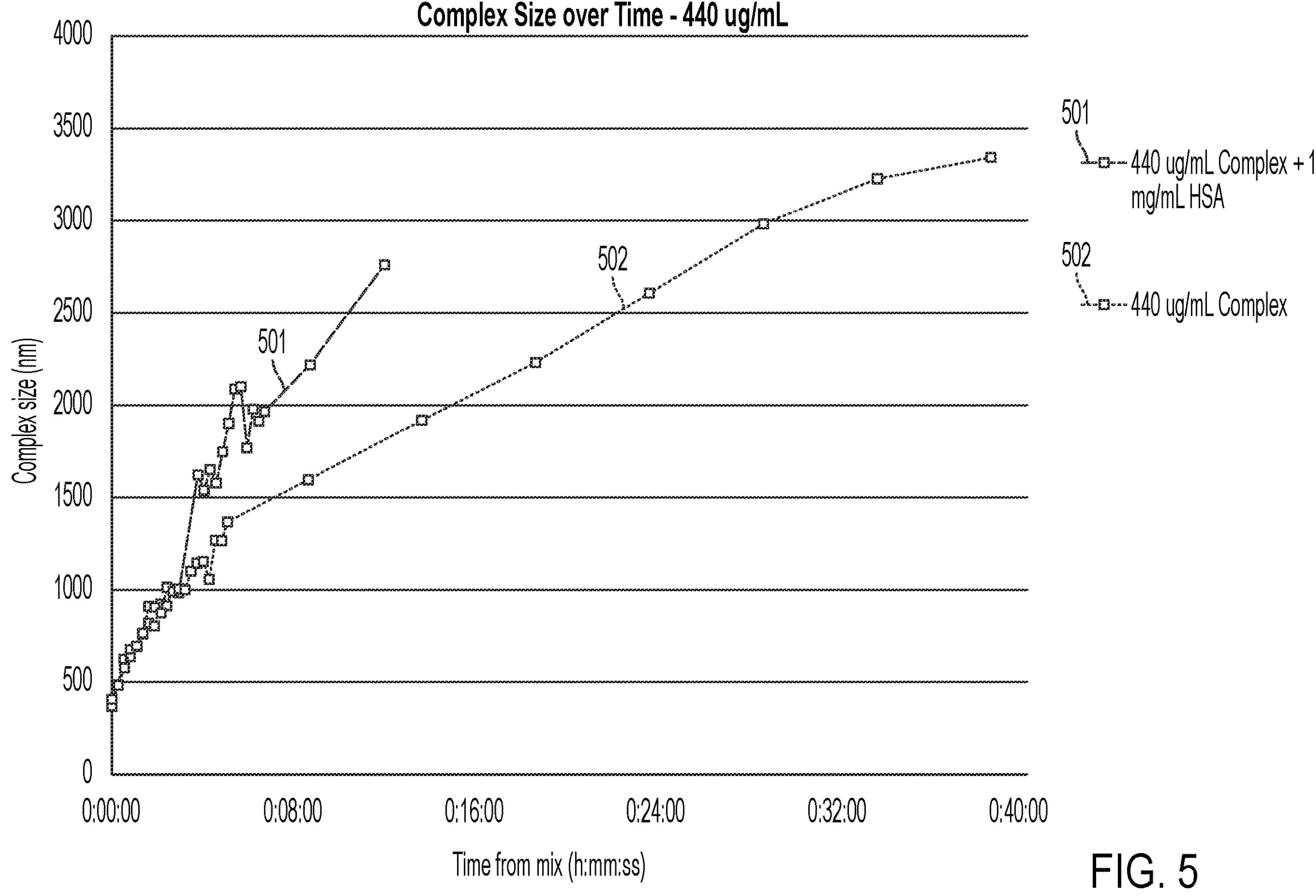

With regard to FIG. 5, HSA was added to a 440 µg/mL complex three minutes after complex formation started. After HSA addition, the average complex size continued to increase, and increased at a more rapid pace than a 440 µg/mL complex without HSA added. Size measurement for the +HSA complex was stopped after 12 minutes because of the clear trend upward in complex size. At FIG. 5, plot 501 is the 440 µg/mL complex+0.1% HSA and plot 502 is the 440 µg/mL complex without HSA.

These studies demonstrate that PEI-DNA complexes increase in size as the hold time after mixing increases. The increase in size is likely the result of complexes aggregating together as the DNA and PEI have more chances to interact and complex. Increasing the concentration of PEI and DNA in the complex solution increases the rate at which these complexes form. The increased concentration may increase the likelihood of PEI and DNA coming in contact, which may result in more frequent complexation.

The addition of HSA to the complex solutions had a concentration dependent effect on the size of the PEI-DNA complex. For 146.6 and 44 µg/mL complexes, the addition of HSA to 1 mg/mL halted complex size increase for up to an hour. The abrupt stop in complex size increase is in direct contrast to the linear increase in complex size seen in equivalent concentration complex solutions without albumin. Without being bound by a particular theory, it is believed that the HSA prevents further complex aggregation by complexing with PEI at all available opportunities not already complexed with DNA. The much higher concentration of HSA compared to PEI and DNA may render virtually all of the PEI not already complexed to immediately complex with HSA instead of gradually continuing to complex with DNA.

The 440 µg/mL complex solution did not cease complex size increase when HSA was introduced. Conversely, the particle size rapidly increased when the HSA was added and continued to increase after the HSA was added. The sudden increase in size may be a result of the solution being mixed after HSA addition. Because of high concentration of DNA and PEI in the solution, mixing can present a sudden and noticeable increase in complexing opportunities. Solutions with lower concentrations may not have a noticeable increase in complexation opportunities. The HSA added may not have been concentrated enough to prevent further DNA and PEI complexation. Increasing the HSA concentration may prevent complex aggregation in a 440 µg/mL complex solution (or higher), but the HSA addition time would likely have to be extremely early to create complexes at or near a desired or optimal size. For complex concentrations of 146.6 µg/mL or less, adding HSA to a final concentration of 1 mg/mL is a viable method to prevent complex aggregation.

Figure 6:
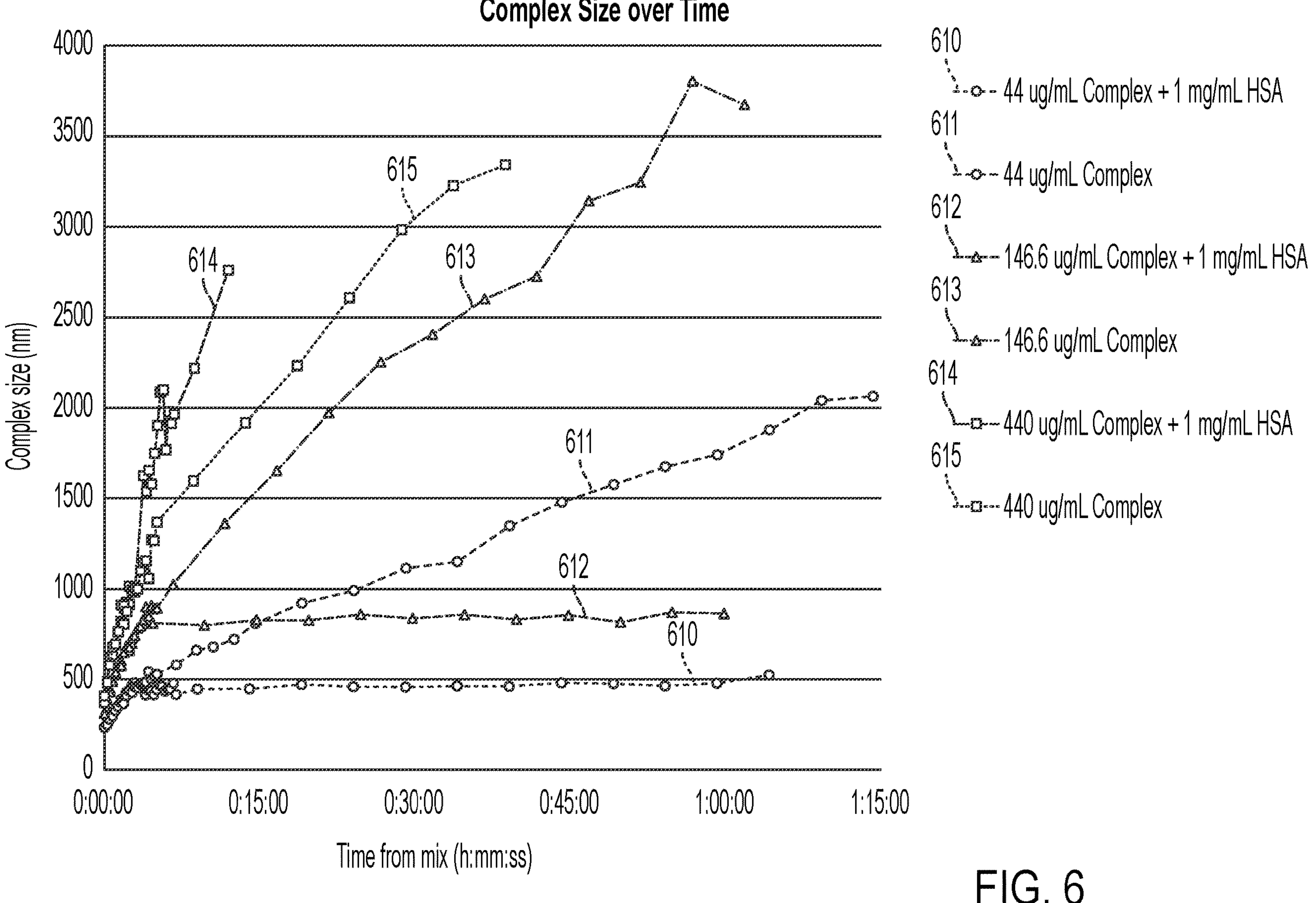

Additional studies were performed evaluating additional time points which are shown in FIG. 6. For these studies, p10013 plasmid was suspended in 3 different media solutions at 44 µg/mL, 146.6 µg/mL, and 404 µg/mL. PEI was suspended in 3 different media solutions at 44 µg/mL, 146.6 µg/mL, and 404 µg/mL. 5 mL of each solution was made. 0.5 mL 44 ug/mL DNA solution was placed in a Sarstedt square 12 mm×12 mm×45 mm clear polystyrene cuvette (Sarstedt, Newton, NC, PN 67.754) and placed in the zetasizer DLS cuvette holder. 0.5 mL 44 µg/mL PEI was added to the cuvette and the solution was mixed. Immediately after mixing, the zetasizer DLS program was initiated and DLS measurements were taken. Particle size values were averaged over 15 second intervals for 5 minutes, and then over 5 minute intervals for 70 minutes. This was repeated with the 146.6 µg/mL DNA and PEI solutions and the 404 µg/mL DNA and PEI solutions for 55 and 33 minutes, respectively. After completing these runs, all measurements were repeated, but each solution was supplemented with a 50 mg/mL HSA solution to 1 mg/mL HSA after the initial 5 minute DLS read. The 44, 146.6, and 404 µg/mL solutions were run for 59, 55, and 7 minutes, respectively. The 404 µg/mL solutions were stopped earlier than the other solutions because the particle size had exceeded the size range where endocytosis was considered possible. The particle size over time for each solution is plotted in FIG. 6. At FIG. 6 plot 610 is the 44 µg/mL complex+1 mg/mL HSA, plot 611 is the 44 µg/mL complex without HSA, plot 612 is the 146.6 µg/mL complex+1 mg/mL HSA, plot 613 is the 146.6 µg/mL complex without HSA, plot 614 is the 404 µg/mL complex+1 mg/mL HSA, and plot 615 is the 404 µg/mL complex without HSA.

The DLS data of the complex demonstrates a clear link between complex concentration and the rate of complex size change. Higher DNA and PEI concentrations demonstrate greater rates of size increase over time. The addition of HSA to the complex showed a clear impact on complex formation in the 44 µg/mL complex and the 146.6 µg/mL complex. Complex size change mirrored the unsupplemented complexes until the HSA addition. After HSA addition, complex size remained static for up to approximately 1 hour. The 404 µg/mL complex did not show a similar effect, but instead increased at an even more rapid pace after HSA addition.

The size data of the unsupplemented complexes provides an explanation for the change in optimal transfection incubation when reducing the master mix volume. The rate of change of complex size increases as the concentration of the complex in the master mix increases. The differences in complex size at a given point of time and the differences in optimal incubation time suggest that there is an optimal complex size or size range that should be targeted to maximize titer.

The decrease in the rate of complex size change to zero observed in complexes after HSA supplementation suggests a mechanism of action for why the addition of HSA prevents loss of titer. If added in high enough concentrations, HSA prevented further complex size change. Without being bound to a theory, it is contemplated that complexes likely become more difficult for cells to endocytose as size increases, and by preventing further aggregation, complex particles can stay within the endocytosis size range longer. This effect was observed in the 44 μg/mL and 146.6 μg/mL complex solutions, but not in the 404 μg/mL complex solutions. It is likely that the concentration of complex particles was too high for the HSA present to prevent aggregation. The studies presented in FIG. 6 indicate supplementing a 146.6 μg/mL complex solution with HSA to 1 mg/mL will prevent titer loss at all future 293 lentiviral production processes, regardless of scale.

Example 4

Evaluation of Complex Hold Time after HSA Addition for Up to 24 Hours

This Example characterizes the effect of transfection complex hold time on viral vector production in cultures transfected with complexes with or without HSA addition.

Figure 7A:
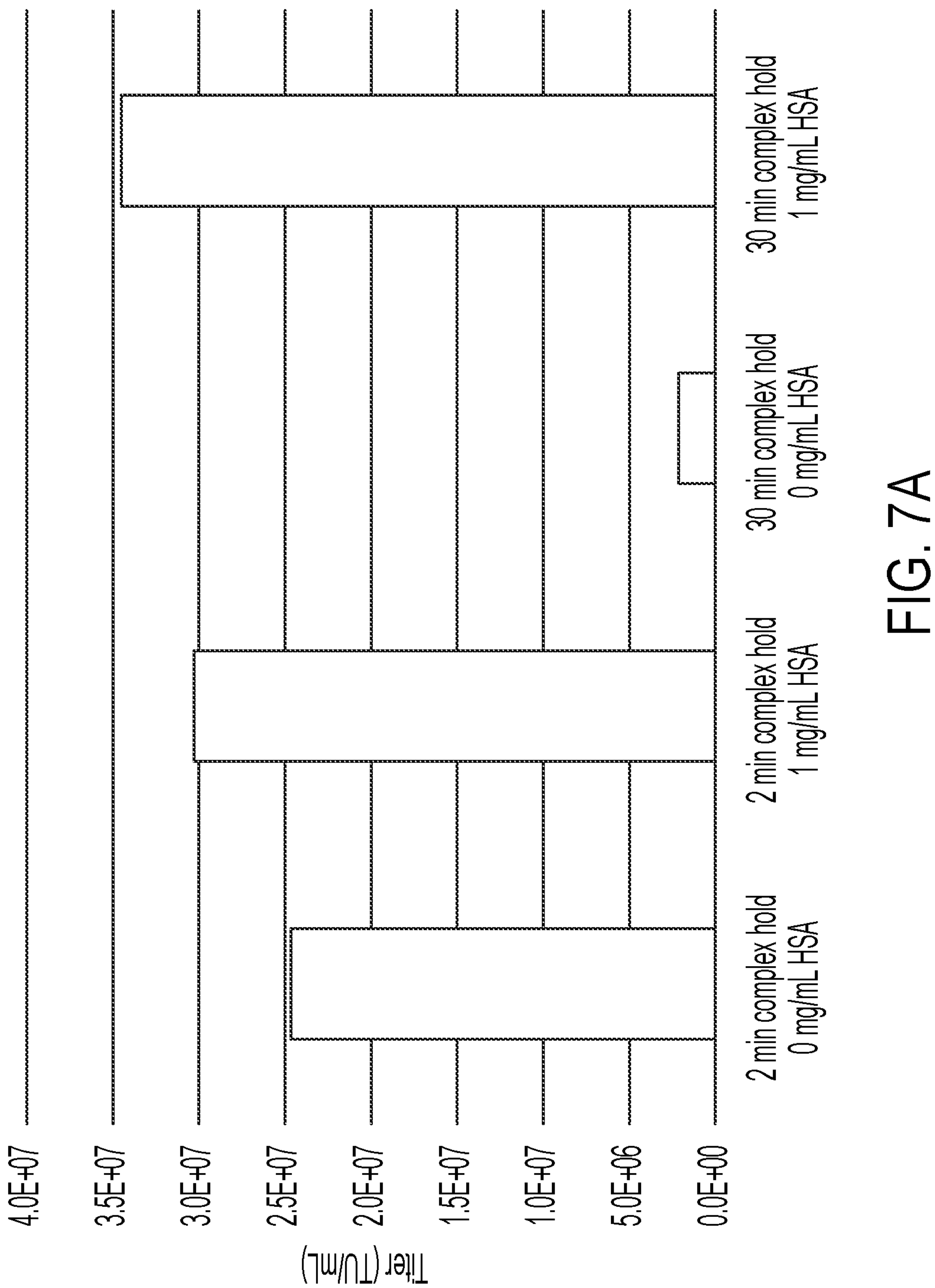
FIG. 7A shows a bar graph illustrating bioreactor titer by complex hold time, +/−HSA.

Example 3 demonstrated that supplementing a transfection complex solution after mixing the DNA and PEI solutions together prevented the loss in titer observed with extended complex incubation times for up to 30 minutes. This is graphically depicted as well at FIG. 7A. Because no significant decrease in titer was observed at the maximum hold time (30 minutes), it was not known when or if the complex incubation time would begin to impact titer at harvest after HSA addition. Thus, the impact of complex hold time after HSA addition for up to 24 hours was evaluated in this Example.

This Example was performed in cultures grown in DWPs. Three identical master mixes were made. All master mixes were prepared with a 3:1:1:1 transgene:rev:env:gag/pol molar ratio, 68.7 μg/mL DNA concentration, and a 1:1 DNA:PEI mass ratio. Each well received the volume of master mix required to bring the final DNA concentration to 2 μg/mL. Each condition for this Example was tested in triplicate.

A single seed train was expanded for all conditions. The seed train was expanded and was used to seed 2×250 mL culture in a 1 L shake flask. The cell culture was diluted to $2.1e^6$ vc/mL. The flask was placed back on a shaking incubator platform for 24 hours. Immediately after seed, three bulk DNA solutions were prepared at 137.3 μg/mL DNA and 3:1:1:1 transgene:rev:env:gag/pol molar ratio, and three bulk PEI solutions were prepared at 137.3 μg/mL. 0.6 mL of each DNA and PEI solution were aliquoted separately into 16 wells in a 96 deep well plate. 24 hours before transfection, two PEI aliquots from each bulk PEI solution were transferred into 2 separate DNA aliquots from each bulk DNA solution and mixed to prepare 6 master mix solutions. Of the 6 master mix solutions, one solution from each group of bulk PEI and DNA solution was supplemented with 24 μL 50 mg/mL HSA solution to form three stabilized complex solutions. This complex creation procedure was repeated at 18 hours, 2 hours, 1 hour, 30 minutes, 20 minutes, 10 minutes, and 2 minutes before transfection. The formed complexes and unmixed DNA and PEI cultures were stored at room temperature between formation and transfection. 24 hours after seed, the bulk cell culture was aliquoted into 24 DWPs. Three mL cell culture was transferred by pipette into 48 wells on two plates. Each well was then transfected. Each master mix prepared in the previous 24 hours was used to transfect one well. Transfections using master mixes supplemented with HSA were separated by plate from samples transfected with unsupplemented master mixes. The plate map depicted at FIG. 7B details the transfection complex hold time and HSA content for each well.

Forty-eight hours after transfection, all wells were harvested. Both plates were centrifuged at 1000×g for five minutes. 3×0.6 mL supernatant from each well was aliquoted and frozen at −80° C. Frozen samples were later analyzed for titer.

The titer assay was performed to compare the harvest titer of each well in this Example. Wells transfected with master mixes from the same bulk DNA and PEI solutions are plotted as individual curves in FIG. 7C. Specifically, FIG. 7C details the titer of all samples by complex incubation time. Wells transfected with complexes supplemented with HSA are shown as dotted lines. Wells transfected with unsupplemented PEI-DNA complexes are shown as solid lines. At FIG. 7C plots 701, 702, and 703 depict samples without HSA, and plots 704, 705, and 706 depict samples with HSA.

Figure 7C:
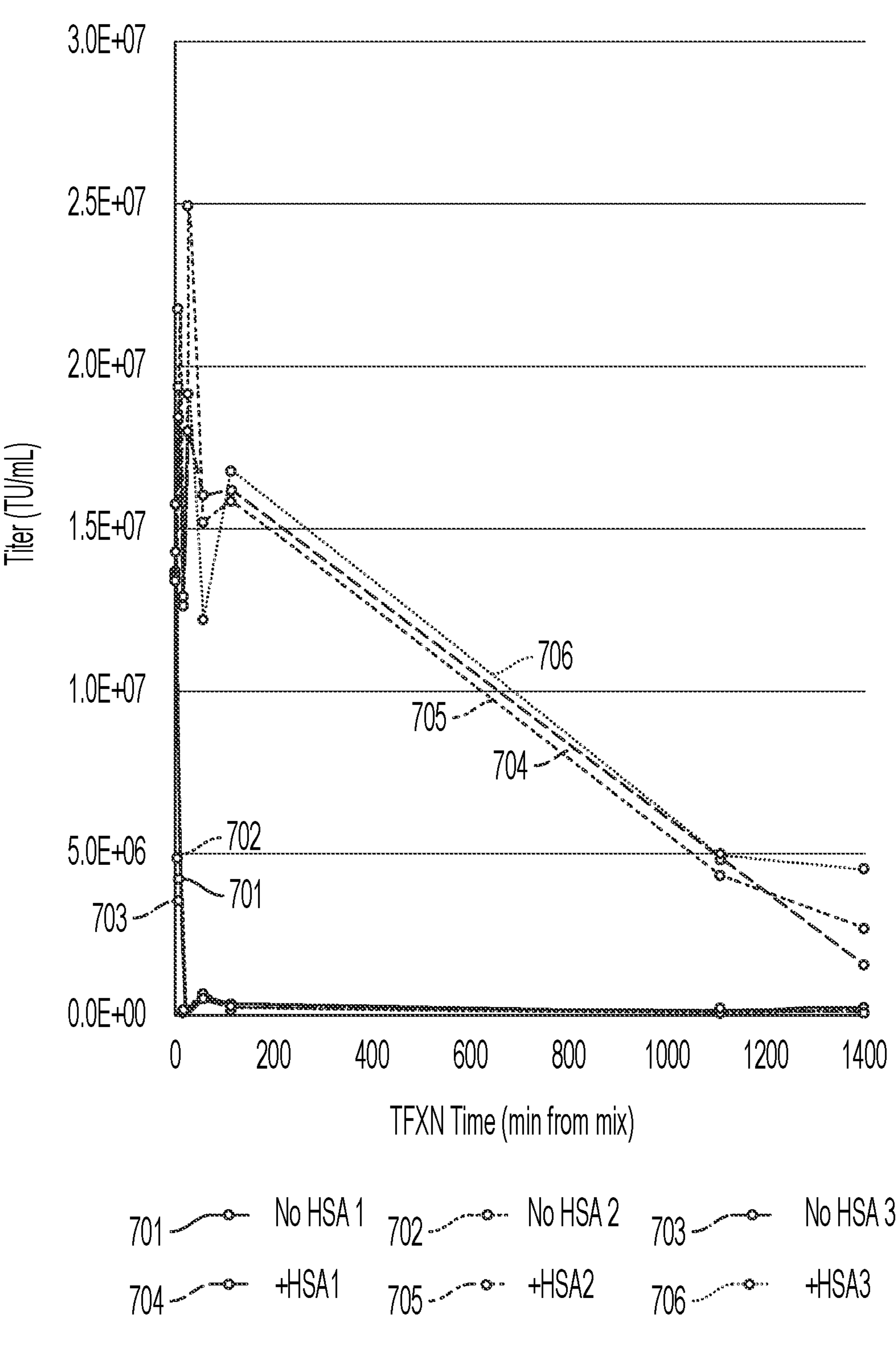
FIG. 7C is a graph that shows lentiviral vector titer at harvest after transfection of PEI-DNA complexes with and without HSA, under varying transfection complex hold times prior to transfection up to twenty-four hours.
Figure 7D:
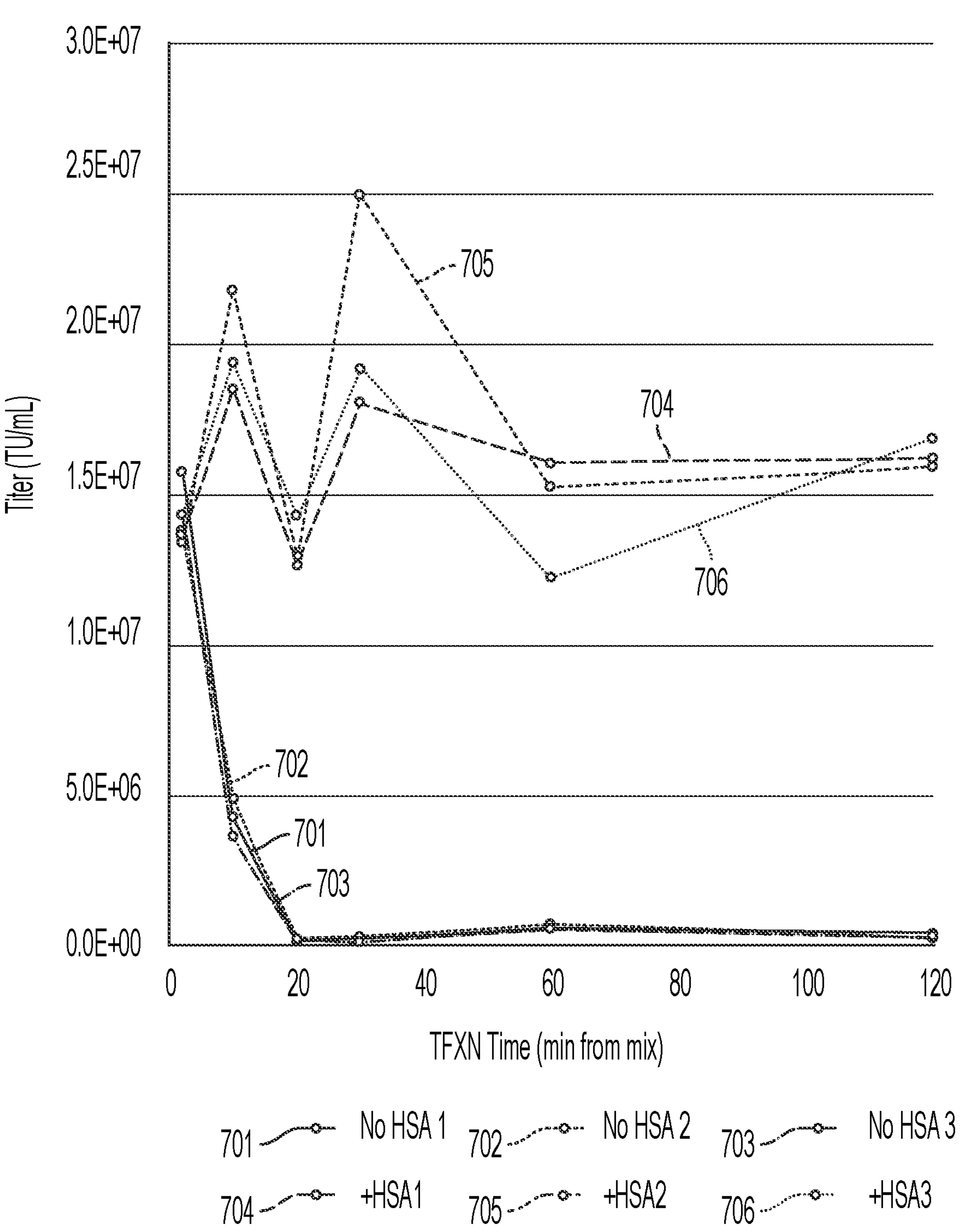
FIG. 7D depicts a portion of the graph of FIG. 7C in order to show a shortened time frame.

FIG. 7D is a graph that includes data from FIG. 7C, but condensed from a 24 hour period into a two hour time frame. Accordingly, numerals are the same at FIG. 7D as those of FIG. 7C. FIG. 7D shows that within samples transfected with HSA-supplemented complexes, certain hold times consistently result in significantly higher titers than others.

In this Example, complexes prepared to a final concentration of 68.7 μg/mL DNA produced no measurable titer in all samples transfected with complexes incubated longer than 10 minutes. In contrast, no significant differences in titer were observed in samples transfected with complexes supplemented with HSA and held for up to 2 hours. A significant decrease in titer was observed from 2 hours to 18 hours. Yet, samples transfected with supplemented complexes incubated for 18 hours still produced measurable titers, indicating that the hold time at which titers may start to decrease is somewhere between 2 hours and 18 hours and that up to 18 hours would be sufficient to generate acceptable titer levels. Furthermore, the data in FIGS. 7C-7D shows that a gradual decrease in titer occurs during this period, as opposed to a sudden collapse in titer at a specific hold time. This Example supports extending the acceptable incubation time from 30 minutes to 2 hours, and even up to 18 hours, for transfection complexes prepared at 68.7 μg/mL DNA and supplemented with HSA to 1 mg/mL.

Additional studies also found that HSA supplementation can stabilize complexes at bioreactor scales. Transfection was performed in a scale-down stirred tank bioreactor model. Four bioreactor cultures were transfected to produce viral vectors. Cultures received transfection complexes that were supplemented with 0 or 1 mg/mL HSA at 2 or 30 minutes after formation. The introduction of HSA to bioreactor scale cultures had the same stabilizing effect seen at shake flask scale. Large scale complexes were stable out to 30 minutes.

While 30 minutes provides sufficient time to prepare and introduce lab-scale transfection complexes, manufacturing scale complex preparation could require additional time. An additional complex hold experiment was performed to determine how long HSA supplemented complexes could be held before decreases in titer were observed. A transfection complex was prepared and supplemented with 0 or 1 mg/mL HSA at the desired time point after formation and was held for 2, 10, 20, 30, 60, 120, 1140, or 1440 minutes prior to addition to cells. Each culture was measured for titer.

Supplemented complexes showed stability for up to 120 minutes, while unsupplemented complexes show significant titer losses at all timepoints beyond 2 minutes. Additionally, supplemented complexes still produced measurable titers for up to 24 hours.

Example 5

Lyophilization Screening of Transfection Complexes

Figure 9:
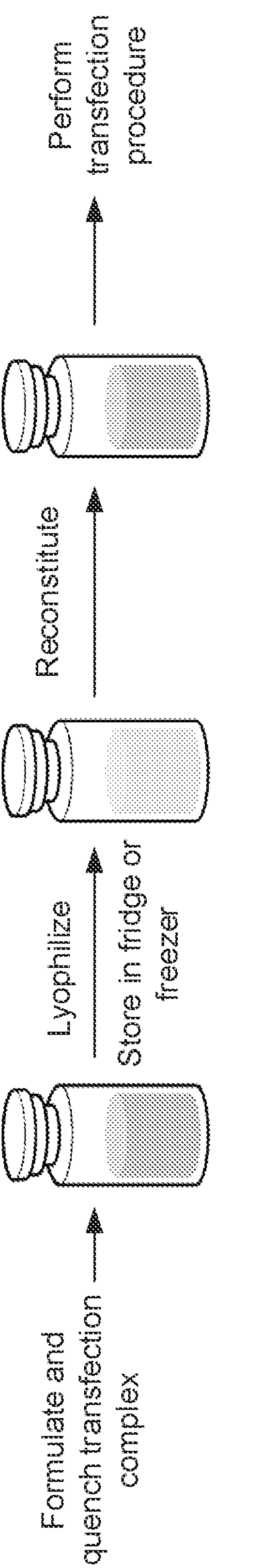
FIG. 9 depicts a process flow for lyophilization of stabilized PEI-DNA transfection complexes, followed by reconstitution and transfection.

This example demonstrates lyophilization screening of transfection complexes, in particular PEI-DNA transfection complexes, for the creation of shelf-stable transfection complexes. Advantages may include, but are not limited to, an ability to spatially and temporally separate the process of transfection complex formation from transfection unit operation, reducing risk of operational error during transfection unit operation, and improvements to lot-to-lot consistency. FIG. 9 depicts a general process flow for creating and using lyophilized transfection complexes. In general, the process steps included formulation and quenching of the transfection complex. Dynamic light scattering measurements were taken for the quenched transfection complexes. The transfection complex included DNA and a polymer (e.g., PEI), and the quenching was by HSA (recombinant or non-recombinant). Following formulation and quenching, the transfection complex was lyophilized and stored in a refrigerator (e.g., 4° C.), or freezer (e.g., −20° C. or −80° C.). At a later time, water was added to reconstitute the lyophilized transfection complex. Following reconstitution, DLS measurements were again taken to compare the size of the transfection complex with the size prior to lyophilization. Transfection of a desired population of cells was carried out following the reconstitution.

In a first study, termed a pre-lyophilization study, edge effects were examined for compositions that did not include PEI and DNA. Edge effects, as discussed herein, refer to the corner points of tested lyophilization formulations, namely highest sugar concentrations and lowest sugar concentration. The study was undertaken to understand how the additives may impact HSA lyophilization.

Thus, in the first study of this Example, different mixtures of HSA, sucrose and mannitol in water were tested for lyophilization. Six different experiments tested varying concentrations of HSA, sucrose and mannitol. Formulations without mannitol exhibited minor lyophilization cake collapse. All formulations readily reconstituted almost immediately.

In a second study, lyophilization screening of quenched transfection complexes was conducted. The lyophilization screening compositions included HSA at 1-10 mg/mL, sucrose at 0-40 mg/mL, mannitol at 0-30 mg/mL, DNA at 68.7 mg/mL, and PEI at 68.7 mg/mL in pH-neutral media. Table 6 below provides thirteen formulations made using quenched transfection complexes.

TABLE 6

Formulations for testing lyophilization of quenched PEI-DNA complexes

| Condition | [HSA] (mg/mL) | [Mannitol] (mg/mL) | [Sucrose] (mg/mL) |
|---|---|---|---|
| 1 | 1 | 0 | 0 |
| 2 | 5.5 | 0 | 40 |
| 3 | 1 | 0 | 40 |
| 4 | 5.5 | 15 | 20 |
| 5 | 1 | 15 | 0 |
| 6 | 10 | 30 | 0 |
| 7 | 1 | 30 | 20 |
| 8 | 10 | 0 | 20 |
| 9 | 5.5 | 30 | 0 |
| 10 | 1 | 30 | 40 |
| 11 | 10 | 30 | 40 |
| 12 | 10 | 0 | 0 |
| 13 | 10 | 15 | 40 |

Figure 10:
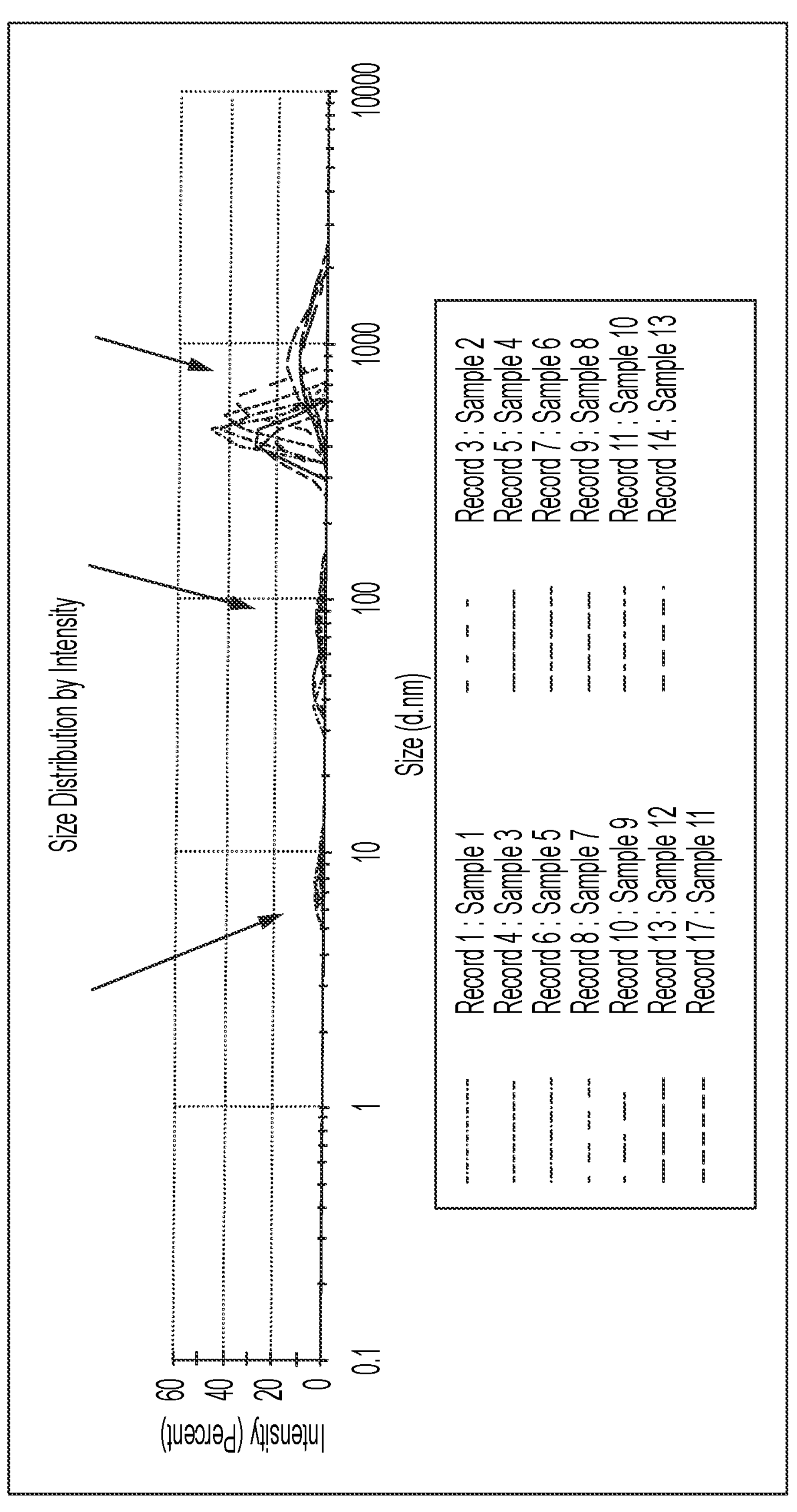
FIG. 10 is a graph plotting transfection complex size against percent intensity as monitored via dynamic light scattering (DLS) methodology, for thirteen different formulations that include DNA at 68.7 μg/mL, PEI at 68.7 μg/mL and varying concentrations of each of sucrose (0-40 mg/mL), mannitol (0-30 mg/mL) and HSA (1-10 mg/mL).
Figure 11:
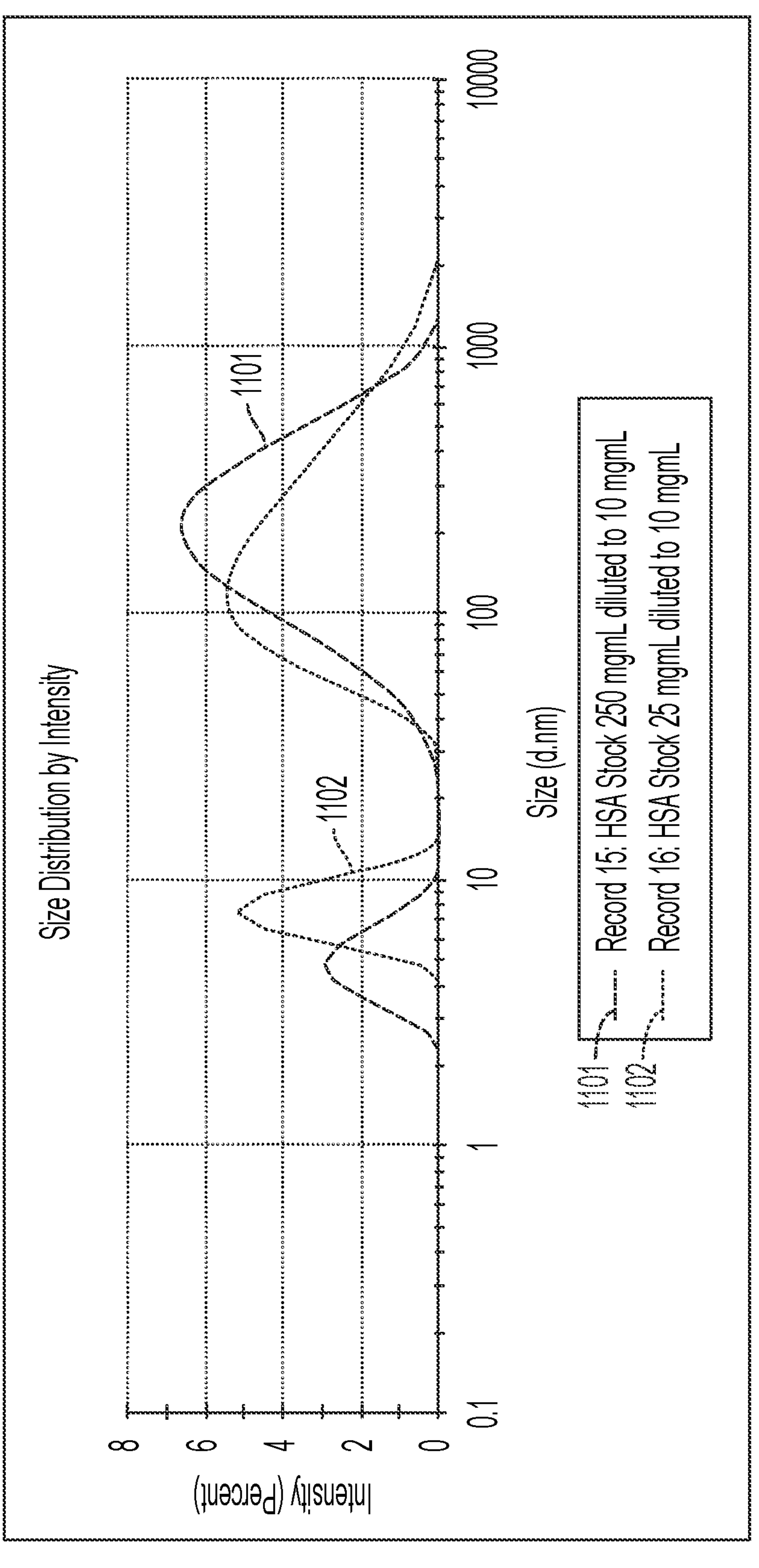
FIG. 11 is a graph plotting hydrodynamic diameter of HSA in solution (10 mg/mL) against percent intensity as monitored via DLS, illustrating that two smaller peaks as seen in the graph at FIG. 10 are due to HSA.

DLS measurements pre-lyophilization of the thirteen different conditions listed at Table 9 were obtained. The data is depicted in FIG. 10, with hydrodynamic diameter on the x-axis and percent intensity on the y-axis. Three prominent peaks were observed in each condition as depicted by arrows in FIG. 10, and correspond to ~10 d.nm, ~50-100 d.nm, and ~500-1000 d.nm. Where the peak was within a particular range (e.g., 500 or 1000 d.nm for largest peak) was sample dependent and specific to the quenched complexes. Human serum albumin was found to account for the two smaller peaks near 100 d.nm (hydrodynamic diameter) and 6-10 d.nm as shown by the data in FIG. 11. Specifically, FIG. 11 again shows hydrodynamic diameter on the x-axis and percent intensity on the y-axis, for two different HSA solutions (250 mg/mL stock HSA diluted to 10 mg/mL and 25 mg/mL stock HSA diluted to 10 mg/mL). For FIG. 11, plot 1101 is the 250 mg/mL stock HSA diluted to 10 mg/mL, and plot 1102 is the 25 mg/mL stock HSA diluted to 10 mg/mL. The largest peaks near 500-1000 d.nm are the quenched complexes in each condition and are consistent with the results shown in FIG. 6.

Figure 12:
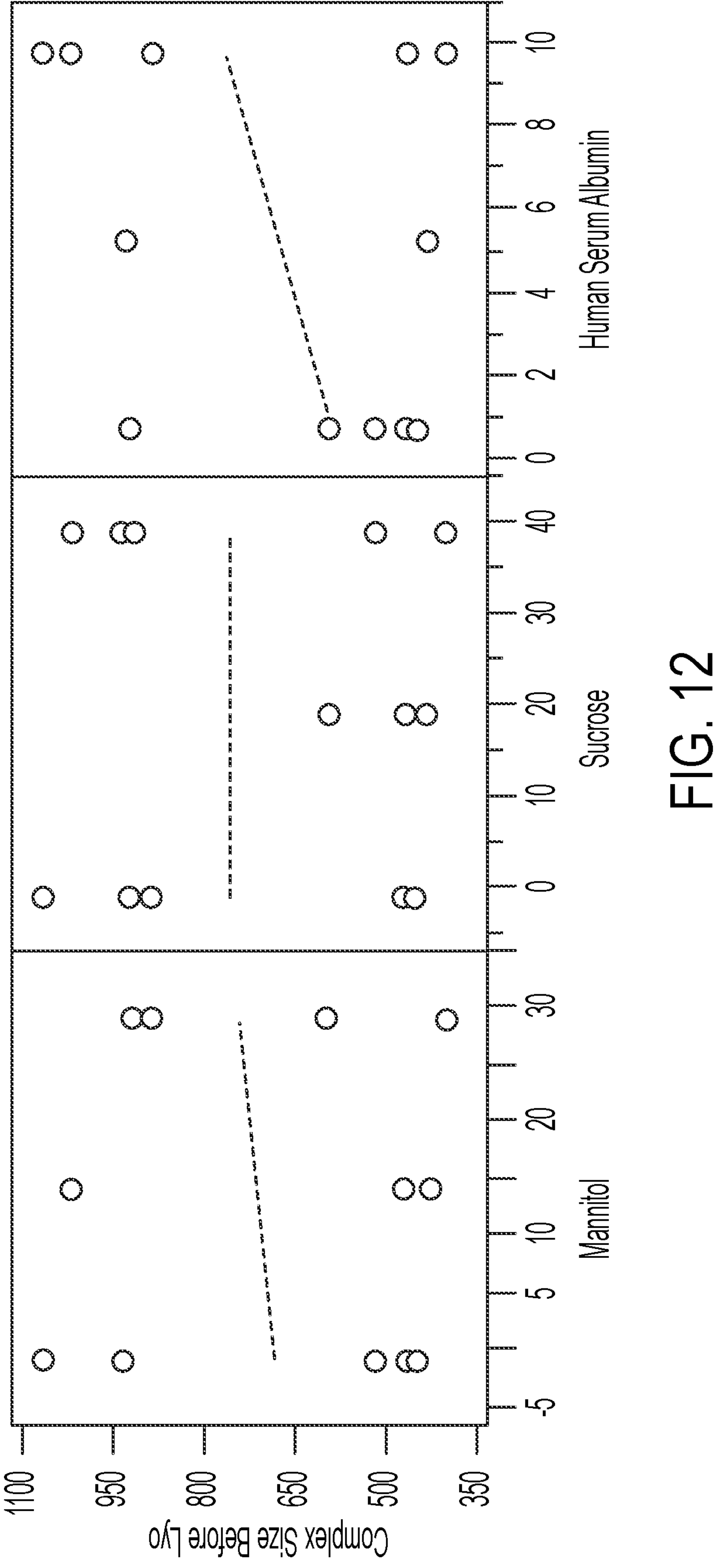
FIG. 12 depicts three different graphs that illustrate transfection complex size as a function of each of mannitol concentration, sucrose concentration and HSA concentration, for the thirteen different formulations that include DNA at 68.7 μg/mL, PEI at 68.7 μg/mL and varying concentrations of each of sucrose (0-40 mg/mL), mannitol (0-30 mg/mL) and HSA (1-10 mg/mL).
Figure 13:
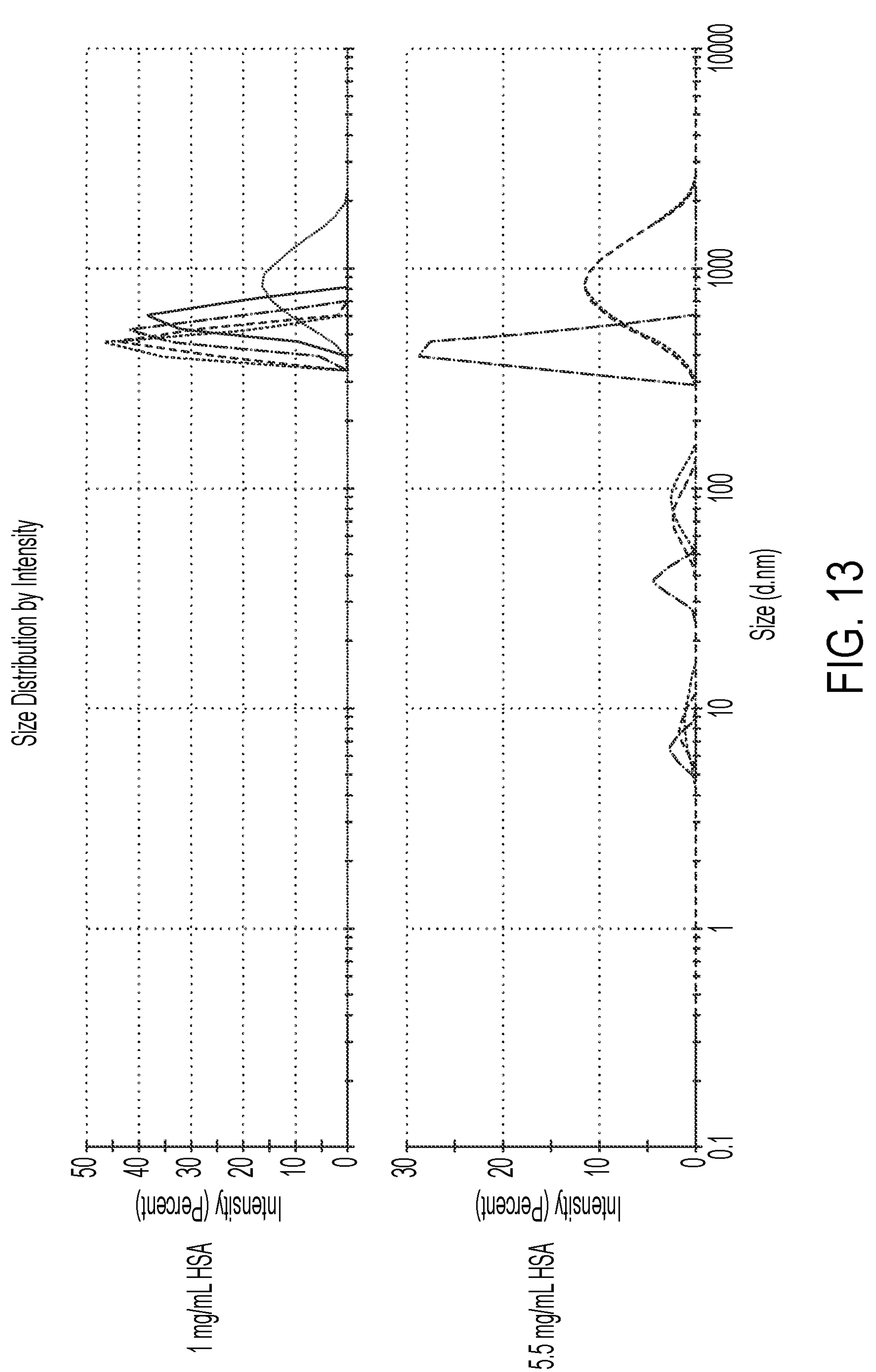
FIG. 13 depicts three different graphs that illustrate transfection complex size as a function of HSA concentration for the thirteen different formulations that include DNA at 68.7 μg/mL, PEI at 68.7 μg/mL and varying concentrations of each of sucrose (0-40 mg/mL), mannitol (0-30 mg/mL) and HSA (1-10 mg/mL).
Figure 13:
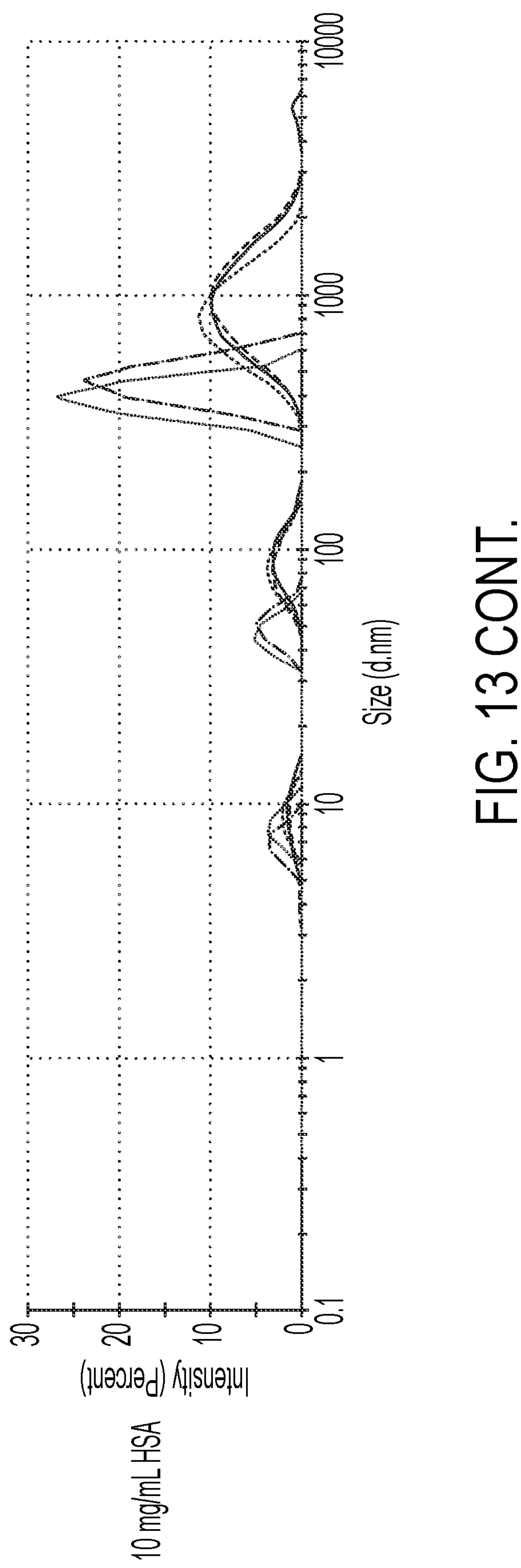

FIG. 12 shows transfection complex size as measured by DLS for the thirteen different conditions listed at Table 6 plotted separately against mannitol concentration, sucrose concentration and HSA concentration (each in mg/mL). The data shown in FIG. 12 indicates prominent complex sizes around 500 nanometers in diameter and 1000 nanometers in diameter (hydrodynamic diameter). FIG. 13 plots hydrodynamic diameter against percent intensity separately for each of the 1 mg/mL HSA formulations, the 5.5 mg/mL HSA formulations and 10 mg/mL HSA formulations (refer to Table 6). The data similarly indicates prominent complex sizes around 500 nanometers and 1000 nanometers in diameter (hydrodynamic diameter).

Additionally, formulations containing DNA, PEI, HSA and pH-neutral media alone (e.g., no sucrose or mannitol) were tested to determine if they could produce quality lyophilization cakes. Formulations lacking sucrose and mannitol produce degraded lyophilization cakes as compared to samples that include one or more of sucrose and mannitol.

Figure 14:
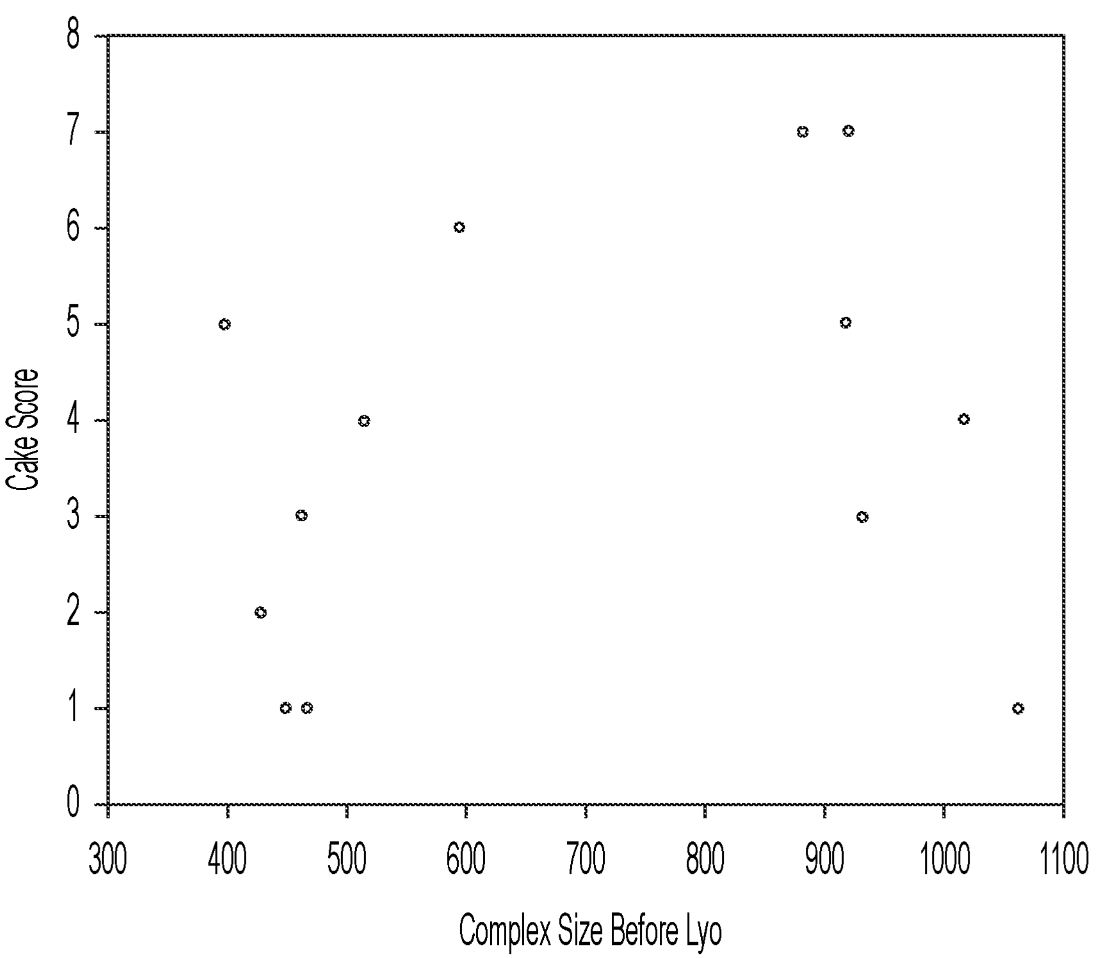
FIG. 14 depicts a graph plotting transfection complex size prior to lyophilization for each of the thirteen different formulations that include DNA at 68.7 μg/mL, PEI at 68.7 μg/mL and varying concentrations of each of sucrose (0-40 mg/mL), mannitol (0-30 mg/mL) and HSA (1-10 mg/mL), as a function of a lyophilization cake score that accounts for one or more parameters related to lyophilization cake appearance.

In order to assess whether transfection size before lyophilization was associated with lyophilization cake appearance, a lyophilization cake scoring system was generated of cake appearance. FIG. 14 shows lyophilization cake score plotted against complex size before lyophilization, for each of the thirteen different formulations depicted at Table 6. As shown, transfection complex size is not correlated with lyophilization cake appearance.

In terms of the thirteen different formulations listed at Table 6, three showed the best cake appearance as judged by the lyophilization cake scoring system mentioned above. Specifically, condition 6, condition 7 and condition 9 showed the best cake appearance. It is expected that higher scoring cakes correspond to a higher probability of retained performance (e.g., higher scoring cakes corresponding to increased titers following transfection of the reconstituted lyophilization cakes).

Example 6

Evaluation of HSA as a Quenching Agent for PEI-Adeno-Associated Virus (AAV) Plasmid Complexes This example illustrates that the addition of HSA to PEI-DNA complexes, where the DNA is an AAV plasmid as opposed to lentiviral vector plasmids, stabilizes the complexes as opposed to complexes lacking HSA addition. This Example also illustrates that the addition of HSA to PEI-DNA complexes, where the DNA is an AAV plasmid, results in higher AAV vector genomes than those complexes not treated with HSA.

For the Experiments outlined in Example 6, plasmid molar ratio for AAV was 1:1:1 pHleper, RepCap, and gene of interest (GOI) (see Table 7).

TABLE 7

Plasmid, Molecular Weight, and Plasmid Mass Ratio

| Plasmid | Molecular Weight (kDa) | Plasmid Mass Ratio |
|---|---|---|
| pHelper | 6537.245 | 0.399 |
| RepCap | 5672.48 | 0.346 |
| GOI | 4166.699 | 0.254 |

The calculated complex concentration was about 135 mg/mL for AAV, thus the complex hold time was fixed to about 5 minutes based on previously determined HSA complex hold time data. DNA bulk solution, PEI bulk solution, and HSA stock were prepared 24 hours before transfection and held at room temperature overnight. The complexes were a 1:1:1 molar ratio of the AAV plasmids (see Table 7). The PEI to DNA mass ratio used was 2:1, and the volume ratio for adding PEI to DNA solutions was 1:1. 16 individual complexes were formed in 15 mL conical tubes at their respective timepoints (0, 2, 6, 24 hours before transfection) for each flask and then quenched with either HSA at 1 mg/mL or transfection media of similar volume of quenching reagent to complex volume ratio (about 4% of the complex solution). Specifically, complex stability was evaluated with and without addition of HSA after 5 minutes of complex formation, and following transfection after the quenched complex was held for 0, 2, 6 and 24 hours. To determine if HSA is able to stabilize PEI-AAV DNA complexes, the response in vector genomes was evaluated. Experimental time points were evaluated in duplicate, for each of HSA at 0 mg/mL and 1 mg/mL.

Figure 15:
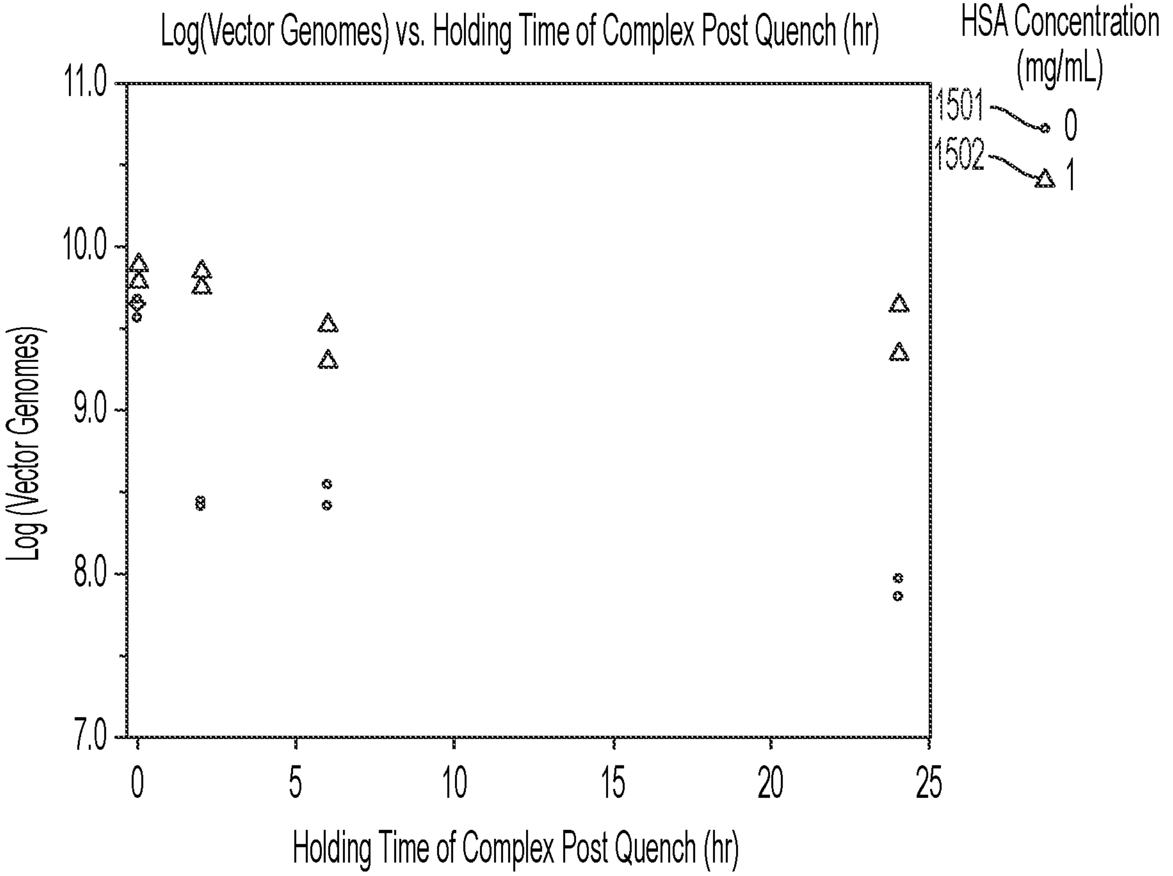
FIG. 15 depicts a graph plotting log(vector genomes) as a function of holding time of PEI-DNA complexes+/−HSA (1 mg/mL) that include adeno-associated virus (AAV) plasmid as the DNA in the complex.

For the transfection/innoculation, 125 mL Erlenmeyer flasks were used, with a volume of 30 mL. Flasks were incubated at 37° C. at 120 RPM, at 8% $CO_2$ and 85% humidity. Cell growth media used was BalanCD, 4 mM Glutamax, 0.1% Poloxamer 188. For the determination of vector genomes, 3 mLs of cells from each condition were lysed in 0.5% (v/v) Triton-X 100 (final concentration) at 37° C. for 4 hours, followed by centrifugation at 3000×g to remove cellular debris. FIG. 15 illustrates that the addition of HSA to PEI-AAV DNA complexes as a quenching/stabilizing agent results in increased vector genomes at all time points examined other than the 0 time point (e.g., 2 hours, 6 hours and 24 hour hold times post-quench and prior to transfection). As mentioned, experimental time points were evaluated in duplicate, for each of HSA at 0 mg/mL (circles 1501) and 1 mg/mL (triangles 1502). In summary, HSA can be used as a quenching/stabilizing agent for PEI-AAV DNA complexes as well as PEI-LVV DNA complexes.

Example 7

Evaluation of Recombinant Proteins as Complex Stabilizers

This Example screened proteins for use as PEI-DNA complex stabilizers, with the goal of identifying a recombinant protein capable of stabilizing TFXN complexes.

As disclosed herein, Human serum albumin (HSA) is used in PEI mediated transfections to stabilize the TFXN complex by preventing further complex aggregation. Replacing HSA with a recombinant protein that replicated the stabilizing effect of HSA would keep the 293LV suspension process to remain animal and human derived component free while still allowing operator control over the TFXN complex size.

To better understand the stabilizing effect of different proteins on the TFXN complex and to understand how complex behavior changes with changes in preparation parameters, HSA was tested as a stabilizing supplement. Proteins screened for potential stabilizing effects, in addition to HSA, included Optibumin (Invitria, Junction City, KS), *P. pastoris* r-albumin (Sigma), rice r-albumin (Sigma-Aldrich, St. Louis, MO), Exbumin (Invitria, Junction City, KS), r-transferrin (Sigma-Aldrich, St. Louis, MO), r-insulin (Sigma-Aldrich, St. Louis, MO) and fetal bovine serum (FBS) (Hyclone, Logan, UT). In this example "r-protein" refers to "recombinant protein", for example, "r-albumin" refers to recombinant albumin.

Each protein was solubilized in balanCD media to a final concentration of 50 mg/mL, with the exception of FBS. Because the exact protein concentration of FBS is not specified, the volume of FBS added was 1.96% of the total complex solution, both to equate the volume added to the other supplementary solutions and to allow for the calcium phosphate transfection complex to be quenched with media containing a final FBS v/v concentration of 1.96%. To perform the complex sizing measurements, a bulk 137.3 μg/mL DNA and 137.3 μg/mL PEI solution were made at 10 mL each. 1.37 mL of plasmid p10021 (Lot 82094) were added to 8.63 mL balanCD to produce the DNA solution. 1.37 mL of PEI (Lot 26033C1B) were added to 8.63 mL balanCD to create the PEI solution. For each run, 0.6 mL DNA solution was placed in a Sarstedt square 12 mm×12 mm×45 mm clear polystyrene cuvette (Sarstedt, Newton, NC, PN 67.754) and placed in the zetasizer DLS cuvette holder. 0.6 mL PEI solution was added by pipette and the solution was briefly mixed. The zetasizer software was initiated to take 15 s particle size reads using DLS for 3 minutes. The measurement was then paused for 70 s and 24 μL of one protein solution was added to the cuvette and the solution was mixed. The DLS measurements were then continued in 30 seconds averages for 30 minutes.

The experimental procedures in this Example were conducted on different days. All solutions were stored in a 2-8° C. refrigerator between read days. On the first day, the procedure detailed above was performed on complexes supplemented with HSA, Optibumin, *P. pastoris* r-albumin, and rice r-albumin. All solutions were brought to room temperature (RT) before measuring. On the second day, the procedure detailed above was repeated for complexes supplemented with r-transferrin, r-insulin, and FBS. All solutions were brought to RT before complex formation. On the third day, the procedure detailed above was repeated for complexes supplemented with Exbumin. All solutions were brought to RT before complex formation.

Figure 16:
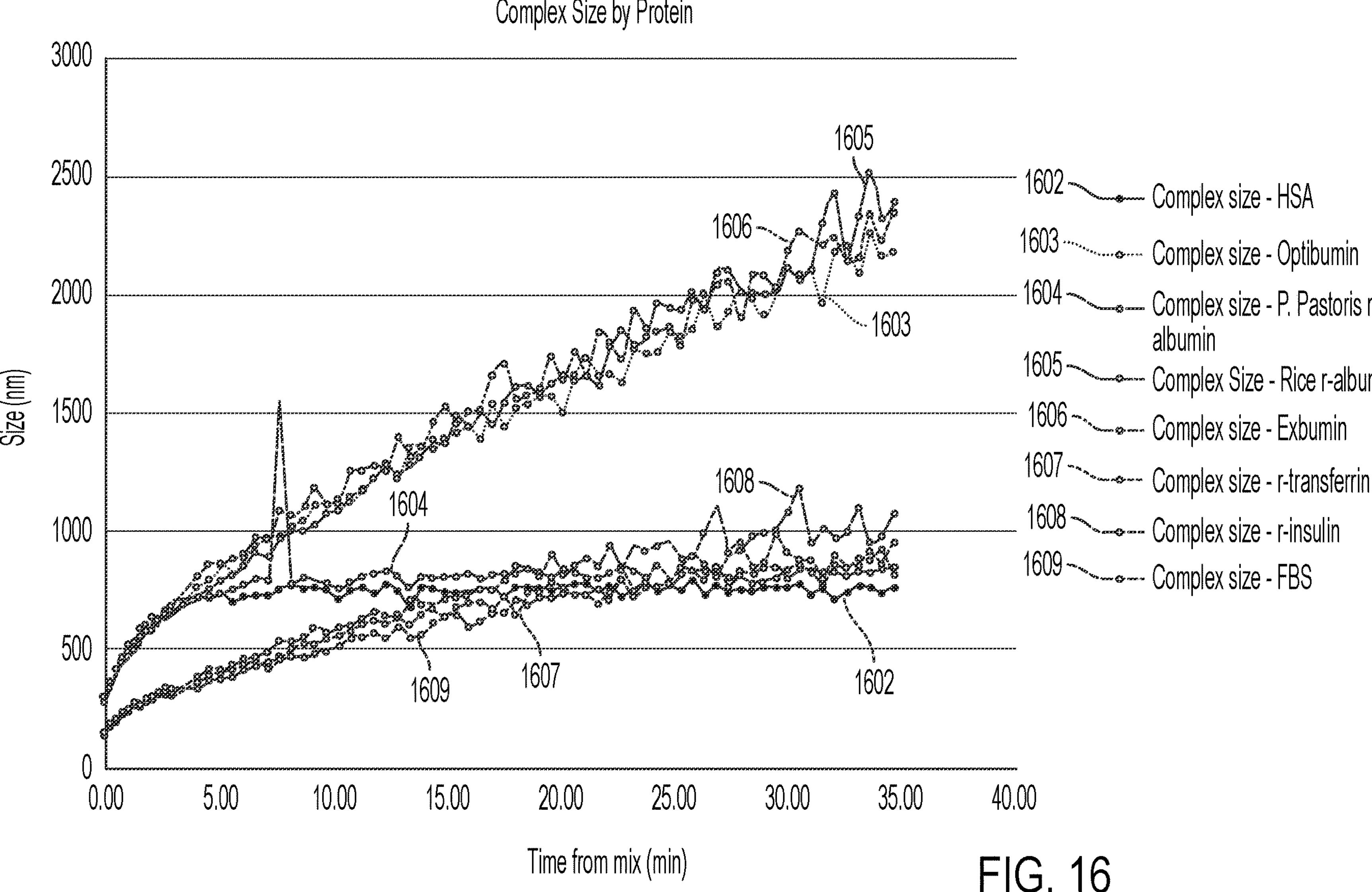
FIG. 16 is a graph that shows changes in PEI-DNA transfection complex size over time when recombinant albumins and various proteins other than HSA are used as potential PEI-DNA transfection complex stabilizers.
Figure 17:
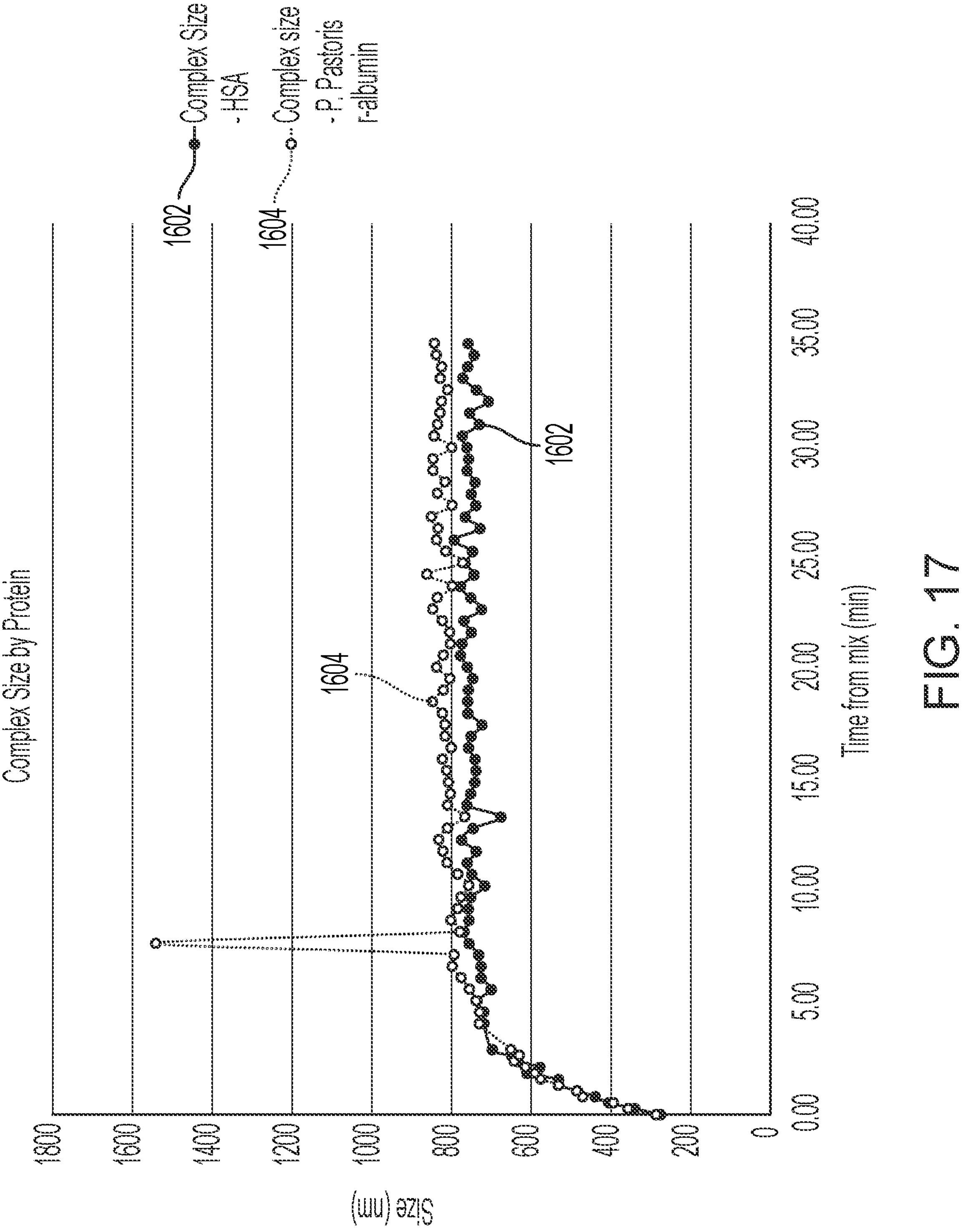
FIG. 17 is a graph that shows PEI-DNA transfection complex size over time when recombinant albumin from *P. Pastoris* is used as compared to HSA.

The results of the measurements are shown at FIG. 16. Of the human albumins tested, just HSA and *P. pastoris* derived r-albumin demonstrated a complex stabilizing effect. GMP (good manufacturing process) r-albumins (e.g., Optibumin, Exbumin) and the rice derived r-albumin demonstrated no stabilizing effect. For reference, FIG. 17 plots just a portion of the graph of FIG. 16, specifically, FIG. 17 is a graph showing the effects of *P. Pastoris* derived r-albumin-albumin on PEI-DNA complex size as compared to HSA. For FIG. 16 plot 1602 is HSA, plot 1603 is Optibumin, plot 1604 is *P. pastoris*-derived r-albumin, plot 1605 is rice-derived r-albumin, plot 1606 is Exbumin, plot 1607 is r-transferring, plot 1608 is r-insulin, and plot 1609 is FBS. FIG. 17 shows data also plotted at FIG. 17, so the numerals are the same. Specifically, plot 1602 is HSA and plot 1604 is *P. pastoris*-derived r-albumin.

The complexes quenched with FBS, r-insulin, and r-transferrin appear to be smaller initially and to grow at a slower rate. The smaller initial starting size may be the result of a quicker mix-to-instrument initialization period. Shortening this period may mean the complex may have less time to form between mixing and the start of the first read, resulting in a smaller complex size. However, this does not explain why the complex formation rate is slower for these complexes both before and after supplementation for this day. Because identical DNA and PEI solutions were used for all proteins tested, the root cause of this change in rate cannot be pinned on a mistake in solution preparation. DNA or PEI degradation during the periods between reads is a possibility, but also unlikely as it would not explain why the complex formation slowed for the second day, but then on the third day increased back to levels observed on the first day. Regardless, the behavior of the complex before and after supplementation demonstrates a clear understanding of how the protein is interacting with the complex, and is still considered representative of the stabilization potential of r-insulin, r-transferrin, and FBS.

The behavior of the transfection complex in the presence of FBS in the present study differed from what had been observed previously. In these previous studies, FBS had been observed to both decrease and stabilize the particle size upon addition to the transfection complex solution. This behavior was not observed in this Example, and although the complex size increased slower in the FBS-supplemented solution than other solutions, the difference in rate of size change is similar to other samples performed on the same day and is not thought to be a result of the FBS addition. The differences in effect after FBS addition may be explained by the differences in complex preparation parameters or by the differences in supplementation technique. Complexes in the present study were prepared with 68.7 μg/mL DNA and with a 1:1 DNA:PEI mass ratio. Complexes in previous studies were prepared with 26.8 μg/mL DNA and a 1:2.4 DNA:PEI mass ratio. FBS concentrations in such studies were also slightly higher: the present study prepared complexes with a final FBS v/v ratio of 1.96%, while previously they saw stabilization in complexes prepared with final FBS v/v ratios of 2.5% and 4.05%. Another significant factor could be the addition procedure: this experiment added FBS in concentrate and limited its volume to 1.96% of the total complex solution volume. Previous studies added FBS diluted in media. The diluted FBS solution would be added in a volume equal to or greater than the complex solution. The doubling of the complex solution volume would slow down the rate of complex size change. Assuming FBS does stabilize the complex, a more dilute complex may require a lower concentration of FBS to stabilize the complex.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of transfecting a population of cells with a polymer-DNA complex, comprising:

(a) mixing together a first solution comprising deoxyribonucleic acid (DNA) with a second solution comprising a cationic polymer, wherein the cationic polymer is polyethyleneimine (PEI), to obtain a polyplex solution comprising a PEI-DNA complex;

(b) at a first predetermined time subsequent to mixing together the first solution and the second solution, adding a polyplex stabilizing agent to the polyplex solution to obtain a stabilized PEI-DNA complex; and (c) at a second predetermined time subsequent to adding the polyplex stabilizing agent to the polyplex solution, transfecting the population of cells with the stabilized PEI-DNA complex;

wherein the second predetermined time is between about 30 minutes and about 18 hours, and wherein the polyplex stabilizing agent is a human serum albumin (HSA).

2. The method of claim 1, wherein the population of cells is a population of suspension cells.

3. The method of claim 2, wherein the population of cells comprises human embryonic kidney (HEK) 293 cells.

4. The method of claim 3, wherein the first solution comprising DNA comprises transfer plasmids that code for at least a portion of a lentiviral genome.

5. The method of claim 3, wherein the first solution comprising DNA comprises transfer plasmids that code for at least a portion of an adeno-associated viral genome.

6. The method of claim 1, wherein the stabilized PEI-DNA complex has a size between about 400 nanometers and about 1000 nanometers in diameter.

7. The method of claim 1, wherein the stabilized PEI-DNA complex has a size between about 400 nanometers and about 700 nanometers in diameter.

8. The method of claim 1, wherein the first predetermined time is between about 2 minutes and about 5 minutes.

9. The method of claim 1, wherein the second predetermined time is between about 1 hour and about 2 hours.

10. The method of claim 1, wherein the second predetermined time is between about 30 minutes and about 60 minutes.

11. The method of claim 1, wherein the polyplex stabilizing agent is a non-recombinant human serum albumin (HSA).

12. The method of claim 1, wherein the polyplex stabilizing agent is a recombinant human serum albumin (HSA).

13. The method of claim 1, wherein the first predetermined time is between about 30 seconds and about 15 minutes.

14. The method of claim 13, wherein the first predetermined time is between about 2 minutes and about 5 minutes.

15. The method of claim 13, wherein the second predetermined time is between about 1 hour and about 2 hours.

16. The method of claim 13, wherein the second predetermined time is between about 30 minutes and about 60 minutes.

17. The method of claim 13, wherein the stabilized PEI-DNA complex has a size between about 400 nanometers and about 1000 nanometers in diameter.

18. The method of claim 13, wherein the stabilized PEI-DNA complex has a size between about 400 nanometers and about 700 nanometers in diameter.

19. The method of claim 1, wherein the mixing of the first solution with the second solution is performed at a predetermined temperature, wherein the predetermined temperature is between 19° C. and 37° C.

20. The method of claim 1, further comprising adding one or more lyophilization agents to the PEI-DNA complex which has been stabilized with the polyplex stabilizing agent and lyophilizing it to a powder.

21. The method of claim 20, further comprising reconstituting the lyophilized stabilized PEI-DNA complex into a transfection solution.

* * * * *